US011730723B2

(12) United States Patent
Gopinathan et al.

(10) Patent No.: US 11,730,723 B2
(45) Date of Patent: Aug. 22, 2023

(54) COMPOUNDS AND METHODS FOR TREATING VIRAL INFECTIONS

(71) Applicant: Lexicon Pharmaceuticals, Inc., The Woodlands, TX (US)

(72) Inventors: Suma Gopinathan, Conroe, TX (US); Praveen Tyle, Spring, TX (US); Qi Melissa Yang, The Woodlands, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 17/233,830

(22) Filed: Apr. 19, 2021

(65) Prior Publication Data

US 2022/0054464 A1 Feb. 24, 2022

Related U.S. Application Data

(60) Provisional application No. 63/013,413, filed on Apr. 21, 2020.

(51) Int. Cl.
*A61K 31/444* (2006.01)
*A61P 31/14* (2006.01)

(52) U.S. Cl.
CPC ............ *A61K 31/444* (2013.01); *A61P 31/14* (2018.01)

(58) Field of Classification Search
CPC .................................................... A61K 31/444
See application file for complete search history.

(56) References Cited

U.S. PATENT DOCUMENTS

| | | | |
|---|---|---|---|
| 9,403,832 | B2 | 8/2016 | Bi et al. |
| 9,682,982 | B2 | 6/2017 | Bi et al. |
| 9,902,722 | B2 | 2/2018 | Luo et al. |
| 2022/0054465 | A1 | 2/2022 | Wu et al. |
| 2022/0096481 | A1 | 3/2022 | Gopinathan et al. |

FOREIGN PATENT DOCUMENTS

| | | | |
|---|---|---|---|
| WO | 2015142714 | A1 | 9/2015 |

OTHER PUBLICATIONS

Zumla et al. "Coronaviruses—drug discovery and therapeutic options," Nat. Rev. Drug Discov. May 2016; 15(5) 327-47 (Year: 2016).*

(Continued)

*Primary Examiner* — Shengjun Wang
(74) *Attorney, Agent, or Firm* — Viksnins Harris Padys Malen LLP

(57) ABSTRACT

Provided herein are methods of treating, managing and/or preventing viral infections. A particular method comprises administering to a subject in need thereof an effective amount of an adaptor associated kinase 1 inhibitor of Formula (I):

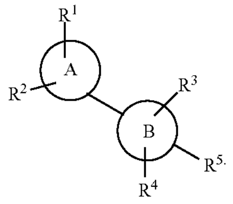

(I)

3 Claims, 17 Drawing Sheets

Specification includes a Sequence Listing.

(56) References Cited

OTHER PUBLICATIONS

Richardson et al. "Baricitinib as potential treatment for 2019-nCoV acute respiratory disease", the Lancet, Feb. 15, 2020, vol. 395, e30 (Year: 2020).*
Dorosky et al. "AAK1 and GAK inhibitors demonstrate activity against Filoviruses" J. Immunology, May 1, 2018, 200 (1 supplement) 50.7 (Year: 2018).*
Agajanian et al. "WNT activates the AAK1 kinase to promote clathrin-mediated endocytosis of LRP and establish a negative feedback loop," Cell Reports, 2019, vol. 26, pp. 79-93 (Year: 2019).*
Almeida et al., "Virology: Coronaviruses," Nature, 220(5168): 650 (1968).
Conner and Schmid, "Identification of an adaptor-associated kinase, AAK1, as a regulator of clathrin-mediated endocytosis" J. Cell Bio. 156: 921-929 (2002).
Conner et. al., "AAK1-Mediated μ2 Phosphorylation is Stimulated by Assembled Clathrin" Traffic, 4: 885-890 (2003).
Cui et al., "Origin and evolution of pathogenic coronaviruses" Nature Reviews, Microbiology, 17(3): 181-192 (2019).
Dwivedi et al., "Genomics, proteomics and evolution of Dengue virus," Briefings in functional genomics, 16(4): 217-227 (2017).
Fehr et al., "Coronaviruses: An Overview of Their Replication and Pathogenesis" Coronaviruses, 1282: 1-23 (2015).
Geller et al., "Human coronaviruses: insights into environmental resistance and its influence on the development of new antiseptic strategies," Viruses. 4(11): 3044-2068 (2012).
Hassan et al., "Association between hepatitis B virus and pancreatic cancer," Journal of Clinical Oncology, 26(28): 4557-4562 (2008).
Henderson and Conner, "A Novel AAK1 Splice Variant Functions at Multiple Steps of the Endocytic Pathway," Mol. Biol. Cell., 18(7), 2698-2706 (2007).
Howard, "The Biology of Hepadnaviruses," The Journal of General Virology, 67(7): 1215-1235 (1986).
Jackson et. al., "Clathrin promotes incorporation of cargo into coated pits by activation of the AP2 adaptor μ2 kinase" J. Cell. Biol. 163(2), 231-236 (2003).
Kahn et al., "History and recent advances in coronavirus discovery" The Pediatric Infectious Disease Journal. 24 (11 Suppl): S223-27, discussion S226 (2005).
Korba et al., A cell culture assay for compound which inhibit hepatitis B virus replication. Antiviral Research, 15: 217-228 (1991).
Korba et al., "Use of a standardized cell culture assay to assess activities of nucleoside analogs again hepatitis B virus replication," Antiviral Research, 19: 55-70 (1992).
Lau et al., "Molecular Epidemiology of Human Coronavirus OC43 Reveals Evolution of Different Genotypes over Time and Recent Emergence of a Novel Genotype due to Natural Recombination," Journal of Virology, 85(21): 11325-11337 (2011).
Lee, Paul, "Molecular epidemiology of human coronavirus OC43 in Hong Kong" (Thesis). The University of Hong Kong Libraries. doi:10.5353/th); the ncbi.nlm.nih.gov website, 59 pages (2007).
Li et al., "Structure of SARS Coronavirus Spike Receptor-Binding Domain Complexed with Receptor," Science. 309 (5742): 1864-1868 (2005).
Li et al., "Structure, Function, and Evolution of Coronavirus Spike Proteins" Annual Review of Virology. 3(1): 237-261 (2016).
Lim et al., Human Coronaviruses: A Review of Virus-Host Interactions Diseases. 4(3): 26, 28 pages (2016).
Lu et al., "Associating HIV-1 envelope glycoprotein structures with states on the virus observed by smFRET," Nature, 568(7752): 415-419 (2019).
Lu et al.,"Illuminating the virus life cycle with single-molecule FRET imaging," Advances in Virus Research 105: 239-273 (2019).
Middle East respiratory syndrome coronavirus (MERS-CoV). WHO website, 5 pages, printed, Aug. 11, 2022. https://www.who.int/news-room/fact-sheets/detail/middle-east-respiratory-syndrome-coronavirus-(mers-cov)?gclid=CjwKCAjw0dKXBhBPEiwA2bmObVKHLg8PPJkTdzuTzrfWwEYDE4dW6rdKaUvXekxQNRfMqZLrW2VBRoC9JAQAvD_BwE.
Motley et al., "Functional Analysis of AP-2 alpha and mu2 Subunits," Molecular Biology of the Cell, 17: 5298-5308 (2006).
Munro et al., "Conformational dynamics of single HIV-1 envelope trimers on the surface of native virions," Science, 346 (6210): 759-763 (2014).
Normile, "Surprising New Dengue Virus Throws a Spanner in Disease Control Efforts," Science, 342(6157): 415 (2013).
Pi et al., "Murine Leukemia Virus Exploits Innate Sensing by Toll-Like Receptor 7 in B-1 Cells To Establish Infection and Locally Spread in Mice," Journal of Virology, 93(21): e00930-19 (2019).
Reed et al., "A simple method of estimating fifty percent endpoints," American Journal of Epidemiology, 27(3): 493-497 (1938).
Ricotta et. al., "Phosphorylation of the AP2 subunit by AAK1 mediates high affinity binding to membrane protein sorting signals," The Journal of Cell Biology, 156(5): 791-795 (2002).
Rodenhuis-Zybert et al., "Dengue virus life cycle: viral and host factors modulating infectivity," Cellular and Molecular Life Sciences, 67(16): 2773-2786 (2010).
Ryu et al., "Molecular Virology of Human Pathogenic Viruses," Academic Press, 25 pages (2017).
Sewald et al., Retroviruses use CD169-mediated trans-infection of permissive lymphocytes to establish infection, Science, 350(6260): 563-567 (2015).
Su et al., "Epidemiology, Genetic Recombination, and Pathogenesis of Coronaviruses," Trends in Microbiology, 24(6): 490-502 (2016).
Uchil et al., "In Vivo Imaging-Driven Approaches to Study Virus Dissemination and Pathogenesis," Annual Review of Virology 6,: 501-524 (2019).
Ventura et al., "Longitudinal bioluminescent imaging of HIV-1 infection during antiretroviral therapy and treatment interruption in humanized mice," PLoS Pathogens, 15(12): 1-29 (2019).
WHO, "Dengue Guidelines for Diagnosis, Treatment, Prevention and Control," World Health Organization, 160 pages, ISBN 978-92-4-154787-1 (2009).
Woo et al., "Coronavirus Genomics and Bioinformatics Analysis" Viruses, 2(8):1804-1820 (2010).
Zhu et al., "A Novel Coronavirus from Patients with Pneumonia in China, 2019," The New England Journal of Medicine, 382(8): 727-733 (2020).
Zou, et al., SARS-CoV-2 Viral Load in Upper Respiratory Specimens of Infected Patients, New England Journal of Medicine, 382: 1177-1179 (2020).
Zuckerman, "Chapter 70: Hepatitis Viruses," Medical Microbiology, 4th Edition, 13 pages (1996).
Zumla et al., "Middle East respiratory syndrome," Lancet, 386(9997): 995-1007 (2015).

* cited by examiner

| Concentration Compound 1 (μM) | Media Control | | | | PLastic Control | | | |
|---|---|---|---|---|---|---|---|---|
| 0.03<br>0.1<br>0.32<br>1<br>3.16<br>10 | Toxicity Drug 1 | Cell Control / Virus Control | Low<br>Drug 1<br>High | Toxicity Drug 1 | Toxicity Drug 2 | Low<br>Drug 2<br>High | Cell Control / Virus Control | Toxicity Drug 2 |
| | Color Control Drug 1 (High to Low) | | | | Color Control Drug 2 (High to Low) | | | |

Raw Data Compound 1 (μM)

| | | | | | | | | | | | |
|---|---|---|---|---|---|---|---|---|---|---|---|
| 0.213 | 0.180 | 0.184 | 0.182 | 0.190 | 0.212 | 0.052 | 0.048 | 0.065 | 0.060 | 0.064 | 0.049 |
| | 1.690 | | | | | 1.797 | 0.243 | 0.212 | 0.266 | 1.979 | 1.978 |
| | 1.655 | | | | | 1.522 | 0.209 | 0.279 | 0.213 | 1.765 | 1.758 |
| | 1.687 | | | | | 1.604 | 0.238 | 0.208 | 0.214 | 1.743 | 1.951 |
| | 0.214 | | | | | 1.449 | 0.257 | 0.205 | 0.327 | 0.253 | 1.848 |
| | 0.209 | | | | | 1.676 | 1.150 | 1.144 | 1.443 | 0.215 | 2.036 |
| | 0.184 | | | | | 0.202 | 0.170 | 0.172 | 0.176 | 0.229 | 0.219 |
| | | | | | | 0.218 | 0.219 | 0.213 | 0.217 | 0.211 | 0.244 |

Reagent: 0.194
Virus Control: 0.024
Cell Control: 1.560
Differential: 1.536

| Compound 1 | 25% | 50% | 95% |
|---|---|---|---|
| TC (μM) | 4.21 | 5.67 | 9.44 |
| EC (μM) | 1.52 | 2.4 | > 10 |
| Theraputic Index (TI) | 2.77 | 2.34 | < 1.00 |

| Compound 1 | Antiviral Test Values | | Cytotoxicity Test Values | | |
|---|---|---|---|---|---|
| Conc (μM) | Mean OD 450/650 | % Red. In Viral CPE | Mean OD 450/650 | % Cell Viability | Colorimetric Control |
| 0.03 | -0.027 | 0.00 | 1.643 | 100 | 0.051 |
| 0.1 | -0.001 | 0.00 | 1.429 | 92 | 0.017 |
| 0.32 | -0.021 | 0.00 | 1.560 | 100 | 0.024 |
| 1 | 0.027 | 1.75 | 1.436 | 92 | 0.019 |
| 3.16 | 1.003 | 65.28 | 1.637 | 100 | 0.026 |
| 10 | -0.069 | 0.00 | -0.008 | 0 | 0.025 |

FIG. 1

COMPOUNDS AND METHODS FOR TREATING VIRAL INFECTIONS

1. FIELD OF THE INVENTION

This invention relates to the treatment, management and prevention of viral infections and to compounds useful therein.

2. SEQUENCE LISTING

The present application includes a Sequence Listing in electronic format. The Sequence Listing is provided as a file entitled "2021-11-03_01136-0005-00US_Seq_List_ST25" created on Nov. 3, 2021, which is 135 kilobytes in size. The information in the electronic format of the sequence listing is incorporated herein by reference in its entirety.

3. BACKGROUND OF THE INVENTION

Coronaviruses (CoVs) primarily cause enzootic infections in birds and mammals. In the last few decades, coronaviruses have shown to be capable of infecting humans as well. The outbreak of severe acute respiratory syndrome (SARS) in 2003, Middle-East respiratory syndrome (MERS) and, more recently, coronavirus disease 2019 (COVID-19) has demonstrated the lethality of CoVs when they cross the species barrier and infect humans. A renewed interest in coronaviral research spurred by the COVID-19 pandemic has led to a variety of new vaccines. However, there remains an urgent need for other approaches to treat, prevent and manage viral infections.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, Mol Biol. Cell. 2007, 18. 2698-2706). AAK1 is enriched in synaptosomal preparations and is co-localized with endocytic structures in cultured cells. AAK1 modulates clathrin coated endocytosis, a process that is important in synaptic vesicle recycling and receptor-mediated endocytosis. AAK1 associates with the AP2 complex, a hetero-tetramer which links receptor cargo to the clathrin coat. The binding of clathrin to AAK1 stimulates AAK1 kinase activity (Conner et. al., Traffic 2003. 4, 885-890; Jackson et. al. J. Cell. Biol. 2003, 163, 231-236). AAK1 phosphorylates the mu-2 subunit of AP-2, which promotes the binding of mu-2 to tyrosine containing sorting motifs on cargo receptors (Ricotta et. al., J. Cell Bio. 2002, 156, 791-795; Conner and Schmid. J. Cell Bio. 2002, 156, 921-929). Mu2 phosphorylation is not required for receptor uptake, but phosphorylation enhances the efficiency of internalization (Motely et al., Mol. Biol Cell. 2006, 17, 5298-5308). Recent efforts to develop AAK1 inhibitors have focused on their potential use to treat pain and some forms of mental illness. See, e.g., U.S. Pat. No. 9,902,722.

4. SUMMARY OF THE INVENTION

This invention is based on the discovery that certain AAK1 inhibitors antiviral activity and may be used to treat viral infections. Accordingly, one embodiment of the invention is a method comprising administering to a subject in need thereof a therapeutically effective amount of an adaptor associated kinase 1 (AAK1) inhibitor.

In some embodiments, the subject displays one or more of fever, cough, shortness of breath, difficulty breathing, persistent pain in the chest, pressure in the chest, bluish lips or face, tiredness, runny nose, or sore throat.

Also provided herein are methods of inhibiting entry, assembly and/or budding of a coronavirus in a host cell, the method comprising contacting the host cell with an AAK1 inhibitor.

In some embodiments, the coronavirus is severe acute respiratory syndrome coronavirus 2 (SARS-CoV-2). In some embodiments, the coronavirus is severe acute respiratory syndrome coronavirus (SARS-CoV). In some embodiments, the coronavirus is Middle East respiratory syndrome coronavirus (MERS-CoV).

In some embodiments, the coronavirus is SARS-CoV-2-like coronavirus. In some embodiments, the SARS-CoV-2-like coronavirus has at least 80, 90, 95, or 98 percent sequence identity with SEQ ID NO 1.

In some embodiments, the coronavirus is CoV-229E-like coronavirus. In some embodiments, the CoV-229E-like coronavirus has at least 80, 90, 95, or 98 percent sequence identity with SEQ ID NO 5.

In some embodiments, the coronavirus is CoV-OC43-like coronavirus. In some embodiments, the CoV-OC43-like coronavirus has at least 80, 90, 95, or 98 percent sequence identity with SEQ ID NO 9.

In some embodiments, the AAK1 inhibitor is a compound of Formula (I):

(I)

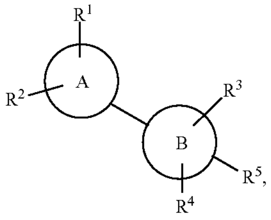

or a pharmaceutically acceptable salt thereof, wherein:

A is selected from

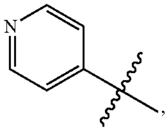,
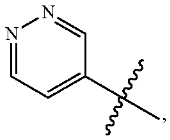,
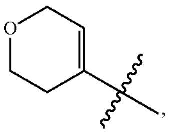,
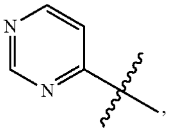,
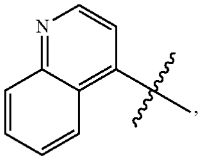,
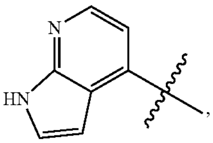,
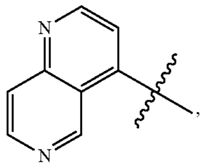, and
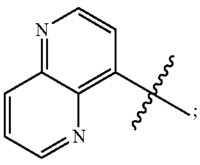;

wherein "" denotes the point of attachment to B;

B is selected from

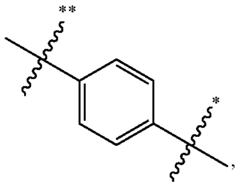
,
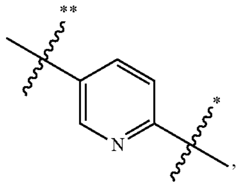
,
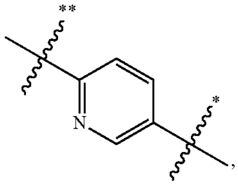
,
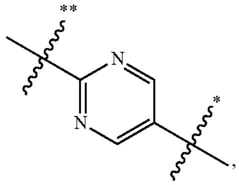
,
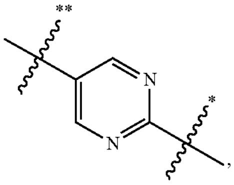
, and
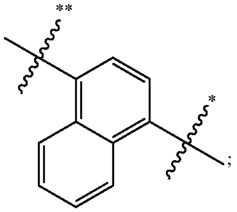
;

wherein “*” indicates the point of attachment to $R^5$ and “**” indicates the point of attachment to ring A;

$R^1$ is selected from hydrogen, amino, —$CO_2H$, difluoromethyl, ethyl, halo, hydroxymethyl, methoxy, methyl, —$NHC(O)CH_3$, —$NHCO_2CH_3$, trifluoromethoxy, and trifluoromethyl;

$R^2$ is selected from hydrogen, cyano, —$CH_2OH$, halo, and methyl;

$R^3$ is selected from hydrogen, cyano, cyclopropyl, difluoromethyl, halo, hydroxymethyl, methoxy, methyl, methylsulfonyl, trifluoromethoxy, trifluoromethyl, —$CH_2N(CH_3)_2$, and a five-membered aromatic ring containing one, two, or three heteroatoms selected from nitrogen, oxygen, and sulfur;

$R^4$ is selected from hydrogen, halo, and methyl;

$R^5$ is selected from

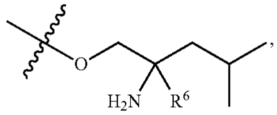
,
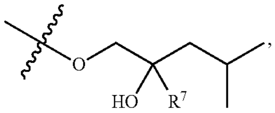
, and
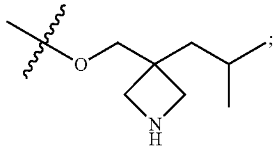
;

$R^6$ is selected from hydrogen, ethyl, fluoromethyl, difluoromethyl, methyl, and trifluoromethyl; and $R^7$ is methyl.

In some embodiments, the AAK1 inhibitor is a compound of Formula (II):

(II)

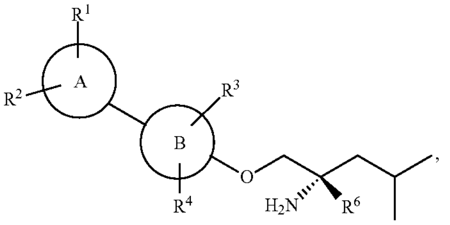
, or a pharmaceutically acceptable salt thereof, wherein:

A is selected from

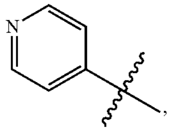
,
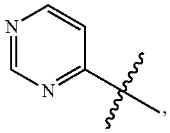
,
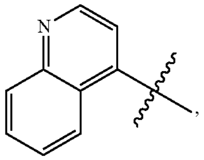
,
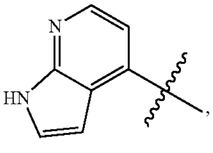
,
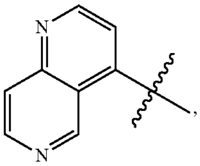
, and
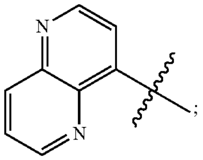
;

wherein “” denotes the point of attachment to B;

B is selected from phenyl and pyridinyl;

$R^1$ is selected from hydrogen, difluoromethyl, halo, methoxy, methyl, —$NHC(O)CH_3$, —$NHCO_2CH_3$, and trifluoromethyl;

$R^2$ is selected from hydrogen, —$CH_2OH$, and halo;

$R^3$ is selected from hydrogen, cyano, cyclopropyl, difluoromethyl, halo, hydroxymethyl, methoxy, methyl, trifluoromethoxy, trifluoromethyl, and a five-membered aromatic ring containing one, two, or three heteroatoms selected from nitrogen, oxygen, and sulfur;

$R^4$ is selected from hydrogen, halo, and methyl; and $R^6$ is selected from hydrogen, ethyl, fluoromethyl, difluoromethyl, methyl, and trifluoromethyl.

In some embodiments, A is

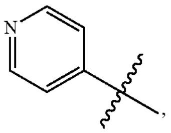
,
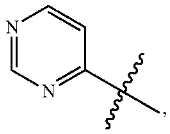
, and
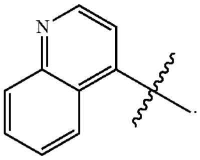
.

In some embodiments, B is

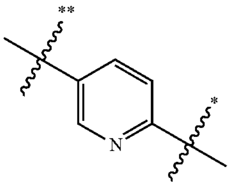

and

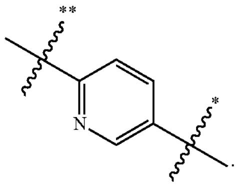

In some embodiments, $R^5$ is

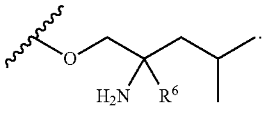

In some embodiments, the AAK1 inhibitor is (S)-1-((2',6-bis(difluoromethyl)-[2,4'-bipyridin]-5-yl)oxy)-2,4-dimethylpentan-2-amine:

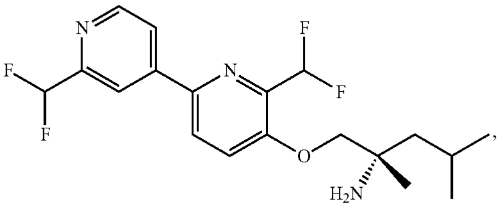 [SMILES: CC(C)C[C@](C)(N)COc1ccc(-c2ccnc(C(F)F)c2)nc1C(F)F]

or a pharmaceutically acceptable salt thereof (referred to herein as "Compound 1").

In some embodiments, the AAK1 inhibitor is administered to the subject in a pharmaceutical composition comprising the AAK1 inhibitor and a pharmaceutically acceptable carrier or excipient. In some embodiments, the pharmaceutical composition is in a pharmaceutical dosage form. In some embodiments, the administration is oral.

One embodiment of the invention is a method of treating, managing and/or preventing a SARS-CoV-2-like coronavirus infection which comprises administering to a subject in need thereof a therapeutically or prophylactically effective amount of Compound 1 or pharmaceutically acceptable salt thereof.

One embodiment of the invention is a method of treating, managing and/or preventing a CoV-229E-like coronavirus infection, the method comprising administering to a subject in need thereof a therapeutically or prophylactically effective amount of Compound 1 or a pharmaceutically acceptable salt thereof.

One embodiment of the invention is a method of treating, managing and/or preventing a CoV-OC43-like coronavirus infection, the method comprising administering to a subject in need thereof a therapeutically or prophylactically effective amount of Compound 1 or a pharmaceutically acceptable salt thereof.

In some embodiments, the AAK1 inhibitor is orally administered to the subject at a dose of about 50-500 mg. In some embodiments, the AAK1 inhibitor is orally administered to the subject at a dose of about 100-300 mg. In some embodiments, the AAK1 inhibitor is orally administered to the subject at a dose of about 150-250 mg. In some embodiments, the AAK1 inhibitor is orally administered to the subject at a dose of about 200 mg.

5. DESCRIPTION OF DRAWINGS

The following drawings form part of the present specification and are included to further demonstrate certain aspects of the invention. The invention may be better understood by reference to one or more of these drawings in combination with the detailed description of specific embodiments presented herein:

FIG. 1 shows some raw data obtained from testing the in vitro antiviral effect of the AAK1 inhibitor (S)-1-((2',6-bis(difluoromethyl)-[2,4'-bipyridin]-5-yl)oxy)-2,4-dimethylpentan-2-amine phosphate ("Compound 1") against CoV-229E.

FIG. 2 provides a graphical representation of data obtained from testing the in vitro antiviral effect of Compound 1 against CoV-229E.

FIG. 3 depicts the inhibition of HCoV-OC43-induced CPE (percentage values). Values show the inhibition of the HCoV-OC43 induced CPE, as a surrogate marker for virus replication.

FIG. 4 depicts the viability of Huh-7 cells in the presence of test-items (percentage values). Results show the extent of cell viability as determined by the XTT assay (absorbance 490 nm readout) at 6 days. Data is normalized to the values observed in cells in the absence of test-material (vehicle alone, medium only with 0.01% DMSO).

FIG. 5 depicts the determination of $CC_{50}$ values for test-items with Huh-7 cells (percentage values). Values indicate the percent viability estimated as percentage of that observed in samples incubated with vehicle alone (medium only with 0.01% DMSO). Results show the average of duplicate data points. Data was adjusted to a sigmoid function and $CC_{50}$ values were calculated using GraphPad Prism software fitting a normalized dose-response curve with a variable slope.

Figure 9:
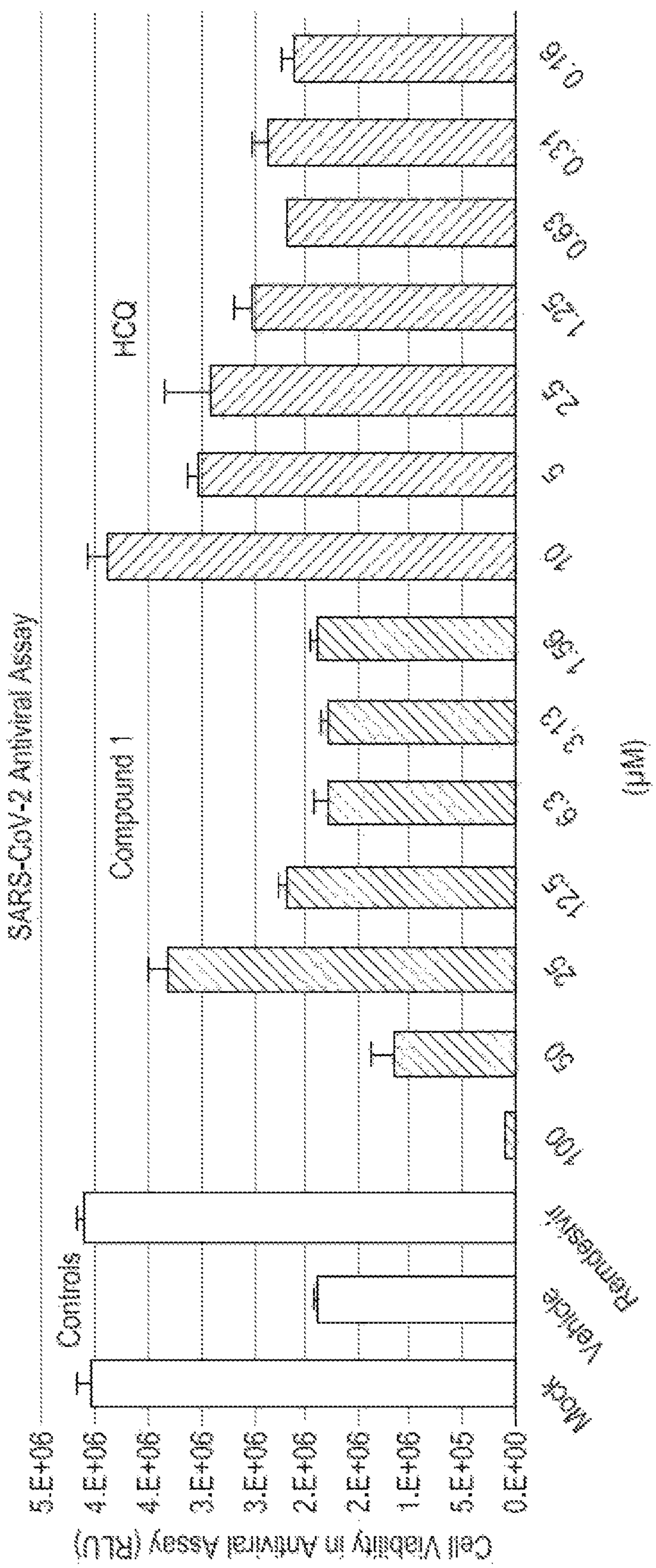

FIG. 9. depicts the inhibition of SARS-CoV-2 Induced CPE (raw RLU). Cell viability is shown as raw RLU values in wells containing Vero E6 cells infected in the presence of either vehicle alone or varying concentrations of test-items. Uninfected cells are shown as Mock. Remdesivir at 10 μM is also included as a positive control.

Figure 10:
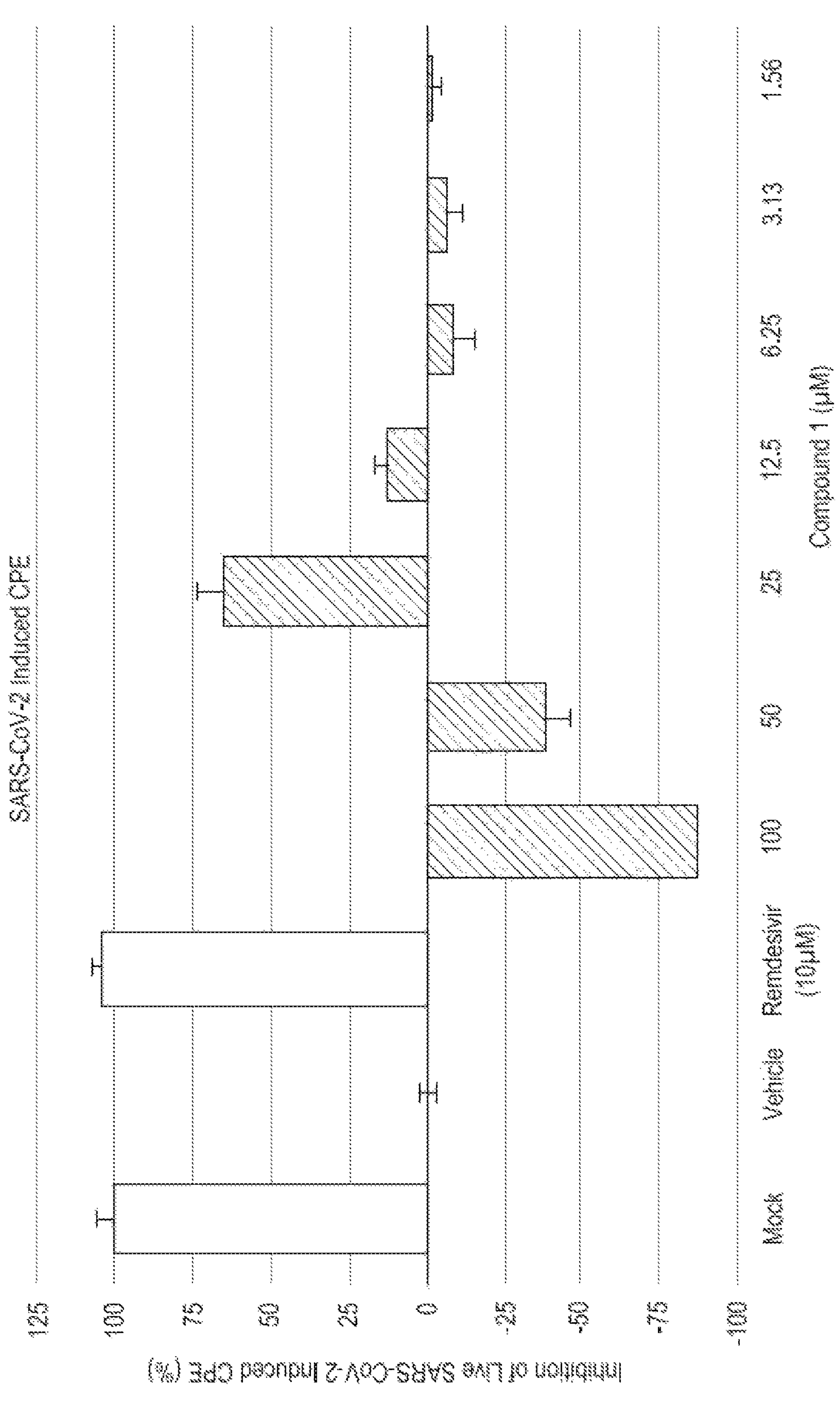

FIG. 10 depicts inhibition of live SARS-CoV-2 induced CPE (percentage values) by Compound 1. Values show the inhibition of the SARS-CoV-2 induced CPE, as a surrogate marker for virus replication. Data values were normalized to the RLU observed in uninfected cells after subtraction of the average luminescence observed in infected cells in the presence of vehicle. Values in uninfected cells ("mock") are included for comparison (100% inhibition). Data plotted for test-items shows the average and standard deviation of duplicates.

Figure 11:
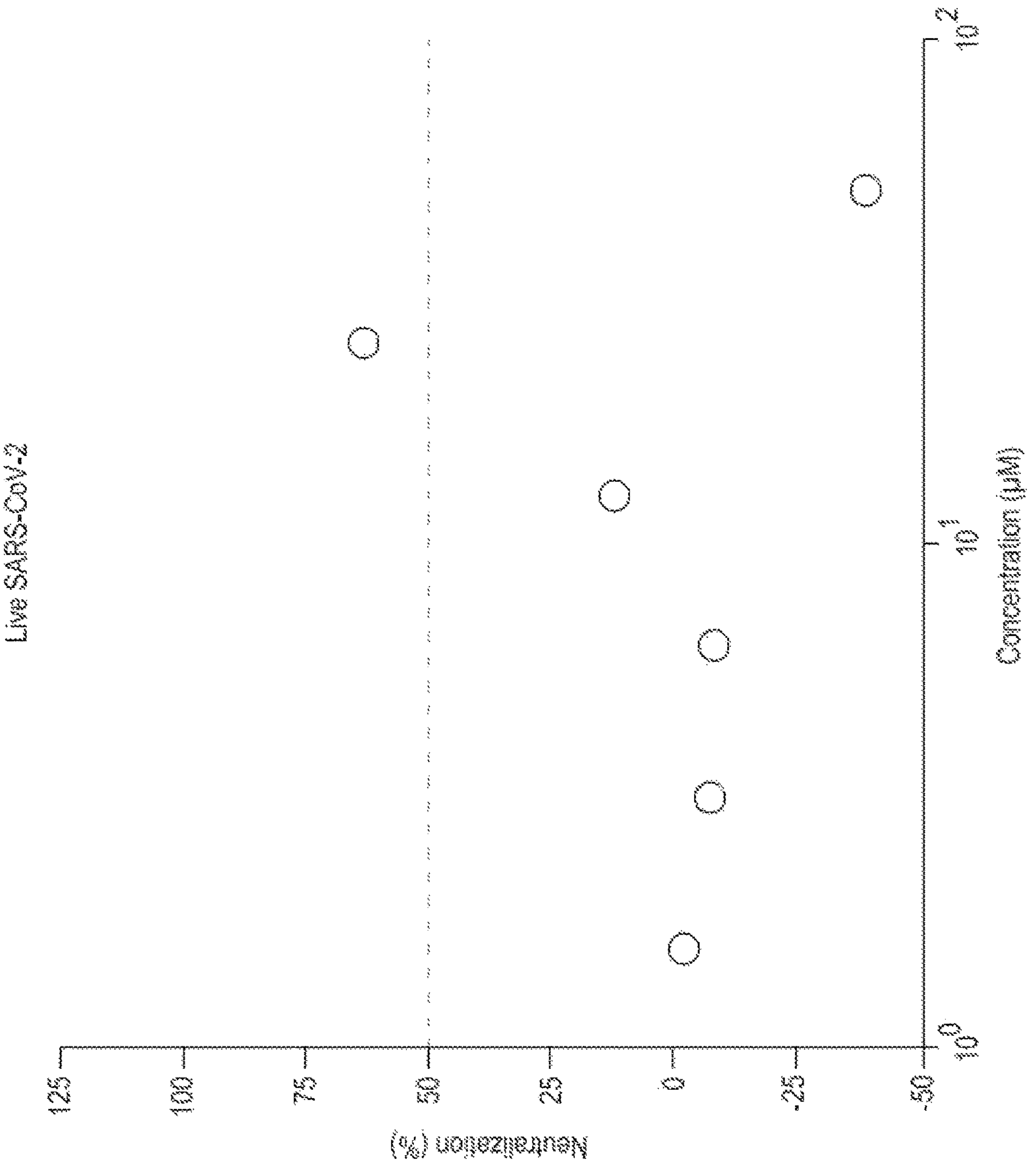

FIG. 11 shows the determination of $IC_{50}$ values for SARS-CoV-2 neutralization by Compound 1. Values indicate the percentage of live SARS-CoV-2 (USA-WA1/2020) inhibition as compared to samples incubated with no test-item (vehicle alone). Results show the average of duplicate data points for test-items. For data that failed to be adjusted to a sigmoidal function using GraphPad Prism software, approximated $IC_{50}$ values were extrapolated from the concentrations inhibiting SARS-CoV-2 replication by 50%.

Figure 12:
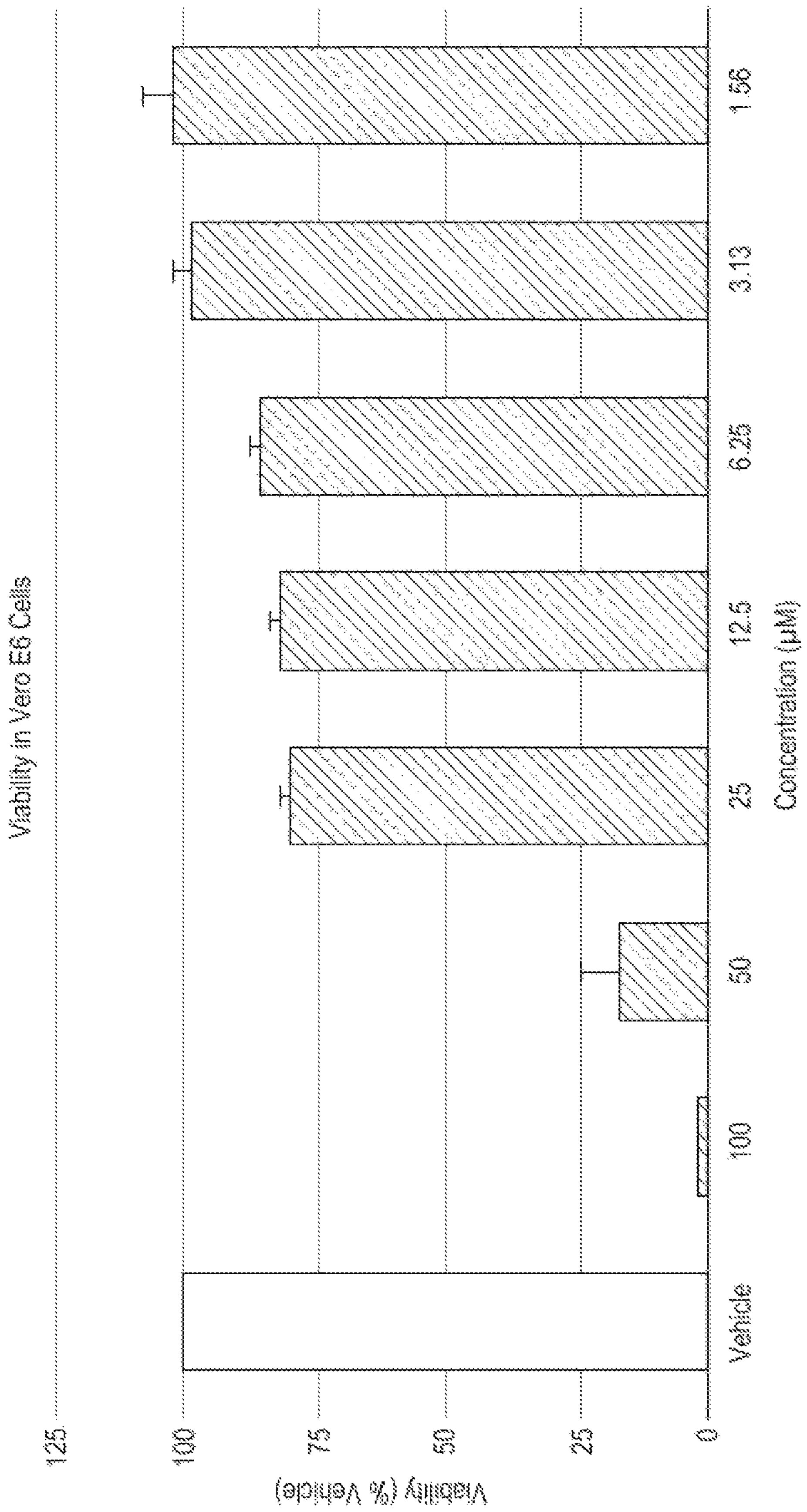

FIG. 12 depicts viability in uninfected Vero E6 cells (percentage values) by treatment of Compound 1. Results show the extent of cell viability as determined by the CellTiter Glo assay (RLU) after two days. Data is normalized to the values observed in cells in the absence of test-material ("vehicle"). Results show the average of duplicate data points with the standard deviation.

Figure 13:
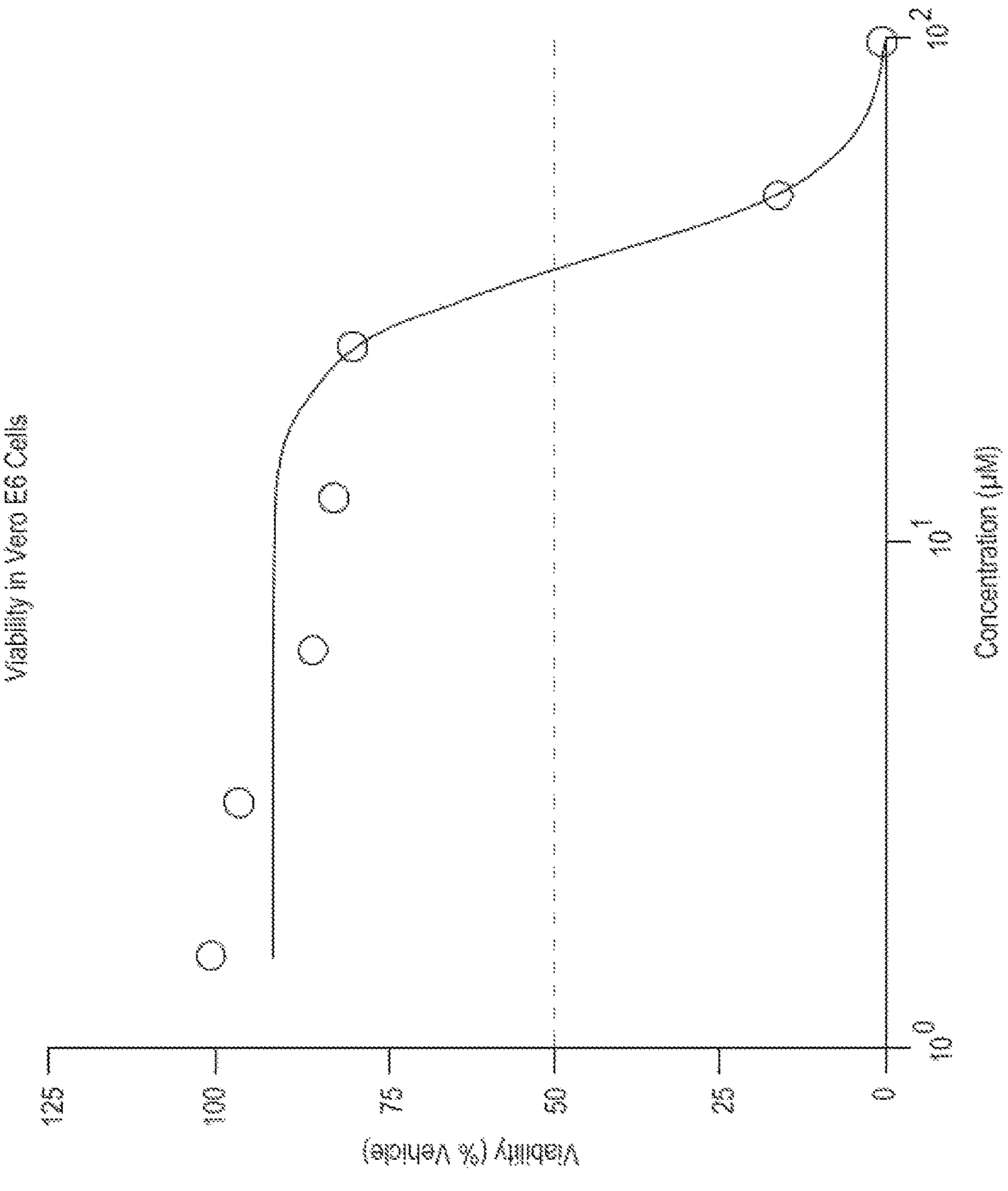

FIG. 13 shows the determination of $CC_{50}$ values for Compound 1 in Vero E6 cells (percentage values). Values indicate the percent viability estimated as percentage of that observed in samples incubated with vehicle alone (medium). Results show the average of duplicate data points. Data was adjusted to a sigmoid function when possible, and $CC_{50}$ values were calculated using GraphPad Prism software fitting a normalized dose-response curve with a variable slope.

Figure 14A:
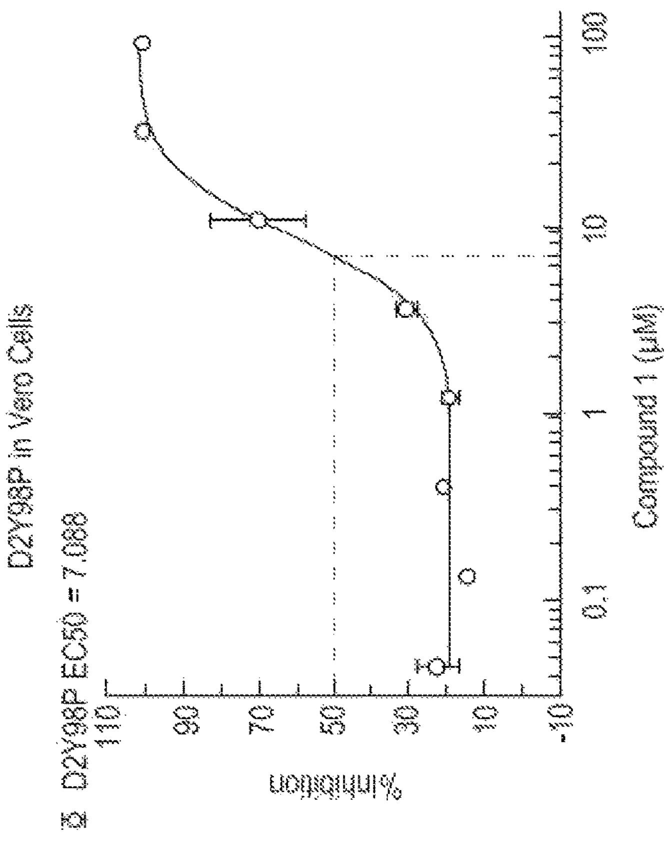
Figure 14B:
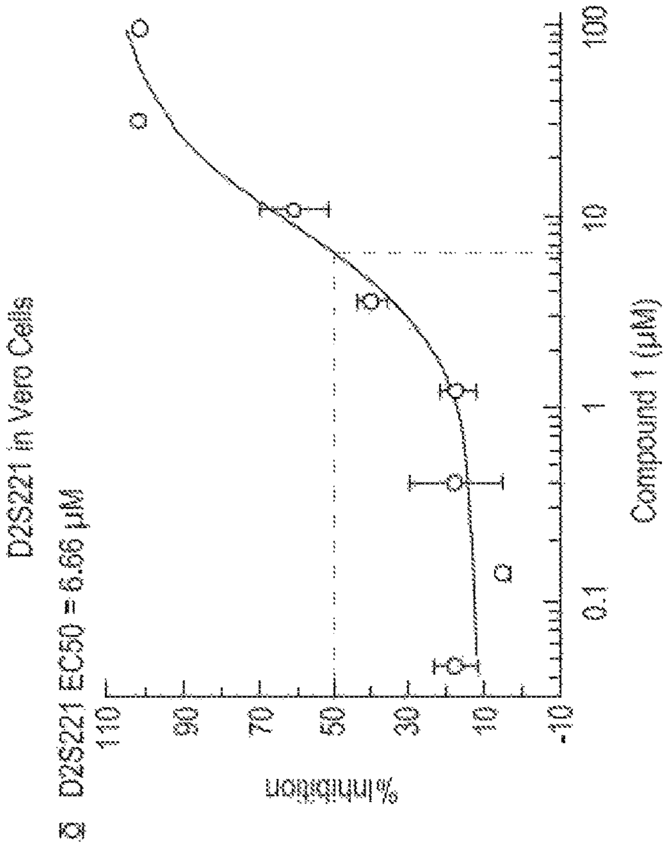

FIG. 14 depicts antiviral activity of Compound 1. FIG. 14A shows data from day 4; FIG. 14B shows data from day 5. Vero cells seeded in 96-well plates were incubated with serial dilutions of Compound 1 starting at 100 μM (eight 3-fold dilutions) and infected with D2Y98P and D2S221 at MOI 0.05 and 0.08, respectively. $IC_{50}$ values were calculated using XLfit model 205. The average values of triplicates for each experiment are shown with the standard deviation. Solid circles represent the average cytotoxicity of Compound 1 on the y-axis.

Figure 15A:
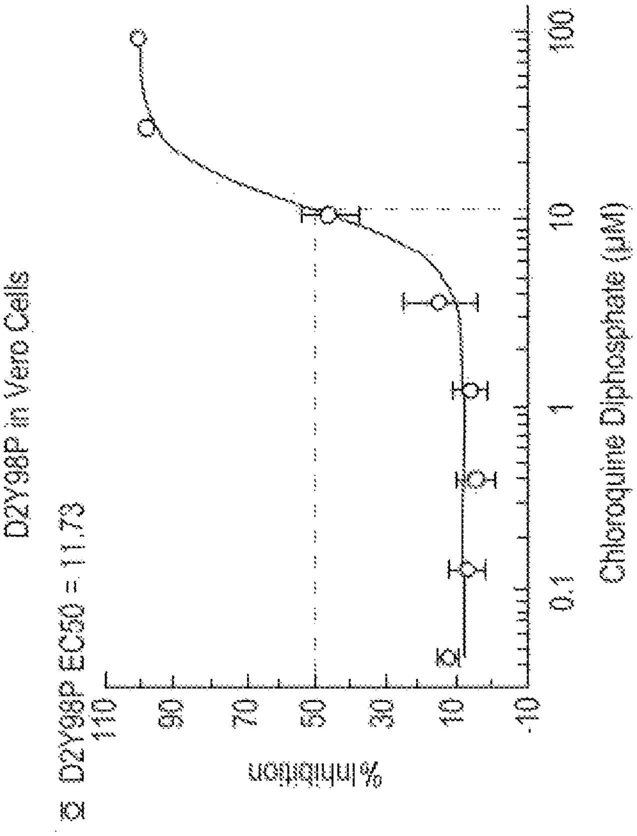
Figure 15B:
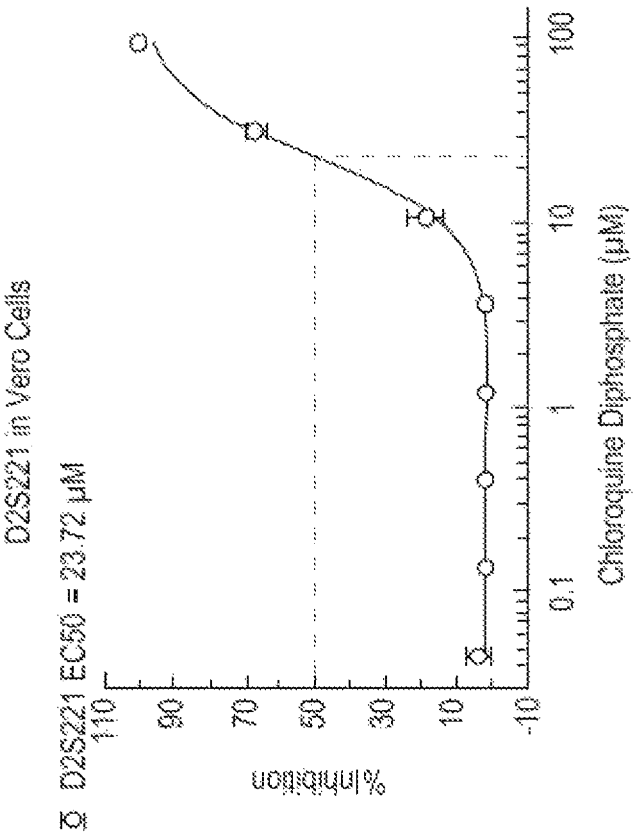

FIG. 15 depicts antiviral activity of chloroquine diphosphate. FIG. 15A shows data from day 4; FIG. 15B shows data from day 5. Vero cells seeded in 96-well plates were incubated with serial dilutions of chloroquine diphosphate starting at 100 μM (8 3-fold dilutions) and infected with D2Y98P and D2S221 at MOI 0.05 and 0.08, respectively. $IC_{50}$ values were calculated using XLfit model 205. The average values of triplicates for each experiment are shown with the standard deviation. Solid circles represent the average cytotoxicity of the chloroquine diphosphate on the y-axis.

Figure 16B:
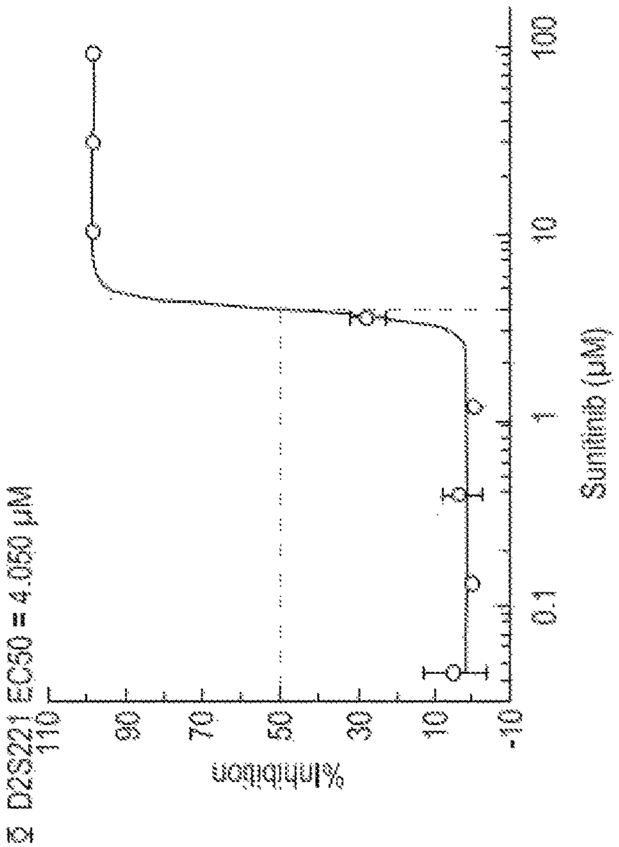
Figure 16A:
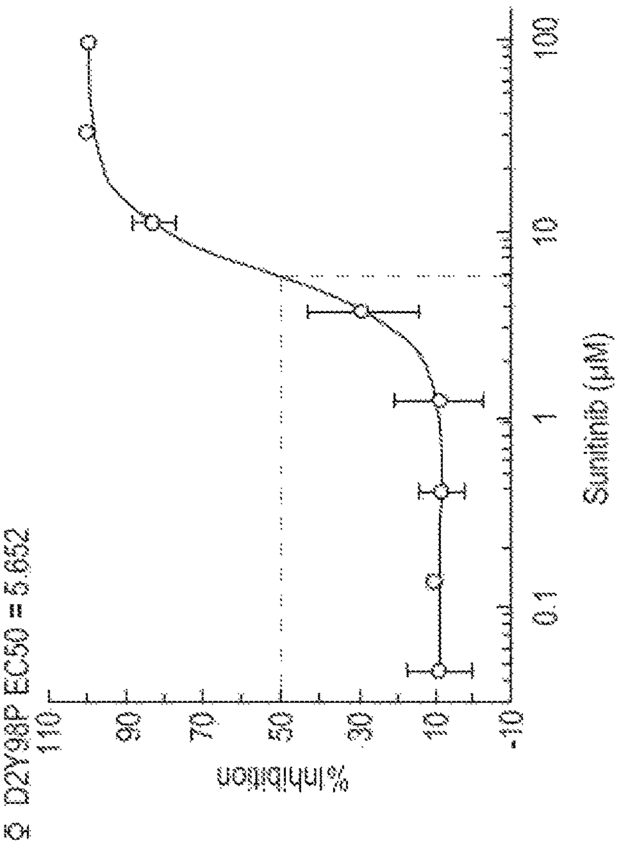

FIG. 16 depicts antiviral activity of sunitinib. FIG. 16A shows data from day 4; FIG. 16B shows data from day 5. Vero cells seeded in 96-well plates were incubated with serial dilutions of sunitinib starting at 100 μM (eight 3-fold dilutions) and infected with D2Y98P and D2S221 at MOI 0.05 and 0.08, respectively. $IC_{50}$ values were calculated using XLfit model 205. The average values of triplicates for each experiment are shown with the standard deviation. Solid circles represent the average cytotoxicity of sunitinib on the y-axis.

Figure 17B:
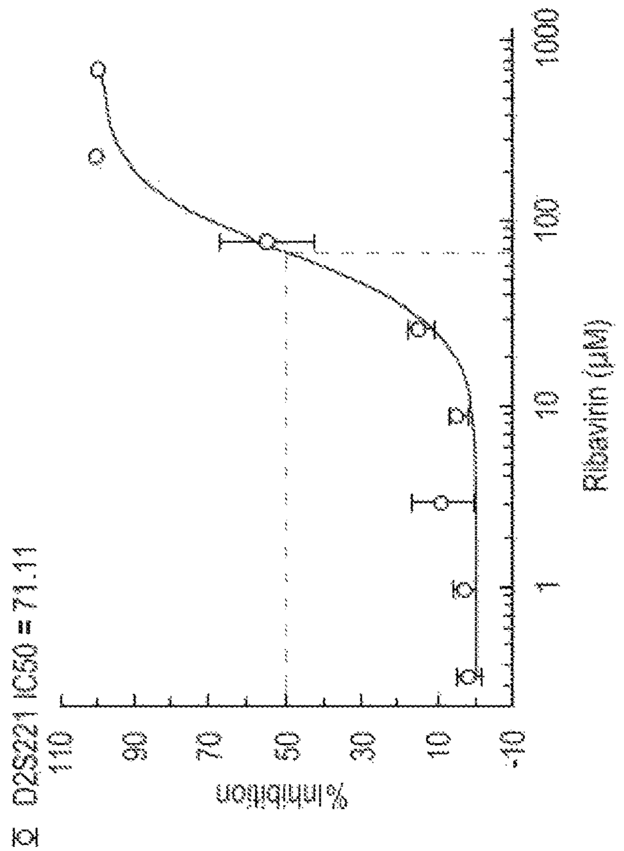
Figure 17A:
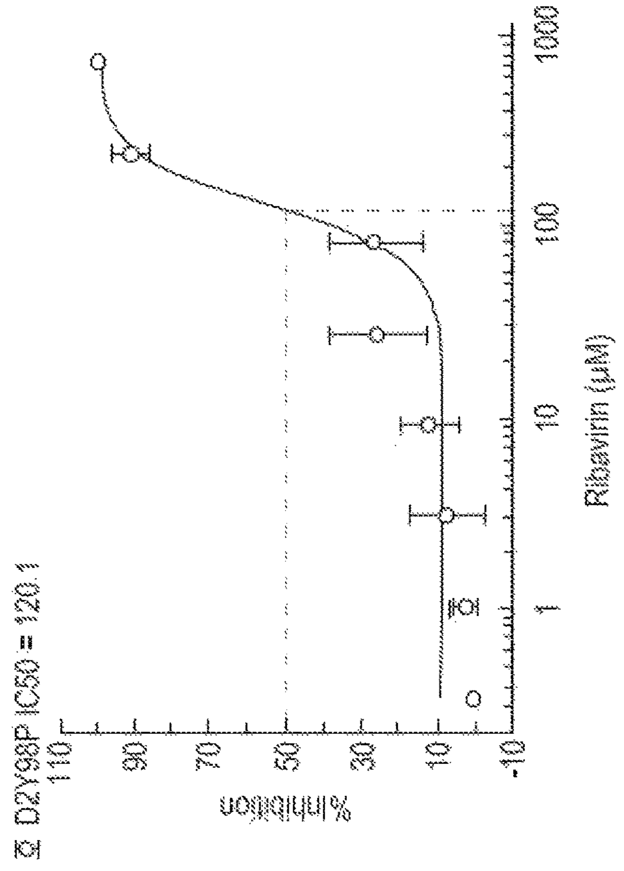

FIG. 17 depicts antiviral activity of ribavirin (internal assay control). FIG. 17A shows data from day 4; FIG. 17B shows data from day 5. Vero cells seeded in 96-well plates were incubated with serial dilutions of ribavirin starting at 100 μM (eight 3-fold dilutions) and infected with D2Y98P and D2S221 at MOI 0.05 and 0.08, respectively. $IC_{50}$ values were calculated using XLfit model 205. The average values of triplicates for each experiment are shown with the standard deviation. Solid circles represent the average cytotoxicity of ribavirin on the y-axis.

6. DETAILED DESCRIPTION OF THE INVENTION

This invention is based, in part, on the discovery that certain AAK1 inhibitors may be useful in treating, managing and/or preventing viral infections.

6.1. Definitions

In describing and claiming the disclosed subject matter, the following terminology will be used in accordance with the definitions set forth below.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A "prophylactically effective amount" of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

As used herein, the singular forms "a", "an", and "the" include plural reference unless the context clearly dictates otherwise.

Unless otherwise indicated, the term "about" is used herein to mean within the typical ranges of tolerances in the art. For example, "about" can be understood as about 2 standard deviations from the mean. In certain embodiments, about means ±10%. In certain embodiments, about means ±5%. When about is present before a series of numbers or a range, it is understood that "about" can modify each of the numbers in the series or range.

6.2. AAK1 Inhibitors

This invention encompasses methods of using and compositions comprising adaptor associated kinase 1 (A K1) inhibitors disclosed in U.S. Pat. No. 9,902,722. Particular compounds include those of formula (I):

(I)

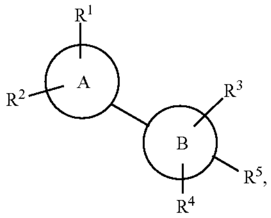

and pharmaceutically acceptable salts thereof, wherein:

A is selected from

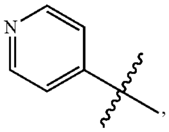, 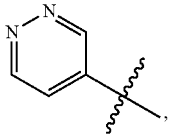, 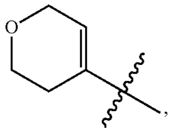,

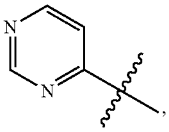, 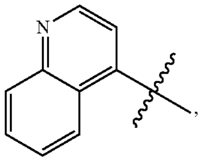,

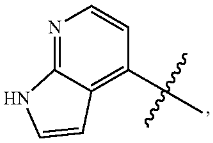, 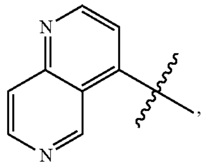, and

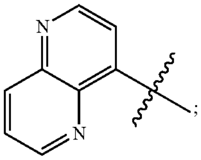;

wherein “” denotes the point of attachment to B;

B is selected from

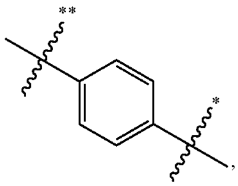, 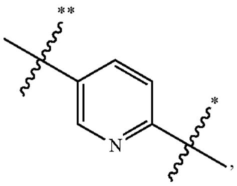,

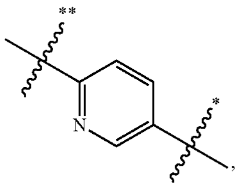, 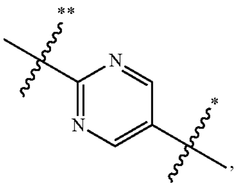,

-continued

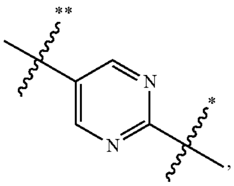, and 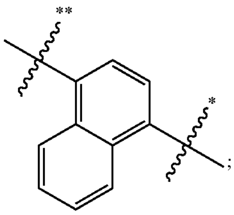;

wherein “*” indicates the point of attachment to $R^5$ and “**” indicates the point of attachment to ring A;

$R^1$ is selected from hydrogen, amino, —$CO_2H$, difluoromethyl, ethyl, halo, hydroxymethyl, methoxy, methyl, —$NHC(O)CH_3$, —$NHCO_2CH_3$, trifluoromethoxy, and trifluoromethyl;

$R^2$ is selected from hydrogen, cyano, —$CH_2OH$, halo, and methyl;

$R^3$ is selected from hydrogen, cyano, cyclopropyl, difluoromethyl, halo, hydroxymethyl, methoxy, methyl, methylsulfonyl, trifluoromethoxy, trifluoromethyl, —$CH_2N(CH_3)_2$, and a five-membered aromatic ring containing one, two, or three heteroatoms selected from nitrogen, oxygen, and sulfur;

$R^4$ is selected from hydrogen, halo, and methyl;

$R^5$ is selected from

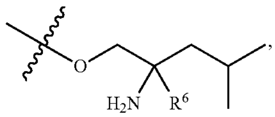,

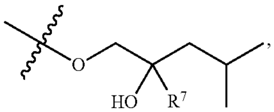, and

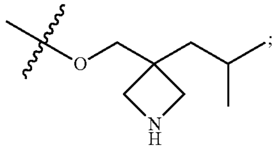;

$R^6$ is selected from hydrogen, ethyl, fluoromethyl, difluoromethyl, methyl, and trifluoromethyl; and $R^7$ is methyl.

In some embodiments of formula (I), A is selected from

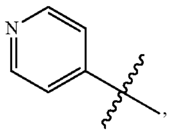, 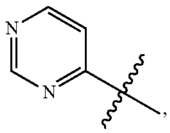, and

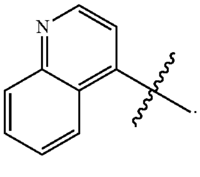.

In some embodiments of formula (I), B is selected from

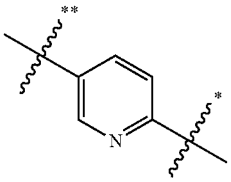
and
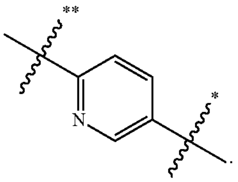
.

In some embodiments of formula (I), B is:

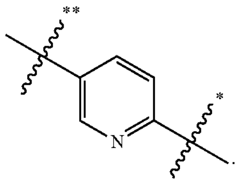 [SMILES: *c1ccc(*)nc1]
.

In some embodiments of formula (I), $R^5$ is

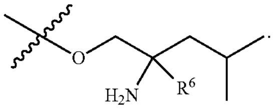
.

Particular AAK1 inhibitors include those of formula (II):

(II)

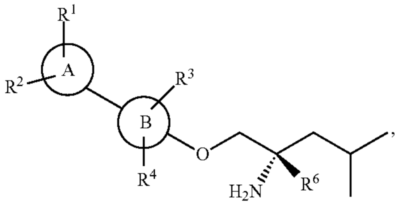
, and a pharmaceutically acceptable salts thereof, wherein:

A is selected from

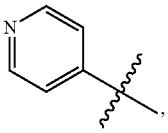
,
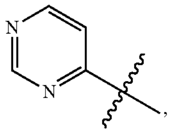
,
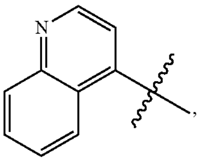
,
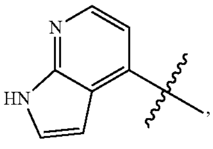
,

-continued

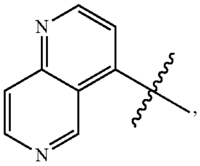
, and
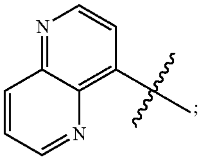
;

wherein “ ” denotes the point of attachment to B;

B is selected from phenyl and pyridinyl;

$R^1$ is selected from hydrogen, difluoromethyl, halo, methoxy, methyl, —NHC(O)$CH_3$, —$NHCO_2CH_3$, and trifluoromethyl;

$R^2$ is selected from hydrogen, —$CH_2OH$, and halo;

$R^3$ is selected from hydrogen, cyano, cyclopropyl, difluoromethyl, halo, hydroxymethyl, methoxy, methyl, trifluoromethoxy, trifluoromethyl, and a five-membered aromatic ring containing one, two, or three heteroatoms selected from nitrogen, oxygen, and sulfur;

$R^4$ is selected from hydrogen, halo, and methyl; and $R^5$ is selected from hydrogen, ethyl, fluoromethyl, difluoromethyl, methyl, and trifluoromethyl.

In some embodiments of formula (II), A is selected from

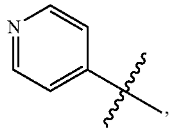
,
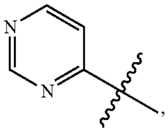
, and
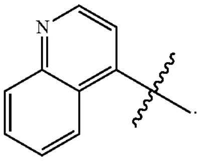
.

In some embodiments of formula (II), B is pyridinyl.

In some embodiments of formula (II), B is:

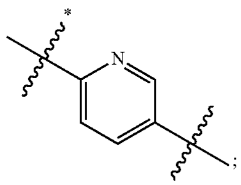 [SMILES: *c1ccc(*)nc1]
;

wherein “ ” denotes the point of attachment to A and “ ” denotes the point of attachment to the oxygen atom.

In some embodiments of formula (II), A is selected from

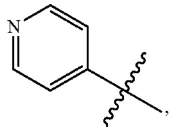
,
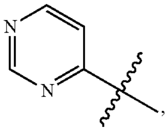
, and

-continued

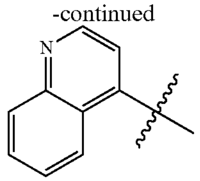

B is

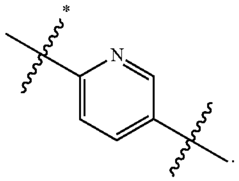 [SMILES: *c1ccc(*)nc1]

Specific AAK1 inhibitors include:
(S)—N-(4-(4-((2-amino-4-methylpentyl)oxy)-3-fluorophenyl)pyridin-2-yl)acetamide;
(S)—N-(4-(4-((2-amino-4-methylpentyl)oxy)-3-methoxyphenyl)pyridin-2-yl)acetamide;
(S)—N-(4-(4-((2-amino-4-methylpentyl)oxy)-3-cyanophenyl)pyridin-2-yl)acetamide;
(S)-2-((2-amino-4-methylpentyl)oxy)-5-(2-aminopyridin-4-yl)benzonitrile;
(S)—N-(4-(4-((2-amino-4-methylpentyl)oxy)-3-(trifluoromethyl)phenyl)pyridin-2-yl)acetamide;
(S)—N-(4-(4-((2-amino-4-methyl pentyl)oxy)-3-(trifluoromethoxy)phenyl)pyridin-2-yl)acetamide;
(S)—N-(4-(4-((2-amino-4-methylpentyl)oxy)-3-methylphenyl)pyridin-2-yl)acetamide;
(S)—N-(4-(4-((2-amino-4-methylpentyl)oxy)-3-chlorophenyl)pyridin-2-yl)acetamide;
(S)—N-(4-(4-((2-amino-4-methylpentyl)oxy)-3,5-difluorophenyl)pyridin-2-yl)acetamide;
(S)—N-(4-(4-((2-amino-4-methylpentyl)oxy)-3-chloro-5-fluorophenyl)pyridin-2-yl)acetamide;
(S)—N-(4-(4-((2-amino-4-methylpentyl)oxy)-3-fluoro-5-(trifluoromethyl)phenyl)pyridin-2-yl)acetamide;
(S)—N-(4-(4-((2-amino-4-methylpentyl)oxy)-2,5-difluorophenyl)pyridin-2-yl)acetamide;
(S)-methyl (4-(4-((2-amino-4-methylpentyl)oxy)-3-fluorophenyl)pyridin-2-yl)carbamate;
(S)-methyl (4-(4-((2-amino-4-methylpentyl)oxy)-3-(isoxazol-5-yl)phenyl)pyridin-2-yl)carbamate;
(S)-2-((2-amino-4-methylpentyl)oxy)-5-(2-methylpyridin-4-yl)benzonitrile;
(S)-2-((2-amino-4-methylpentyl)oxy)-5-(2-methoxypyridin-4-yl)benzonitrile;
(S)-2-((2-amino-4-methylpentyl)oxy)-5-(2-(trifluoromethyl)pyridin-4-yl)benzonitrile;
(S)-1-(2-(isoxazol-5-yl)-4-(2-methylpyridin-4-yl)phenoxy)-4-methylpentan-2-amine;
(S)—N-(4-(4-((2-amino-2,4-dimethylpentyl)oxy)-3-(trifluoromethyl)phenyl)pyridin-2-yl)acetamide;
(S)-methyl (4-(4-((2-amino-2,4-dimethylpentyl)oxy)-3-(trifluoromethyl)phenyl)pyridin-2-yl)carbamate;
(S)—N-(4-(4-((2-amino-2,4-dimethylpentyl)oxy)-3-cyanophenyl)pyridin-2-yl)acetamide;
(S)-methyl (4-(4-((2-amino-2,4-dimethylpentyl)oxy)-3-cyanophenyl)pyridin-2-yl)carbamate;
(S)—N-(4-(4-((2-amino-2,4-dimethylpentyl)oxy)-3-(difluoromethyl)phenyl)pyridin-2-yl)acetamide;
(S)-methyl (4-(4-((2-amino-2,4-dimethylpentyl)oxy)-3-(difluoromethyl)phenyl)pyridin-2-yl)carbamate;
(S)—N-(4-(4-((2-amino-2,4-dimethylpentyl)oxy)-3-(trifluoromethoxy)phenyl)pyridin-2-yl)acetamide;
(S)-methyl (4-(4-((2-amino-2,4-dimethylpentyl)oxy)-3-(trifluoromethoxy)phenyl)pyridin-2-yl)carbamate;
(S)—N-(4-(4-((2-amino-2,4-dimethylpentyl)oxy)-3-fluorophenyl)pyridin-2-yl)acetamide;
(S)-methyl (4-(4-((2-amino-2,4-dimethylpentyl)oxy)-3-fluorophenyl)pyridin-2-yl)carbamate;
methyl (4-(4-((2-amino-2,4-dimethylpentyl)oxy)-3-chlorophenyl)pyridin-2-yl)carbamate;
methyl (4-(4-((2-amino-2,4-dimethylpentyl)oxy)-3-methylphenyl)pyridin-2-yl)carbamate;
methyl (4-(4-((2-amino-2,4-dimethylpentyl)oxy)-2,3-dimethylphenyl)pyridin-2-yl)carbamate;
(S)-methyl (4-(4-((2-amino-2,4-dimethylpentyl)oxy)-3-(hydroxymethyl)phenyl)pyridin-2-yl)carbamate;
(S)-methyl (4-(4-((2-amino-2,4-dimethylpentyl)oxy)-3-cyclopropylphenyl)pyridin-2-yl)carbamate;
(S)—N-(4-(4-((2-amino-2,4-dimethylpentyl)oxy)-3-(trifluoromethyl)phenyl)-5-(hydroxymethyl)pyridin-2-yl)acetamide;
(S)-1-(4-(2-(difluoromethyl)pyridin-4-yl)-2-(trifluoromethyl)phenoxy)-2,4-dimethylpentan-2-amine;
(S)-2-((2-amino-2,4-dimethylpentyl)oxy)-5-(2-(difluoromethyl)pyridin-4-yl)benzonitrile;
(S)-1-(2-(difluoromethyl)-4-(2-(difluoromethyl)pyridin-4-yl)phenoxy)-2,4-dimethylpentan-2-amine;
(S)-1-(4-(2-(difluoromethyl)pyridin-4-yl)-2-(trifluoromethoxy)phenoxy)-2,4-dimethylpentan-2-amine;
(S)-1-(4-(3-chloro-2-fluoropyridin-4-yl)-2-(trifluoromethyl)phenoxy)-2,4-dimethylpentan-2-amine;
(S)-1-(4-(5-chloro-2-fluoropyridin-4-yl)-2-(trifluoromethyl)phenoxy)-2,4-dimethylpentan-2-amine;
(S)-1-(4-(2-fluoro-3-methyl pyridin-4-yl)-2-(trifluoromethyl)phenoxy)-2,4-dimethylpentan-2-amine;
(S)-1-(4-(2,3-difluoropyridin-4-yl)-2-(trifluoromethyl)phenoxy)-2,4-dimethylpentan-2-amine;
(S)-2,4-dimethyl-1-(4-(pyridin-4-yl)-2-(trifluoromethyl)phenoxy)pentan-2-amine;
(S)-1-(4-(2-fluoropyridin-4-yl)-2-(trifluoromethyl)phenoxy)-2,4-dimethylpentan-2-amine;
(S)-2,4-dimethyl-1-(4-(2-methylpyridin-4-yl)-2-(trifluoromethyl)phenoxy)pentan-2-amine;
(S)-1-(4-(3-methoxypyridin-4-yl)-2-(trifluoromethyl)phenoxy)-2,4-dimethylpentan-2-amine;
(S)-1-(4-(3-fluoropyridin-4-yl)-2-(trifluoromethyl)phenoxy)-2,4-dimethylpentan-2-amine;
(S)-2-((2-amino-2,4-dimethylpentyl)oxy)-5-(2-methylpyridin-4-yl)benzonitrile;
(S)-1-(2-cyclopropyl-4-(2-methylpyridin-4-yl)phenoxy)-2,4-dimethylpentan-2-amine;
(S)-1-(2-(difluoromethyl)-4-(2-methylpyridin-4-yl)phenoxy)-2,4-dimethylpentan-2-amine;
methyl (6-((2-amino-2,4-dimethylpentyl)oxy)-[3,4'-bipyridin]-2'-yl)carbamate;
(S)-methyl (6-((2-amino-2,4-dimethylpentyl)oxy)-5-methyl-[3,4'-bipyridin]-2'-yl)carbamate;
(S)-methyl (6-((2-amino-2,4-dimethylpentyl)oxy)-5-cyano-[3,4'-bipyridin]-2'-yl)carbamate;
(S)-methyl (6-((2-amino-2,4-dimethylpentyl)oxy)-4-methyl-[3,4'-bipyridin]-2'-yl)carbamate;
(S)-methyl (6-((2-amino-2,4-dimethylpentyl)oxy)-5-chloro-[3,4'-bipyridin]-2'-yl)carbamate;
(S)-methyl (6-((2-amino-2,4-dimethylpentyl)oxy)-5-methoxy-[3,4'-bipyridin]-2'-yl)carbamate;

(S)-1-((2'-chloro-5-methyl-[3,4'-bipyridin]-6-yl)oxy)-2,4-dimethylpentan-2-amine;
(S)-1-((2'-(difluoromethyl)-5-methyl-[3,4'-bipyridin]-6-yl)oxy)-2,4-dimethylpentan-2-amine;
(S)-64(2-amino-2,4-dimethylpentyl)oxy)-2'-(difluoromethyl)-[3,4'-bipyridine]-5-carbonitrile;
(S)-1-((5-chloro-2'-methyl-[3,4'-bipyridin]-6-yl)oxy)-2,4-dimethylpentan-2-amine;
(S)-1-((2',5-dimethyl-[3,4'-bipyridin]-6-yl)oxy)-2,4-dimethylpentan-2-amine;
(S)-1-((5-methoxy-Z-methyl-[3,4'-bipyridin]-6-yl)oxy)-2,4-dimethylpentan-2-amine;
methyl (5-((2-amino-2,4-dimethylpentyl)oxy)-[2,4'-bipyridin]-2'-yl)carbamate;
(S)-methyl (5-((2-amino-2,4-dimethylpentyl)oxy)-6-methyl-[2,4'-bipyridin]-2'-yl)carbamate;
(S)-1-((2',6-dimethyl-[2,4'-bipyridin]-5-yl)oxy)-2,4-dimethylpentan-2-amine;
(S)-methyl (5-((2-amino-2,4-dimethylpentyl)oxy)-6-chloro-[2,4'-bipyridin]-2'-yl)carbamate;
(S)-1-((6-chloro-Z-methyl-[2,4'-bipyridin]-5-yl)oxy)-2,4-dimethylpentan-2-amine;
(S)-methyl (5-((2-amino-2,4-dimethylpentyl)oxy)-4-methyl-[2,4'-bipyridin]-2'-yl)carbamate;
(S)-2,4-dimethyl-1-(4-(quinolin-4-yl)-2-(trifluoromethyl)phenoxy)pentan-2-amine;
(S)-2,4-dimethyl-1-(2-(trifluoromethyl)-4-(7-(trifluoromethyl)quinolin-4-yl)phenoxy)pentan-2-amine;
(S)-1-(4-(7-fluoroquinolin-4-yl)-2-(trifluoromethyl)phenoxy)-2,4-dimethylpentan-2-amine;
(S)-1-(4-(5,7-difluoroquinolin-4-yl)-2-(trifluoromethyl)phenoxy)-2,4-dimethylpentan-2-amine;
(S)-1-(4-(6-fluoroquinolin-4-yl)-2-(trifluoromethyl)phenoxy)-2,4-dimethylpentan-2-amine;
(S)-1-(2-cyclopropyl-4-(quinolin-4-yl)phenoxy)-2,4-dimethylpentan-2-amine;
1-(2-chloro-6-fluoro-4-(quinolin-4-yl)phenoxy)-2,4-dimethylpentan-2-amine;
(S)-1-((5-(7-fluoroquinolin-4-yl)-3-methylpyridin-2-yl)oxy)-2,4-dimethylpentan-2-amine;
(S)-2-((2-amino-2,4-dimethylpentyl)oxy)-5-(5,7-difluoroquinolin-4-yl)nicotinonitrile;
(S)-1-((3-chloro-5-(quinolin-4-yl)pyridin-2-yl)oxy)-2,4-dimethylpentan-2-amine;
(S)-1-((3-methoxy-5-(quinolin-4-yl)pyridin-2-yl)oxy)-2,4-dimethylpentan-2-amine;
(S)-2-((2-amino-2,4-dimethylpentyl)oxy)-5-(1,6-naphthyridin-4-yl)nicotinonitrile;
(S)-2,4-dimethyl-1-((2-methyl-6-(quinolin-4-yl)pyridin-3-yl)oxy)pentan-2-amine;
(S)-2,4-dimethyl-1-((4-methyl-6-(quinolin-4-yl)pyridin-3-yl)oxy)pentan-2-amine;
(S)-1-((2-chloro-6-(quinolin-4-yl)pyridin-3-yl)oxy)-2,4-dimethylpentan-2-amine;
(S)-1-(4-(1H-pyrrolo[2,3-b]pyridin-4-yl)-2-(trifluoromethyl)phenoxy)-2,4-dimethylpentan amine;
(S)-1-(4-(1,6-naphthyridin-4-yl)-2-(trifluoromethyl)phenoxy)-2,4-dimethylpentan-2-amine;
(S)-2-((2-amino-2,4-dimethylpentyl)oxy)-5-(1,6-naphthyridin-4-yl)benzonitrile;
(S)-2-((2-amino-2,4-dimethylpentyl)oxy)-5-(1,5-naphthyridin-4-yl)benzonitrile;
(S)-1-(4-(7-chloroquinolin-4-yl)-2-(trifluoromethyl)phenoxy)-2,4-dimethylpentan-2-amine;
(S)-4-(4-((2-amino-2,4-dimethylpentyl)oxy)-3-(trifluoromethyl)phenyl)quinoline-7-carbonitrile;
(S)-2,4-dimethyl-1-(2-methyl-4-(2-methylpyridin-4-yl)phenoxy)pentan-2-amine;
(S)-1-(2-fluoro-4-(2-methylpyridin-4-yl)phenoxy)-2,4-dimethylpentan-2-amine;
(S)-1-(4-(2-fluoropyridin-4-yl)-2-methylphenoxy)-2,4-dimethylpentan-2-amine;
(S)-1-(2-fluoro-4-(2-fluoropyridin-4-yl)phenoxy)-2,4-dimethylpentan-2-amine;
(S)-2-((2-amino-2,4-dimethylpentyl)oxy)-5-(2-fluoropyridin-4-yl)benzonitrile;
(S)-1-((2'-fluoro-5-methyl-[3,4'-bipyridin]-6-yl)oxy)-2,4-dimethylpentan-2-amine;
(S)-4-(6-((2-amino-2,4-dimethylpentyl)oxy)-5-methylpyridin-3-yl)quinoline-7-carbonitrile;
(S)-1-((5-fluoro-Z-methyl-[3,4'-bipyridin]-6-yl)oxy)-2,4-dimethylpentan-2-amine;
(S)-1-((3-fluoro-5-(quinolin-4-yl)pyridin-2-yl)oxy)-2,4-dimethylpentan-2-amine;
(S)-4-(6-((2-amino-2,4-dimethylpentyl)oxy)-5-fluoropyridin-3-yl)quinoline-7-carbonitrile;
(S)-methyl (4-(4-((2-amino-2,4-dimethylpentyl)oxy)-3-cyanophenyl)-3-fluoropyridin-2-yl)carbamate;
(S)-64(2-amino-2,4-dimethylpentyl)oxy)-2'-methyl-[3,4'-bipyridine]-5-carbonitrile;
(S)-2-((2-amino-2,4-dimethylpentyl)oxy)-5-(7-methylquinolin-4-yl)benzonitrile;
(S)-2-((2-amino-2,4-dimethylpentyl)oxy)-5-(3-fluoro-2-methylpyridin-4-yl)benzonitrile;
(S)-2-((2-amino-2,4-dimethylpentyl)oxy)-5-(quinolin-4-yl)benzonitrile;
(S)-2-((2-amino-2,4-dimethylpentyl)oxy)-5-(5-fluoro-2-methylpyridin-4-yl)benzonitrile;
(S)-methyl (4-(4-((2-amino-2,4-dimethylpentyl)oxy)-3-cyanophenyl)-5-fluoropyridin-2-yl)carbamate;
(S)-1-((6-fluoro-2',4-dimethyl-[2,4'-bipyridin]-5-yl)oxy)-2,4-dimethylpentan-2-amine;
methyl (5-((3-isobutylazetidin-3-yl)methoxy)-6-methyl-[2,4'-bipyridin]-2'-yl)carbamate;
(S)-2-((2-amino-4-methylpentyl)oxy)-5-(6-methylpyridazin-4-yl)benzonitrile;
(S)-1-(2-(isoxazol-5-yl)-4-(quinolin-4-yl)phenoxy)-4-methylpentan-2-amine;
(S)-4-(4-((2-amino-2,4-dimethylpentyl)oxy)-3-(trifluoromethyl)phenyl)-2-methylnicotinic acid;
(S)-methyl (4-(4-((2-amino-2,4-dimethylpentyl)oxy)-3-((dimethylamino)methyl)phenyl)pyridin-2-yl)carbamate;
(S)-methyl (4-(4-((2-amino-2,4-dimethylpentyl)oxy)-3-(methylsulfonyl)phenyl)pyridin-2-yl)carbamate;
(S)-2,4-dimethyl-1-(4-(2-methylpyridin-4-yl)-2-(methylsulfonyl)phenoxy)pentan-2-amine;
(S)-2,4-dimethyl-1-(2-(methylsulfonyl)-4-(quinolin-4-yl)phenoxy)pentan-2-amine;
(S)-1-(2-(difluoromethyl)-4-(6-fluoroquinolin-4-yl)phenoxy)-2,4-dimethylpentan-2-amine;
(S)-methyl (5-((2-amino-2,4-dimethylpentyl)oxy)-6-(difluoromethyl)-[2,4'-bipyridin]-2'-yl)carbamate;
(S)-1-((2-(difluoromethyl)-6-(quinolin-4-yl)pyridin-3-yl)oxy)-2,4-dimethylpentan-2-amine;
(S)-1-((6-(difluoromethyl)-2'-methyl-[2,4'-bipyridin]-5-yl)oxy)-2,4-dimethylpentan-2-amine;
(S)-methyl (5-((2-amino-2,4-dimethylpentyl)oxy)-4-(difluoromethyl)-[2,4'-bipyridin]-2'-yl)carbamate;
(S)-1-((4-(difluoromethyl)-6-(quinolin-4-yl)pyridin-3-yl)oxy)-2,4-dimethylpentan-2-amine;
(S)-1-((4-(difluoromethyl)-2'-methyl-[2,4'-bipyridin]-5-yl)oxy)-2,4-dimethylpentan-2-amine;

(S)-1-((2',6-bis(difluoromethyl)-[2,4'-bipyridin]-5-yl)oxy)-2,4-dimethylpentan-2-amine;
(S)-1-((2',4-bis(difluoromethyl)-[2,4'-bipyridin]-5-yl)oxy)-2,4-dimethylpentan-2-amine;
(S)-1-((2'-(difluoromethyl)-4-methyl-[2,4'-bipyridin]-5-yl)oxy)-2,4-dimethylpentan-2-amine;
(S)-1-(2-cyclopropyl-4-(2-(difluoromethyl)pyridin-4-yl)phenoxy)-2,4-dimethylpentan-2-amine;
(S)-1-((2-(difluoromethyl)-6-(6-fluoroquinolin-4-yl)pyridin-3-yl)oxy)-2,4-dimethylpentan-2-amine;
(S)-1-((2-(difluoromethyl)-6-(7-fluoroquinolin-4-yl)pyridin-3-yl)oxy)-2,4-dimethylpentan-2-amine;
(S)-1-((2-(difluoromethyl)-6-(5,7-difluoroquinolin-4-yl)pyridin-3-yl)oxy)-2,4-dimethylpentan-2-amine;
(S)-1-((4-(difluoromethyl)-6-(5,7-difluoroquinolin-4-yl)pyridin-3-yl)oxy)-2,4-dimethylpentan-2-amine;
(S)-1-((4-(difluoromethyl)-6-(7-fluoroquinolin-4-yl)pyridin-3-yl)oxy)-2,4-dimethylpentan-2-amine;
(S)-1-((4-(difluoromethyl)-6-(6-fluoroquinolin-4-yl)pyridin-3-yl)oxy)-2,4-dimethylpentan-2-amine;
((S)-1-((4-(difluoromethyl)-6-(6-(trifluoromethyl)quinolin-4-yl)pyridin-3-yl)oxy)-2,4-dimethylpentan-2-amine;
(S)-1-((4-(difluoromethyl)-6-(6-(trifluoromethoxy)quinolin-4-yl)pyridin-3-yl)oxy)-2,4-dimethylpentan-2-amine;
(S)-1-((2-chloro-6-(5,7-difluoroquinolin-4-yl)pyridin-3-yl)oxy)-2,4-dimethylpentan-2-amine;
(S)-1-((2-chloro-6-(7-fluoroquinolin-4-yl)pyridin-3-yl)oxy)-2,4-dimethylpentan-2-amine;
(S)-1-((6-(7-fluoroquinolin-4-yl)-2-methylpyridin-3-yl)oxy)-2,4-dimethylpentan-2-amine;
(S)-1-((6-(6-fluoroquinolin-4-yl)-2-methylpyridin-3-yl)oxy)-2,4-dimethylpentan-2-amine;
(S)-1-((2-(difluoromethyl)-6-(2-methylpyrimidin-4-yl)pyridin-3-yl)oxy)-2,4-dimethylpentan-2-amine;
(S)-1-((2-(difluoromethyl)-6-(6-methylpyrimidin-4-yl)pyridin-3-yl)oxy)-2,4-dimethylpentan-2-amine;
(S)-1-((4-(difluoromethyl)-2'-ethyl-[2,4'-bipyridin]-5-yl)oxy)-2,4-dimethylpentan-2-amine;
(S)-1-((2'-chloro-4-(difluoromethyl)-3'-fluoro-[2,4'-bipyridin]-5-yl)oxy)-2,4-dimethylpentan-2-amine;
(S)-1-((2'-chloro-4-(difluoromethyl)-5'-fluoro-[2,4'-bipyridin]-5-yl)oxy)-2,4-dimethylpentan amine;
(S)-2,4-dimethyl-1-((2'-methyl-4-(trifluoromethyl)[2,4'-bipyridin]-5-yl)oxy)pentan-2-amine;
(S)-2,4-dimethyl-1-((6-(quinolin-4-yl)-4-(trifluoromethyl)pyridin-3-yl)oxy)pentan-2-amine;
(S)-methyl (5-((2-amino-2,4-dimethylpentyl)oxy)-4-(trifluoromethyl)-[2,4'-bipyridin]-2'-yl)carbamate;
(S)-1-((2'-chloro-4-(difluoromethyl)-[2,4'-bipyridin]-5-yl)oxy)-2,4-dimethylpentan-2-amine;
(S)-1-((4-(difluoromethyl)-5'-fluoro-2'-methyl-[2,4'-bipyridin]-5-yl)oxy)-2,4-dimethylpentan-2-amine;
(S)-1-((4-(difluoromethyl)-3'-fluoro-2'-methyl-[2,4'-bipyridin]-5-yl)oxy)-2,4-dimethylpentan-2-amine;
(S)-1-((4-(difluoromethyl)-6-(2-methylpyrimidin-4-yl)pyridin-3-yl)oxy)-2,4-dimethylpentan-2-amine;
(S)-1-(2-(difluoromethyl)-4-(2-methylpyrimidin-4-yl)phenoxy)-2,4-dimethylpentan-2-amine;
(S)-54(2-amino-2,4-dimethylpentyl)oxy)-3'-fluoro-6-methyl-[2,4'-bipyridin]-2'-amine;
(S)-1-((2'-chloro-3'-fluoro-6-methyl-[2,4'-bipyridin]-5-yl)oxy)-2,4-dimethylpentan-2-amine;
(S)-methyl (5-((2-amino-2,4-dimethylpentyl)oxy)-5'-fluoro-6-methyl-[2,4'-bipyridin]-2'-yl)carbamate;
(S)-1-((2'-chloro-5'-fluoro-6-methyl-[2,4'-bipyridin]-5-yl)oxy)-2,4-dimethylpentan-2-amine;
(S)-methyl (5-((2-amino-2,4-dimethylpentyl)oxy)-3'-fluoro-6-methyl-[2,4'-bipyridin]-2'-yl)carbamate;
(S)-1-((2'-chloro-6-(difluoromethyl)-[2,4'-bipyridin]-5-yl)oxy)-2,4-dimethylpentan-2-amine;
(S)-1-((2'-chloro-6-(difluoromethyl)-3-fluoro-[2,4'-bipyridin]-5-yl)oxy)-2,4-dimethylpentan-2-amine;
(S)-1-((6-(difluoromethyl)-3'-fluoro-2'-methyl-[2,4'-bipyridin]-5-yl)oxy)-2,4-dimethylpentan-2-amine;
((S)-1-((6-chloro-2'-(difluoromethyl)-[2,4'-bipyridin]-5-yl)oxy)-2,4-dimethylpentan-2-amine;
(S)-1-((4-(difluoromethyl)-6-(6-methylpyridazin-4-yl)pyridin-3-yl)oxy)-2,4-dimethylpentan-2-amine;
(S)-1-((2-(difluoromethyl)-6-(6-methylpyridazin-4-yl)pyridin-3-yl)oxy)-2,4-dimethylpentan-2-amine;
(R)-2,4-dimethyl-1-((2'-methyl-4-(trifluoromethyl)-[2,4'-bipyridin]-5-yl)oxy)pentan-2-amine;
(R)-2,4-dimethyl-1-((6-(quinolin-4-yl)-4-(trifluoromethyl)pyridin-3-yl)oxy)pentan-2-amine;
(R)-methyl (5-((2-amino-2,4-dimethylpentyl)oxy)-4-(trifluoromethyl)-[2,4'-bipyridin]-2'-yl)carbamate;
(R)-1-((2'-chloro-4-(difluoromethyl)-3'-fluoro-[2,4'-bipyridin]-5-yl)oxy)-2,4-dimethylpentan-2-amine;
(R)-1-((2'-chloro-4-(difluoromethyl)-5'-fluoro-[2,4'-bipyridin]-5-yl)oxy)-2,4-dimethylpentan amine;
(R)-1-((2'-chloro-4-(difluoromethyl)-[2,4'-bipyridin]-5-yl)oxy)-2,4-dimethylpentan-2-amine;
(R)-1-((4-(difluoromethyl)-2'-ethyl-[2,4'-bipyridin]-5-yl)oxy)-2,4-dimethylpentan-2-amine;
(R)-1-((4-(difluoromethyl)-5'-fluoro-2'-methyl-[2,4'-bipyridin]-5-yl)oxy)-2,4-dimethylpentan amine;
(R)-1-((4-(difluoromethyl)-3'-fluoro-2'-methyl-[2,4'-bipyridin]-5-yl)oxy)-2,4-dimethylpentan amine;
(R)-methyl (5-((2-amino-2,4-dimethylpentyl)oxy)-6-methyl-[2,4'-bipyridin]-2'-yl)carbamate;
(R)-1-((2',6-bis(difluoromethyl)-[2,4'-bipyridin]-5-yl)oxy)-2,4-dimethylpentan-2-amine;
(R)-1-((2',4-bis(difluoromethyl)-[2,4'-bipyridin]-5-yl)oxy)-2,4-dimethylpentan-2-amine;
(S)-methyl (4-(difluoromethyl)-54(2-hydroxy-2,4-dimethylpentyl)oxy)-[2,4'-bipyridin]-2'-yl)carbamate;
(S)-1-((4-(difluoromethyl)-Z-methyl-[2,4'-bipyridin]-5-yl)oxy)-2,4-dimethylpentan-2-ol;
(S)-methyl (5-((2-amino-2-(fluoromethyl)-4-methylpentyl)oxy)-6-(difluoromethyl)-[2,4'-bipyridin]-2'-yl)carbamate;
(R)-methyl (5-((2-amino-2-(fluoromethyl)-4-methylpentyl)oxy)-6-(difluoromethyl)-[2,4'-bipyridin]-2'-yl)carbamate;
(S)-methyl (5-((2-amino-2-(fluoromethyl)-4-methylpentyl)oxy)-4-(difluoromethyl)-[2,4'-bipyridin]-2'-yl)carbamate;
(R)-methyl (5-((2-amino-2-(fluoromethyl)-4-methylpentyl)oxy)-4-(difluoromethyl)-[2,4'-bipyridin]-2'-yl)carbamate;
(S)-1-((2',6-bis(difluoromethyl)-[2,4'-bipyridin]-5-yl)oxy)-2-(fluoromethyl)-4-methylpentan-2-amine;
(S)-1-((2',4-bis(difluoromethyl)-[2,4'-bipyridin]-5-yl)oxy)-2-(fluoromethyl)-4-methylpentan-2-amine;
(R)-1-((2',6-bis(difluoromethyl)-[2,4'-bipyridin]-5-yl)oxy)-2-(fluoromethyl)-4-methylpentan-2-amine;
(R)-1-((2',4-bis(difluoromethyl)-[2,4'-bipyridin]-5-yl)oxy)-2-(fluoromethyl)-4-methylpentan-2-amine;
(S)-1-((4-(difluoromethyl)-2'-methyl-[2,4'-bipyridin]-5-yl)oxy)-2-(fluoromethyl)-4-methylpentan-2-amine;
(R)-1-((4-(difluoromethyl)-2'-methyl-[2,4'-bipyridin]-5-yl)oxy)-2-(fluoromethyl)-4-methylpentan-2-amine;
(S)—N-(4-(4-((2-amino-4-methylpentyl)oxy)-3-fluorophenyl)pyridin-2-yl)acetamide;
(S)-1-((3-chloro-5-(7-fluoroquinolin-4-yl)pyridin-2-yl)oxy)-2,4-dimethylpentan-2-amine;

(S)-1-((3-chloro-5-(6-fluoroquinolin-4-yl)pyridin-2-yl)oxy)-2,4-dimethylpentan-2-amine;
(S)-1-((3-chloro-5-(2-methylpyrimidin-4-yl)pyridin-2-yl)oxy)-2,4-dimethylpentan-2-amine;
(S)-1-((2'-chloro-5-(difluoromethyl)-[3,4'-bipyridin]-6-yl)oxy)-2,4-dimethylpentan-2-amine;
(S)-1-((5-(difluoromethyl)-Z-methyl-[3,4'-bipyridin]-6-yl)oxy)-2,4-dimethylpentan-2-amine;
(S)-1-((3-(difluoromethyl)-5-(7-fluoroquinolin-4-yl)pyridin-2-yl)oxy)-2,4-dimethylpentan-2-amine;
(S)-methyl (6-((2-amino-2,4-dimethylpentyl)oxy)-5-(difluoromethyl)-[3,4'-bipyridin]-2'-yl)carbamate;
(S)-1-((5-(7-chloroquinolin-4-yl)-3-(difluoromethyl)pyridin-2-yl)oxy)-2,4-dimethylpentan-2-amine;
(S)-1-((3-(difluoromethyl)-5-(2-methylpyrimidin-4-yl)pyridin-2-yl)oxy)-2,4-dimethylpentan amine;
(S)-1-((2',5-bis(difluoromethyl)-[3,4'-bipyridin]-6-yl)oxy)-2,4-dimethylpentan-2-amine;
(S)-1-((3-(difluoromethyl)-5-(6-fluoroquinolin-4-yl)pyridin-2-yl)oxy)-2,4-dimethylpentan-2-amine;
(S)-1-((3-(difluoromethyl)-5-(5,7-difluoroquinolin-4-yl)pyridin-2-yl)oxy)-2,4-dimethylpentan-2-amine;
(S)-1-((3-(difluoromethyl)-5-(7-(trifluoromethyl)quinolin-4-yl)pyridin-2-yl)oxy)-2,4-dimethylpentan-2-amine;
(S)-1-((5-(difluoromethyl)-2',3'-dimethyl-[3,4'-bipyridin]-6-yl)oxy)-2,4-dimethylpentan-2-amine;
(S)-1-((3-(difluoromethyl)-5-(quinolin-4-yl)pyridin-2-yl)oxy)-2,4-dimethylpentan-2-amine;
(S)-1-((3-(difluoromethyl)-5-(7-methylquinolin-4-yl)pyridin-2-yl)oxy)-2,4-dimethylpentan-2-amine;
(S)-methyl (5-((2-amino-2,4-dimethylpentyl)oxy)-4-methoxy-[2,4'-bipyridin]-2'-yl)carbamate;
(S)-1-((2'-(difluoromethyl)-4-methoxy-[2,4'-bipyridin]-5-yl)oxy)-2,4-dimethylpentan-2-amine;
(S)-methyl (4-(4-((2-amino-2,4-dimethylpentyl)oxy)naphthalen-1-yl)pyridin-2-yl)carbamate;
(S)-2,4-dimethyl-1-((4-(quinolin-4-yl)naphthalen-1-yl)oxy)pentan-2-amine;
(S)-methyl (4-(5-((2-amino-2,4-dimethylpentyl)oxy)pyrimidin-2-yl)pyridin-2-yl)carbamate;
(S)-methyl (4-(2-((2-amino-2,4-dimethylpentyl)oxy)pyrimidin-5-yl)pyridin-2-yl)carbamate;
(S)-2,4-dimethyl-1-((2',4,6-trimethyl-[2,4'-bipyridin]-5-yl)oxy)pentan-2-amine;
(S)-methyl (5-((2-amino-2,4-dimethylpentyl)oxy)-4,6-dimethyl-[2,4'-bipyridin]-2'-yl)carbamate;
(S)-2,4-dimethyl-1-(4-(quinazolin-4-yl)-2-(trifluoromethyl)phenoxy)pentan-2-amine;
(S)-1-(4-(3,6-dihydro-2H-pyran-4-yl)-2-(trifluoromethyl)phenoxy)-2,4-dimethylpentan-2-amine;
(S)-2,4-dimethyl-1-(4-(2-methylquinolin-4-yl)-2-(trifluoromethyl)phenoxy)pentan-2-amine;
(S)-1-(4-(6-chloroquinolin-4-yl)-2-(trifluoromethyl)phenoxy)-2,4-dimethylpentan-2-amine;
(S)-1-((5-(5,7-difluoroquinolin-4-yl)-3-(trifluoromethyl)pyridin-2-yl)oxy)-2,4-dimethylpentan-2-amine;
(S)-2,4-dimethyl-1-((5-(quinolin-4-yl)-3-(trifluoromethyl)pyridin-2-yl)oxy)pentan-2-amine;
(S)-methyl (6-((2-amino-2,4-dimethylpentyl)oxy)-5-(trifluoromethyl)-[3,4'-bipyridin]-2'-yl)carbamate;
(S)-2,4-dimethyl-1-((2'-methyl-5-(trifluoromethyl)-[3,4'-bipyridin]-6-yl)oxy)pentan-2-amine;
(S)-1-((5-(6-chloroquinolin-4-yl)-3-methylpyridin-2-yl)oxy)-2,4-dimethylpentan-2-amine;
(S)-1-((5-(6-fluoroquinolin-4-yl)-3-methylpyridin-2-yl)oxy)-2,4-dimethylpentan-2-amine;
(S)-1-((5-(5,7-difluoroquinolin-4-yl)-3-methylpyridin-2-yl)oxy)-2,4-dimethylpentan-2-amine;
(S)-1-((5-(7-chloroquinolin-4-yl)-3-methylpyridin-2-yl)oxy)-2,4-dimethylpentan-2-amine;
(S)-1-((6-(5,7-difluoroquinolin-4-yl)-4-methylpyridin-3-yl)oxy)-2,4-dimethylpentan-2-amine;
(S)-1-((6-(7-fluoroquinolin-4-yl)-4-methylpyridin-3-yl)oxy)-2,4-dimethylpentan-2-amine;
(S)-1-((2',4-dimethyl-[2,4'-bipyridin]-5-yl)oxy)-2,4-dimethylpentan-2-amine;
(S)-1-((6-(6-chloroquinolin-4-yl)-4-methylpyridin-3-yl)oxy)-2,4-dimethylpentan-2-amine;
(S)-1-((6-(6-fluoroquinolin-4-yl)-4-methylpyridin-3-yl)oxy)-2,4-dimethylpentan-2-amine;
(S)-1-((6-(7-chloroquinolin-4-yl)-4-methylpyridin-3-yl)oxy)-2,4-dimethylpentan-2-amine;
(S)-1-((6-(7-fluoroquinolin-4-yl)-4-methylpyridin-3-yl)oxy)-2,4-dimethylpentan-2-amine;
(S)-1-((4-chloro-6-(5,7-difluoroquinolin-4-yl)pyridin-3-yl)oxy)-2,4-dimethylpentan-2-amine;
(S)-1-((4-chloro-[2,4'-bipyridin]-5-yl)oxy)-2,4-dimethylpentan-2-amine;
(S)-1-((4-chloro-6-(6-fluoroquinolin-4-yl)pyridin-3-yl)oxy)-2,4-dimethylpentan-2-amine;
(S)-1-((4-chloro-6-(quinolin-4-yl)pyridin-3-yl)oxy)-2,4-dimethylpentan-2-amine;
(S)-methyl (5-((2-amino-2,4-dimethylpentyl)oxy)-4-chloro-[2,4'-bipyridin]-2'-yl)carbamate;
(S)-1-((4-chloro-2'-methyl-[2,4'-bipyridin]-5-yl)oxy)-2,4-dimethylpentan-2-amine;
(S)-1-((4-chloro-6-(6-chloroquinolin-4-yl)pyridin-3-yl)oxy)-2,4-dimethylpentan-2-amine;
(S)-1-((2',4-dichloro-[2,4'-bipyridin]-5-yl)oxy)-2,4-dimethylpentan-2-amine;
(S)-1-((4-chloro-6-(7-fluoroquinolin-4-yl)pyridin-3-yl)oxy)-2,4-dimethylpentan-2-amine;
(S)-1-((4-chloro-6-(7-(trifluoromethyl)quinolin-4-yl)pyridin-3-yl)oxy)-2,4-dimethylpentan-2-amine;
(S)-1-((4-chloro-2',3-dimethyl-[2,4'-bipyridin]-5-yl)oxy)-2,4-dimethylpentan-2-amine;
(S)-1-((5-(difluoromethyl)-Z-methyl-[3,4'-bipyridin]-6-yl)oxy)-2,4-dimethylpentan-2-amine;
(R)-methyl (6-((2-amino-2,4-dimethylpentyl)oxy)-5-(difluoromethyl)-[3,4'-bipyridin]-2'-yl)carbamate;
(R)-1-((3-(difluoromethyl)-5-(quinolin-4-yl)pyridin-2-yl)oxy)-2,4-dimethylpentan-2-amine;
(R)-1-((3-(difluoromethyl)-5-(2-methylpyrimidin-4-yl)pyridin-2-yl)oxy)-2,4-dimethylpentan-2-amine;
(R)-1-((3-(difluoromethyl)-5-(5,7-difluoroquinolin-4-yl)pyridin-2-yl)oxy)-2,4-dimethylpentan-2-amine;
(R)-1-((5-(7-chloroquinolin-4-yl)-3-(difluoromethyl)pyridin-2-yl)oxy)-2,4-dimethylpentan-2-amine;
N-(4'-((2-amino-2,4-dimethylpentyl)oxy)-3'-methyl-[1,1'-biphenyl]-3-yl)acetamide;
(S)-1-(4-(2-(difluoromethyl)pyridin-4-yl)-2-(trifluoromethyl)phenoxy)-2,4-dimethylpentan-2-amine;
(S)-2,4-dimethyl-1-(4-(2-methylpyridn-4-yl)-2-(trifluoromethyl)phenoxy)pentan-2-amine;
(S)-methyl (5-((2-amino-2,4-dimethylpentyl)oxy)-6-methyl-[2,4'-bipyridin]-2'-yl)carbamate;
(S)-1-((4-(difluoromethyl)-Z-methyl-[2,4'-bipyridin]-5-yl)oxy)-2,4-dimethylpentan-2-amine;
(S)-1-((2',6-bis(difluoromethyl)-[2,4'-bipyridin]-5-yl)oxy)-2,4-dimethylpentan-2-amine;
(S)-2,4-dimethyl-1-((2'-methyl-4-(trifluoromethyl)-[2,4'-bipyridin]-5-yl)oxy)pentan-2-amine;

(S)-1-((4-(difluoromethyl)-3'-fluoro-2'-methyl-[2,4'-bipyridin]-5-yl)oxy)-2,4-dimethylpentan (S)-1-((6-(difluoromethyl)-3'-fluoro-2'-methyl-[2,4'-bipyridin]-5-yl)oxy)-2,4-dimethylpentan amine;

(S)-1-((3-(difluoromethyl)-5-(2-methylpyrimidin-4-yl)pyridin-2-yl)oxy)-2,4-dimethylpentan amine; and (S)-1-((4-chloro-Z-methyl-[2,4'-bipyridin]-5-yl)oxy)-2,4-dimethylpentan-2-amine;

and pharmaceutically acceptable salts thereof.

A specific AAK1 inhibitor is (S)-1-((2',6-bis(difluoromethyl)-[2,4'-bipyridin]-5-yl)oxy)-2,4-dimethylpentan-2-amine:

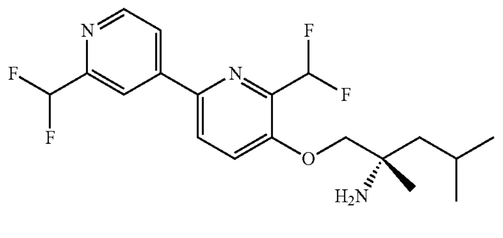 [SMILES: CC(C)C[C@](C)(N)COc1ccc(-c2ccnc(C(F)F)c2)nc1C(F)F]

or a pharmaceutically acceptable salt thereof. In some embodiments, the AAK1 inhibitor is (5)-1-((2',6-bis(difluoromethyl)-[2,4'-bipyridin]-5-yl)oxy)-2,4-dimethylpentan-2-amine phosphate. This and other AAK1 inhibitors disclosed herein can be prepared by methods known in the art as well as those described in U.S. Pat. No. 9,902,722.

6.3. Viral Infections

This invention is directed, in part, to methods of treating, managing and preventing a viral. A particular viral infection is a coronavirus infection.

Coronaviruses are a group of related viruses that cause diseases in mammals and birds. In humans, coronaviruses cause respiratory tract infections that can range from mild to lethal. Mild illnesses include some cases of the common cold (which has other possible causes, predominantly rhinoviruses), while more lethal varieties can cause severe acute respiratory syndrome (SARS), Middle East respiratory syndrome (MERS), and coronavirus disease 2019 (COVID-19).

Coronaviruses constitute the subfamily Orthocoronavirinae, in the family Coronaviridae, order Nidovirales, and realm Riboviria. They are enveloped viruses with a positive-sense single-stranded RNA genome and a nucleocapsid of helical symmetry. The genome size of coronaviruses ranges from approximately 26 to 32 kilobases, one of the largest among RNA viruses (see, Woo et al., Viruses. 2 (8): 1804-1820). They have characteristic club-shaped spikes that project from their surface, which in electron micrographs create an image reminiscent of the solar corona from which their name derives.

Coronaviruses were first discovered in the 1930s when an acute respiratory infection of domesticated chickens was shown to be caused by infectious bronchitis virus (IBV). In the 1940s, two more animal coronaviruses, mouse hepatitis virus (MHV) and transmissible gastroenteritis virus (TGEV), were isolated.

Human coronaviruses were discovered in the 1960s (see, Kahn et al., The Pediatric Infectious Disease Journal. 24 (11 Suppl): S223-27, discussion S226). The earliest ones studied were from human patients with the common cold, which were later named human coronavirus 229E and human coronavirus OC43 (see, Geller et al., Viruses. 4 (11): 3044-68). Other human coronaviruses have since been identified, including SARS-CoV in 2003, HCoV NL63 in 2004, HKU1 in 2005, MERS-CoV in 2012, and SARS-CoV-2 in 2019. Most of these have involved serious respiratory tract infections (see, Su et al., Trends in Microbiology. 24 (6): 490-502; and Zhu et al., The New England Journal of Medicine. 382 (8): 727-733).

In some embodiments of this invention, the subject (e.g., a human patient) is infected by SARS-CoV2. In some embodiments, the subject is infected by HCoV NL63. In some embodiments, the subject is infected by MERS-CoV. In some embodiments, the subject is infected by SARS-CoV. In some embodiments, the subject is infected by CoV-229E. In some embodiments, the subject is infected by CoV-OC43. In some embodiments, the subject is infected by CoV-HKU1.

SARS-Cov-2

Severe acute respiratory syndrome coronavirus 2 (SARS-CoV-2) is a virus strain that causes coronavirus disease 2019 (COVID-19), a respiratory illness. At times, it has been referred to by its provisional name "2019 novel coronavirus" (2019-nCoV). SARS-CoV-2 is a positive-sense single-stranded RNA virus (see, Su et al., Trends in Microbiology. 24 (6): 490-502; and Zhu et al., The New England Journal of Medicine. 382 (8): 727-733). It is contagious in humans, and the World Health Organization (WHO) has designated the ongoing pandemic of COVID-19 a Public Health Emergency of International Concern (see, Almeida et al., Nature. 220 (5168): 650; McIntosh et al., Current Topics in Microbiology and Immunology/Ergebnisse der Mikrobiologie and Immunitätsforschung. Berlin, Heidelberg: Springer: 87; and Kahn et al., The Pediatric Infectious Disease Journal. 24 (11 Suppl): S223-27, discussion S226). The virus is reportedly spread between people through close contact and via respiratory droplets produced from coughs or sneezes and is believed to enter human cells by binding to the receptor angiotensin converting enzyme 2 (ACE2) (see, Cui et al., Nature Reviews. Microbiology. 17 (3): 181-92; and Li et al., Science. 309 (5742): 1864-68).

The whole genome sequence of a SARS-CoV-2 strain is represented by SEQ ID NO: 1 (NCBI Reference Sequence: NC_045512.2). As used herein, the term "SARS-CoV-2-like coronavirus" refers to a coronavirus with a genome homology of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more to the nucleotide sequence of SEQ ID NO: 1.

In some embodiments of this invention, a SARS-CoV-2-like coronavirus comprises one or more genes that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the corresponding gene sequence(s) of SARS-CoV-2.

In some embodiments, a SARS-CoV-2-like coronavirus comprises a gene encoding a structural protein (an envelope protein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a SARS-CoV-2 envelope gene (SEQ ID NO: 2).

In some embodiments, a SARS-CoV-2-like coronavirus comprises a gene encoding a structural protein (a membrane glycoprotein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a SARS-CoV-2 membrane glycoprotein gene (SEQ ID NO: 3).

In some embodiments, a SARS-CoV-2-like coronavirus comprises a gene encoding a structural protein (a spike glycoprotein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a SARS-CoV-2 spike glycoprotein gene (SEQ ID NO: 4).

In some embodiments, a SARS-CoV-2-like coronavirus is a virus that is positively detected using any known detection method for SARS-CoV-2, for example, a molecular test such as PCR, or a serological test such as an antibody test.

6.3.1. CoV-229E

Human coronavirus 229E (CoV-229E) is a species of coronavirus which infects humans and bats (see, Lim et al., Diseases. 4 (3): 26). It is an enveloped, positive-sense, single-stranded RNA virus which enters its host cell by binding to the APN receptor (see, Fehr et al., Springer. 1282: 1-23). Along with Human coronavirus OC43, it is one of the viruses responsible for the common cold (see, Susanna et al., J Virology. 2011 November; 85(21): 11325-11337; and Gaunt et al., International Committee on Taxonomy of Viruses (ICTV). October 2018). The species is a member of the genus Alphacoronavirus and subgenus Duvinacovirus.

The whole genome sequence of a CoV-229E strain is represented by SEQ ID NO: 5 (NCBI Reference Sequence: NC_002645.1). As used herein, the term "CoV-229E-like coronavirus" refers to a coronavirus with a genome homology of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more to the nucleotide sequence of SEQ ID NO: 5.

In some embodiments of this invention, a CoV-229E-like coronavirus comprises one or more genes that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the corresponding gene sequence(s) of CoV-229E.

In some embodiments, a CoV-229E-like coronavirus comprises a gene encoding a structural protein (an envelope protein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a CoV-229E envelope gene (SEQ ID NO: 6).

In some embodiments, a CoV-229E-like coronavirus comprises a gene encoding a structural protein (a membrane glycoprotein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a CoV-229E membrane glycoprotein gene (SEQ ID NO: 7).

In some embodiments, a CoV-229E-like coronavirus comprises a gene encoding a structural protein (a surface glycoprotein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a CoV-229E surface glycoprotein gene (SEQ ID NO: 8).

In some embodiments, a CoV-229E-like coronavirus is a virus that is positively detected using any known detection method for CoV-229E, for example, a molecular test such as PCR, or a serological test such as an antibody test.

6.3.2. CoV-OC43

Human coronavirus OC43 (HCoV-OC43) is a member of the species Betacoronavirus 1 which infects humans and cattle (see, e.g., Lee, Paul. Molecular epidemiology of human coronavirus OC43 in Hong Kong (Thesis). The University of Hong Kong Libraries. doi:10.5353/th); the ncbi.nlm.nih.gov website; and Lim et al., Diseases. 4 (3): 26). The infecting coronavirus is an enveloped, positive-sense, single-stranded RNA virus which enters its host cell by binding to the N-acetyl-9-O-acetylneuraminic acid receptor (see, e.g., Li et al., Annual Review of Virology. 3 (1): 237-261).

The whole genome sequence of a CoV-OC43 strain is represented by SEQ ID NO: 9 (NCBI Reference Sequence: AY391777.1). As used herein, the term "CoV-OC43-like coronavirus" refers to a coronavirus with a genome homology of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more to the nucleotide sequence of SEQ ID NO: 9

In some embodiments of this invention, a CoV-OC43-like coronavirus comprises one or more genes that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the corresponding gene sequence(s) of CoV-OC43.

In some embodiments, a CoV-OC43-like coronavirus comprises a gene encoding a structural protein (an envelope protein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a CoV-OC43 envelope gene (SEQ ID NO: 10).

In some embodiments, a CoV-OC43-like coronavirus comprises a gene encoding a structural protein (a membrane glycoprotein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a CoV-OC43 membrane glycoprotein gene (SEQ ID NO: 11).

In some embodiments, a CoV-OC43-like coronavirus comprises a gene encoding a structural protein (a spike surface glycoprotein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a CoV-OC43 spike surface glycoprotein gene (SEQ ID NO: 12).

In some embodiments, a CoV-OC43-like coronavirus is a virus that is positively detected using any known detection method for CoV-OC43, for example, a molecular test such as PCR, or a serological test such as an antibody test.

6.3.3. MERS-CoV

Middle East respiratory syndrome (MERS), also known as camel flu (see, e.g., Parry et al., Travel alert after eighth camel flu death. The Times), is a viral respiratory infection caused by the MERS-coronavirus (MERS-CoV) (see, e.g., Middle East respiratory syndrome coronavirus (MERS-CoV).WHO website). Symptoms may range from none, to mild, to severe (see, e.g., Zumla et al., Lancet. 386 (9997): 995-1007, 2015). Typical symptoms include fever, cough, diarrhea, and shortness of breath.[2] The disease is typically more severe in those with other health problems (see, e.g., Zumla et al., Lancet. 386 (9997): 995-1007, 2015; and Middle East respiratory syndrome coronavirus (MERS-CoV).WHO website).

MERS-CoV is a coronavirus believed to be originally from bats. However, humans are typically infected from camels, either during direct contact or indirectly (Middle East respiratory syndrome coronavirus (MERS-CoV). WHO website). Spread between humans typically requires close contact with an infected person. Its spread is uncommon outside of hospitals (Zumla et al., Lancet. 386 (9997): 995-1007, 2015).

The whole genome sequence of a MERS-CoV strain is represented by SEQ ID NO: 13 (NCBI Reference Sequence: NC_019843.3). As used herein, the term "MERS-CoV-like coronavirus" refers to a coronavirus with a genome homology of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more to the nucleotide sequence of SEQ ID NO: 13.

In some embodiments of this invention, a MERS-CoV-like coronavirus comprises one or more genes that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the corresponding gene sequence(s) of MERS-CoV.

In some embodiments, a MERS-CoV-like coronavirus comprises a gene encoding a structural protein (an envelope protein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a MERS-CoV envelope gene (SEQ ID NO: 14).

In some embodiments, a MERS-CoV-like coronavirus comprises a gene encoding a structural protein (a membrane protein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a MERS-CoV membrane protein gene (SEQ ID NO: 15).

In some embodiments, a MERS-CoV-like coronavirus comprises a gene encoding a structural protein (a spike protein) that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a MERS-CoV spike protein gene (SEQ ID NO: 16).

In some embodiments, a MERS-CoV-like coronavirus is a virus that is positively detected using any known detection method for MERS-CoV, for example, a molecular test such as PCR, rRT-PCR or a serological test such as an antibody test in blood and respiratory samples.

6.3.4. Dengue Virus

This invention also encompasses methods of treating, managing and preventing a dengue virus infection.

Dengue virus (DENV) is the cause of dengue fever. It is a mosquito-borne, single positive-stranded RNA virus of the family Flaviviridae; genus Flavivirus (see, e.g., Rodenhuis-Zybert et al., Cellular and Molecular Life Sciences. 67 (16): 2773-86, 2010; and WHO (2009). Dengue Guidelines for Diagnosis, Treatment, Prevention and Control, World Health Organization. ISBN 978-92-4-154787-1). Five serotypes of the virus have been found (see, e.g., Normile D et al., Science. 342 (6157): 415, 2013; and Dwivedi et al., Genomics, proteomics and evolution of Dengue virus. Briefings in functional genomics.16(4): 217-227, 2017), all of which can cause the full spectrum of disease.

Dengue viruses are spread to people through the bite of an infected *Aedes* species (*Ae. aegypti* or *Ae. albopictus*) mosquito. Dengue is common in more than 100 countries around the world. Forty percent of the world's population, about 3 billion people, live in areas with a risk of dengue. Dengue is often a leading cause of illness in areas with risk.

In some embodiments, the Dengue virus is a Dengue virus 1. In some embodiments, the Dengue virus is a Dengue virus 2. In some embodiments, the Dengue virus is a Dengue virus 3. In some embodiments, the Dengue virus is a Dengue virus 4.

In some embodiments, the Dengue virus is a Dengue virus-like virus. In some embodiments, a Dengue virus-like virus comprises a gene encoding one or more protein that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a gene encoding the corresponding Dengue virus protein.

6.3.5. Hepatitis B Virus (HBV)

This invention also encompasses methods of treating, managing and preventing a hepatitis B virus (HBV) infection.

Hepatitis B virus (HBV), is a partially double-stranded DNA virus (see, e.g., Ryu et al., 2017, Molecular Virology of Human Pathogenic Viruses. Academic Press. 247-260), a species of the genus Orthohepadnavirus and a member of the Hepadnaviridae family of viruses. This virus causes the disease hepatitis B (see, e.g., Hassan et al., 2008, Association between hepatitis B virus and pancreatic cancer, Journal of Clinical Oncology, 26 (28): 4557-62). Viral infection by Hepatitis B virus (HBV) causes many hepatocyte changes due to the direct action of a protein encoded by the virus, HBx, and to indirect changes due to a large increase in intracellular reactive oxygen species (ROS) after infection.

Hepatitis B virus is a member of the Hepadnavirus family (see, e.g., Zuckerman A J (1996). Chapter 70: Hepatitis Viruses. In Baron S; et al. (eds.). Baron's Medical Microbiology ($4^{th}$ ed.). Univ of Texas Medical Branch. ISBN 978-0-9631172-1-2). The virus particle, called Dane particle (virion), consists of an outer lipid envelope and an icosahedral nucleocapsid core composed of protein. The nucleocapsid encloses the viral DNA and a DNA polymerase that has reverse transcriptase activity similar to retroviruses. The outer envelope contains embedded proteins which are involved in viral binding of, and entry into, susceptible cells. The virus is one of the smallest enveloped animal viruses with a virion diameter of 42 nm, but pleomorphic forms exist, including filamentous and spherical bodies lacking a core. These particles are not infectious and are composed of the lipid and protein that forms part of the surface of the virion, which is called the surface antigen (HbsAg), and is produced in excess during the life cycle of the virus (see, e.g., Howard C R, 1986, The biology of hepadnaviruses, The Journal of General Virology 67 (7): 1215-35).

In some embodiments, the HBV is a HBV-like virus. In some embodiments, an HBV-like virus comprises a gene encoding one or more protein that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more homologous to the nucleotide sequence of a gene encoding the corresponding HBV protein.

6.4. Pharmaceutical Compositions

Embodiments of the present invention comprise the use of an AAK1 inhibitor described herein and formulated with one or more pharmaceutically acceptable excipients, diluents, carriers and/or adjuvants. Some embodiments comprise the use of an AAK1 inhibitor formulated with one or more pharmaceutically acceptable auxiliary substances. In particular, an AAK1 inhibitor may be formulated with one or more pharmaceutically acceptable excipients, diluents, carriers, and/or adjuvants.

In some embodiments, the AAK1 inhibitor can be combined with one or more additional agent(s), e.g., anti-cancer agents, antiviral agents, and anti-malarial agents, to prepare a composition of the invention, and the composition can include one or more pharmaceutically acceptable excipients, diluents, carriers and/or adjuvants. Any suitable agents known in the art can be used as additional agent(s) described herein. The additional agent can be, for example, a small molecule compound, an oligonucleotide, a DNA, an RNA, a microRNA, a small interfering RNA, a polypeptide, a protein, or a combination thereof.

In some embodiments, the additional agent(s) are inhibitors of one or more steps of the coronavirus life cycle. For example, the additional agent(s) can be viral entry inhibitors, e.g., small molecule fusion inhibitors, peptide analogs, or antibodies. The additional agent(s) can also be, for example, a viral assembly inhibitor or a viral budding inhibitor, In some embodiments, the additional agent(s) are agent(s) that treat or ameliorate one or more symptoms related to a coronavirus infection, for example. fever, cough, shortness of breath, difficulty breathing, persistent pain in the chest, pressure in the chest, bluish lips or face, tiredness, runny nose, or sore throat.

In some embodiments, the additional agent(s) are agent(s) that treat or ameliorate one or more symptoms of a complication of a coronavirus infection, such as acute respiratory failure, pneumonia, acute respiratory distress syndrome, acute liver failure, acute cardiac injury, secondary infection, acute kidney injury, septic shock, disseminated intravascular coagulation, or rhabdomylosis.

In some embodiments, the additional agent is a chloroquine phosphate (e.g., hydroxylchloroquine). In some embodiments, the additional agent is a nonsteroidal anti-inflammatory drug (NSAID).

A wide variety of pharmaceutically acceptable excipients are known in the art. Pharmaceutically acceptable excipients have been amply described in a variety of publications, including, for example, Gennaro (2000), "Remington: The Science and Practice of Pharmacy"; Pharmaceutical Dosage Forms and Drug Delivery Systems (1999); and Handbook of Pharmaceutical Excipients (2000).

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents, and the like, are readily available to the public.

In some embodiments, the AAK1 inhibitor is administered to the subject using any means capable of resulting in the desired effect (e.g., reduction in viral load, reduction in one or more symptoms related to a coronavirus infection, increase in survival of the subject). Thus, the AAK1 inhibitor can be incorporated into a variety of formulations for therapeutic administration. For example, the AAK1 inhibitor can be formulated into pharmaceutical compositions by combination with appropriate, pharmaceutically acceptable carriers or excipients, and may be formulated into preparations in solid, semi-solid, liquid, or gaseous forms, such as tablets, capsules, powders, granules, ointments, solutions, suppositories, injections, inhalants, and aerosols.

In pharmaceutical dosage forms, the AAK1 inhibitor may be administered in the form of its pharmaceutically acceptable salts, or a subject active agent may be used alone or in appropriate association, as well as in combination, with other pharmaceutically active compounds. The following methods and excipients are merely exemplary and are in no way limiting.

In some implementations pharmaceutical dosage forms are suitable for oral administration. For oral preparations, the AAK1 inhibitor can be used alone or in combination with appropriate additives to make tablets, powders, granules or capsules, for example, with conventional additives, such as lactose, mannitol, corn starch, or potato starch; with binders, such as crystalline cellulose, cellulose derivatives, acacia, corn starch, or gelatins; with disintegrators, such as corn starch, potato starch, or sodium carboxymethylcellulose; with lubricants, such as talc or magnesium stearate; and if desired, with diluents, buffering agents, moistening agents, preservatives, and flavoring agents.

Pharmaceutical compositions comprising the AAK1 inhibitor can be formulated into preparations for injection by dissolving, suspending, or emulsifying them in an aqueous or nonaqueous solvent, such as vegetable or other similar oils, synthetic aliphatic acid glycerides, esters of higher aliphatic acids, or propylene glycol; and if desired, with conventional additives such as solubilizers, isotonic agents, suspending agents, emulsifying agents, stabilizers, and preservatives.

Examples of pharmaceutical compositions include a solution, a suspension, a dispersion, a mouthwash, a spray, an orodispersible solid preparation, a chewing gum, a syrup, a candy, a gel, a paste, an eye drop, a capsule, a micro-capsule, a tablet, a mini-tablet, a micro-tablet, a pellet, a multiparticulate, a micronized particulate, a pill, a powder, a granule, a micro-granule, a suppository, a lotion, a ointment, a tincture, or a cream. In some embodiments, the pharmaceutical composition is in a form of a solution. In some embodiments, the pharmaceutical composition is in a form of a tablet.

6.5. Methods of Treatment, Management and Prevention

This invention is directed, in part, to methods of treating a virus infection that comprise administering to a subject in need thereof a therapeutically effective amount of an AAK1 inhibitor disclosed herein. In some embodiments, these include methods of treating infections with coronaviruses such as severe acute respiratory syndrome coronavirus (SARS-CoV), Middle East respiratory syndrome coronavirus (MERS-CoV), severe acute respiratory syndrome coronavirus 2 (SARS-CoV-2 or 2019-nCoV), SARS-CoV-2-like coronavirus, human coronavirus 229E (CoV-229E), CoV-229E-like coronavirus, human coronavirus OC43 (CoV-OC43), and CoV-OC43-like coronavirus. In some embodiments, these include methods of treating infection with a Dengue virus such as Dengue virus 1, Dengue virus 2, Dengue virus 3 and Dengue virus 4. In some embodiments, these include methods of treating infection with an HBV.

Particular methods of treatment or management reduce or prevent an increase in the severity of one or more symptoms of a viral infection. Examples of symptoms include fever, cough, shortness of breath, difficulty breathing, persistent pain in the chest, pressure in the chest, bluish lips or face, tiredness, runny nose, and sore throat.

This invention also encompasses methods of inhibiting the entry, assembly and/or budding of a coronavirus in a host cell, which comprise contacting the host cell with an AAK1 inhibitor. In some embodiments, the host cell is in vitro. In others, it is in vivo. In some embodiments, the AAK1 inhibitor blocks the entry of the coronavirus into a host cell. In some embodiments, the entry of the coronavirus into the host cell is by endocytosis. In some embodiments, the endocytosis is dependent on the binding of the coronavirus to a host cell-surface receptor. In some embodiments, the endocytosis is independent from the binding of the coronavirus to a host cell-surface receptor.

Examples of host cells include a respiratory system organ or tissue cell, such as a lung cell (e.g., alveolar cell). A lung cell can be any cell that resides or is related to the lung. In some embodiments, the lung cell is an alveolar epithelial cell. In some embodiments, the alveolar epithelial cell is an AT2 alveolar epithelial cell.

Without being limited by theory, it is believed that in some embodiments of the invention, the AAK1 inhibitor blocks binding of a coronavirus structural protein to a host protein, e.g., a mu-2 subunit of a clathrin adaptor protein (AP) complex. In some embodiments, the AAK1 inhibitor competes with the coronavirus structural protein for binding to the host protein. In some embodiments, the AAK1 inhibitor competes with the host protein for binding to the coronavirus structural protein. In some embodiments, the coronavirus structural protein is a coronavirus envelope (E) protein. In some embodiments, the coronavirus structural protein is a membrane (M) protein. In some embodiments, the coronavirus structural protein is a spike (S) protein. In some embodiments, the AAK1 inhibitor blocks binding of one or more structural protein(s) to a host protein.

In some embodiments, the binding of a coronavirus structural protein to a host protein is inhibited by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the level of binding of a coronavirus structural protein to a host protein in the absence of the AAK1 inhibitor.

In some embodiments, the AAK1 inhibitor blocks binding of a coronavirus structural protein to a host protein, e.g., a mu-2 pp of a clathrin adaptor protein (AP) complex, e.g. an AP2 complex with a 50% inhibitory concentration ($IC_{50}$) of about 100 μM to 50 μM, about 50 μM to 25 μM, about 25 μM to 10 μM, about 10 μM to 5 μM, about 5 μM to 1 μM, about 1 μM to 500 nM, about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, or less than about 5 nM.

In some embodiments, the $EC_{50}$ of the AAK1 inhibitor in treating a viral infection, e.g., a coronavirus infection or a symptom related to a viral infection is about 100 μM to 50 μM, about 50 μM to 25 μM, about 25 μM to 10 μM, about 10 μM to 5 μM, about 5 μM to 1 μM, about 1 μM to 500 nM, about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, or less than about 5 nM. In some embodiments, the $EC_{50}$ of the AAK1 inhibitor is about 2.40 μM. In some embodiments, the $EC_{50}$ of the AAK1 inhibitor is >10 μM.

In some embodiments, the $TC_{50}$ of the AAK1 inhibitor in treating a viral infection, e.g., a coronavirus infection or a symptom related to a viral infection is about 100 μM to 50 μM, about 50 μM to 25 μM, about 25 μM to 10 μM, about 10 μM to 5 μM, about 5 μM to 1 μM, about 1 μM to 500 nM, about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, or less than about 5 nM. In some embodiments, the $TC_{50}$ of the AAK1 inhibitor is about 5.62 μM. In some embodiments, the $TC_{50}$ of the AAK1 inhibitor is >10 μM.

In some embodiments, the AAK1 inhibitor inhibits intracellular assembly of the viral particle of the coronavirus. The intracellular assembly of the viral particle can be assessed by any known methods in the art. For example, the intracellular assembly of viral particles can be assessed by microscopy including direct or indirect imaging of the viral particles. The intracellular assembly can also be assessed by, for example, testing the expression level or size of the structural proteins of the viral particles.

In some embodiments, the intracellular assembly of the viral particle is inhibited by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the level of intracellular assembly of the viral particles in the absence of the AAK1 inhibitor.

In some embodiments, the AAK1 inhibitor inhibits intracellular trafficking of the coronavirus. The intracellular trafficking of the coronavirus can be assessed by any known methods in the art. For example, the intracellular trafficking of the coronavirus viral particles can be assessed by microscopy including direct or indirect imaging of the viral particles.

In some embodiments, the intracellular trafficking of the coronavirus is inhibited by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the level of intracellular trafficking of the coronavirus in the absence of the AAK1 inhibitor.

Methods of detecting and assessing different steps of virus life cycle, such as virus entry, viral particle assembly, intracellular trafficking, and virus budding, as well as assessing the efficacy of therapeutics to block or reduce these parts of the virus life cycle, are known in the art. For example, Ventura et al., PLoS Pathogens 15 (12); Uchil et al., Annual review of virology 6, 501-524; Pi et al., Journal of virology 93 (21), e00930-19; Lu et al., Advances in virus research 105, 239-273; Lu et al., Nature 568 (7752), 415-419; Sewald et al., Science 350 (6260), 563-567; and Munro et al., Science 346 (6210), 759-763 describe microscopic imaging-based techniques for virus life cycle detection.

In some embodiments, the AAK1 inhibitor described herein inhibits viral replication by at by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the level of coronavirus replication in the absence of the AAK1 inhibitor.

In some embodiments, the AAK1 inhibitor, when contacted with a virus-infected cell (e.g., a coronavirus-infected lung cell), inhibits viral replication in the cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the level of viral replication in a viral-infected cell not contacted with the AAK1 inhibitor.

In still yet another embodiment, the AAK1 inhibitor, when contacted with an virus-infected cell (e.g., a coronavirus-infected lung cell), reduces the amount of infectious viral particles produced by the infected cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the number of infectious viral particles produced by the cell not contacted with the AAK1 inhibitor.

In yet another embodiment, the AAK1 inhibitor, when administered in one or more doses to a subject (e.g., a human subject) infected with a coronavirus, reduces the viral load in the subject by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the viral load in the subject not administered with the pharmaceutical composition. Methods of detecting and assessing viral load of coronavirus are known in the art and are described, for example, by Zou, et al., N Engl J Med 2020; 382:1177-1179.

6.5.1. Dosages

Embodiments of the AAK1 inhibitor can be administered to a subject in one or more doses. In some embodiments, the AAK1 inhibitor can be administered in an amount of about 10 mg to 1000 mg per dose, e.g., about 10 mg to 20 mg, about 20 mg to 25 mg, about 25 mg to 50 mg, about 50 mg to 75 mg, about 75 mg to 100 mg, about 100 mg to 125 mg, about 125 mg to 150 mg, about 150 mg to 175 mg, about 175 mg to 200 mg, about 200 mg to 225 mg, about 225 mg to 250 mg, about 250 mg to 300 mg, about 300 mg to 350 mg, about 350 mg to 400 mg, about 400 mg to 450 mg, about 450 mg to 500 mg, about 500 mg to 750 mg, or about 750 mg to 1000 mg per dose. In some embodiments, the AAK1 inhibitor is administered to the subject in one or more single dose(s) of about 40 mg. In some embodiments, the AAK1 inhibitor is administered to the subject in one or more single dose(s) of about 200 mg.

In some embodiments, the amount of the AAK1 inhibitor per dose is determined on a per body weight basis. For example, in some embodiments, the AAK1 inhibitor can be administered in an amount of about 0.5 mg/kg to 100 mg/kg, e.g., about 0.5 mg/kg to 1 mg/kg, about 1 mg/kg to 2 mg/kg, about 2 mg/kg to 3 mg/kg, about 3 mg/kg to 5 mg/kg, about 5 mg/kg to 7 mg/kg, about 7 mg/kg to about 10 mg/kg, about 10 mg/kg to 15 mg/kg, about 15 mg/kg to 20 mg/kg, about 20 mg/kg to 25 mg/kg, about 25 mg/kg to 30 mg/kg, about 30 mg/kg to 40 mg/kg, about 40 mg/kg to 50 mg/kg, about 50 mg/kg to 60 mg/kg, about 60 mg/kg to 70 mg/kg, about 70 mg/kg to 80 mg/kg, about 80 mg/kg to 90 mg/kg, or about 90 mg/kg to 100 mg/kg, or more than about 100 mg/kg.

Those of skill will readily appreciate that dose levels can vary as a function of several different factors including, without limitation, the specific AAK1 inhibitor administered, the severity of the symptoms, the age and/or physical size of the subject, and the susceptibility of the subject to side effects. Preferred dosages for a given compound are readily determinable by those of skill in the art by a variety of means.

In some embodiments, multiple doses of the AAK1 inhibitor are administered. The frequency of administration of the AAK1 inhibitor can vary depending on any of a variety of factors, e.g., severity of the symptoms, and the like. For example, in some embodiments, the AAK1 inhibitor is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in some embodiments, the AAK1 inhibitor is administered continuously.

The duration of administration of the AAK1 inhibitor is administered, can vary, depending on any of a variety of factors known by those skilled in the art (e.g., patient response, route of administration, dosage form). For example, the AAK1 inhibitor can be administered over a period of time of about one day to one week, about two weeks to four weeks, about one month to two months, about two months to four months, about four months to six months, about six months to eight months, about eight months to 1 year, about 1 year to 2 years, or more.

6.5.2. Routes of Administration

Embodiments of the present invention provide methods and compositions for the administration of the AAK1 inhibitor to a patient (e.g., a human) using any available method and route suitable for drug delivery, including in vivo and ex vivo methods, as well as systemic and localized routes of administration.

Routes of administration include oral, intranasal, intramuscular, intratracheal, subcutaneous, intradermal, topical application, intravenous, rectal, nasal, and other enteral and parenteral routes of administration. Routes of administration may be combined, if desired, or adjusted depending upon the agent and/or the desired effect. An active agent can be administered in a single dose or in multiple doses.

Embodiments of the AAK1 inhibitor can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes. Parenteral administration can be conducted to effect systemic or local delivery of the AAK1 inhibitor. Where systemic delivery is desired, administration typically involves invasive or systemically absorbed topical or mucosal administration of pharmaceutical preparations.

The AAK1 inhibitor can also be delivered to the subject by enteral administration. Enteral routes of administration include, but are not limited to, oral and rectal delivery.

Methods of administration of the AAK1 inhibitor through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available patches that deliver their product continuously via electric pulses through unbroken skin for periods of several days or more.

In some embodiments, the pharmaceutical composition is administered orally, intravenously, subcutaneously, epidurally, intraventricularly, intramuscularly, intraperitoneally, or via inhalation. In some embodiments, the pharmaceutical composition is administered orally.

6.5.3. Subjects

Subjects suitable for treatment using methods disclosed herein include subjects who are infected, or are at a risk of infection, with a virus disclosed herein.

Subjects suitable for treatment with embodiments of the present invention include treatment failure patients. The term “treatment failure patients” (or “treatment failures”) as used herein generally refers to coronavirus-infected patients who failed to respond to previous therapy for coronavirus (referred to as “non-responders”) or who initially responded to previous therapy, but in whom the therapeutic response was not maintained (referred to as “relapsers”). The previous therapy generally can include treatment with any antiviral agent other than an AAK1 inhibitor of the present disclosure.

Subjects suitable for treatment with embodiments of the present disclosure include individuals who have been clinically diagnosed as infected with a coronavirus infection. Individuals who are infected with a coronavirus can be identified by detecting coronavirus RNA in a specimen from the individual, such as lower respiratory tract specimens, upper respiratory tract specimens (e.g., nasopharyngeal), anterior nares specimen, mid-turbinate specimen, ropharyngeal (OP) specimen, nasal mid-turbinate (NMT) swab, or a saliva specimen, and/or having an anti-coronavirus antibody in their serum.

In some embodiments, the methods described herein further comprise diagnosing the subject of an infection by coronavirus prior to the administration of the pharmaceutical composition. Any suitable diagnosing methods known in the art can be used for the methods described herein. For example, nucleic acid tests such as PCR, reverse transcription PCR (RT-PCT), antibody tests such as western blot, enzyme-linked immunosorbent assay (ELISA), and/or other commercial or non-commercial diagnosis methods can be used in the methods described herein.

Suitable subjects for treatment using the methods described herein include symptomatic patients and asymptomatic patients. Symptomatic patients experience one or more symptoms of a coronavirus infection described herein or known in the art. The symptoms can be from mild to severe. Asymptomatic patient does not experience any symptoms of a coronavirus or experience one or more mild symptoms of a coronavirus. In some embodiments, a symptomatic patient is in need of hospitalization. In some embodiments, an asymptomatic patient does not require hospitalization.

6.6. Examples

Aspects of particular embodiments of this invention are illuminated by the following examples. The examples describe testing the antiviral activity of at least one compound of the invention as well as compounds already known to have an antiviral effect (e.g., remdesivir).

6.6.1. Example 1. In Vitro Effect Against CoV-229E Strain in MRC-5 Cells

Alpha coronavirus 229E (CoV-229E) strain was purchased from ATCC (catalog #VR-740) and virus stocks were produced in MRC-5 cells. Inhibition of virus-induced cytopathic effects (CPE) and cell viability following alpha coronavirus 229E (CoV-229E) replication in MRC-5 cells were measured by XTT tetrazolium dye. MRC-5 cells (5×103 cells per well) were seeded in 96-well flat-bottom tissue culture plates and allowed to adhere overnight. Following overnight incubation with each of the indicated agents, diluted test compounds and virus diluted to a predetermined titer to yield 85% to 95% cell killing at 6 days post-infection were added to the plate. Following incubation at 37° C., 5% $CO_2$ for six days, cell viability was measured by XTT staining. The optical density of the cell culture plate will be determined spectrophotometrically at 450 nm and 650 nm using Softmax Pro 4.6 software. Percent CPE reduction of the virus-infected wells and the percent cell viability of uninfected drug control wells were calculated to determine the $EC_{50}$ and $TC_{50}$ values using four parameter curve fit analysis. The relative effectiveness of the investigational product in inhibiting viral replication compared to inducing cell death ($TC_{50}$ value/$EC_{50}$ value) is defined as the therapeutic index or selectivity index.

Figure 2:
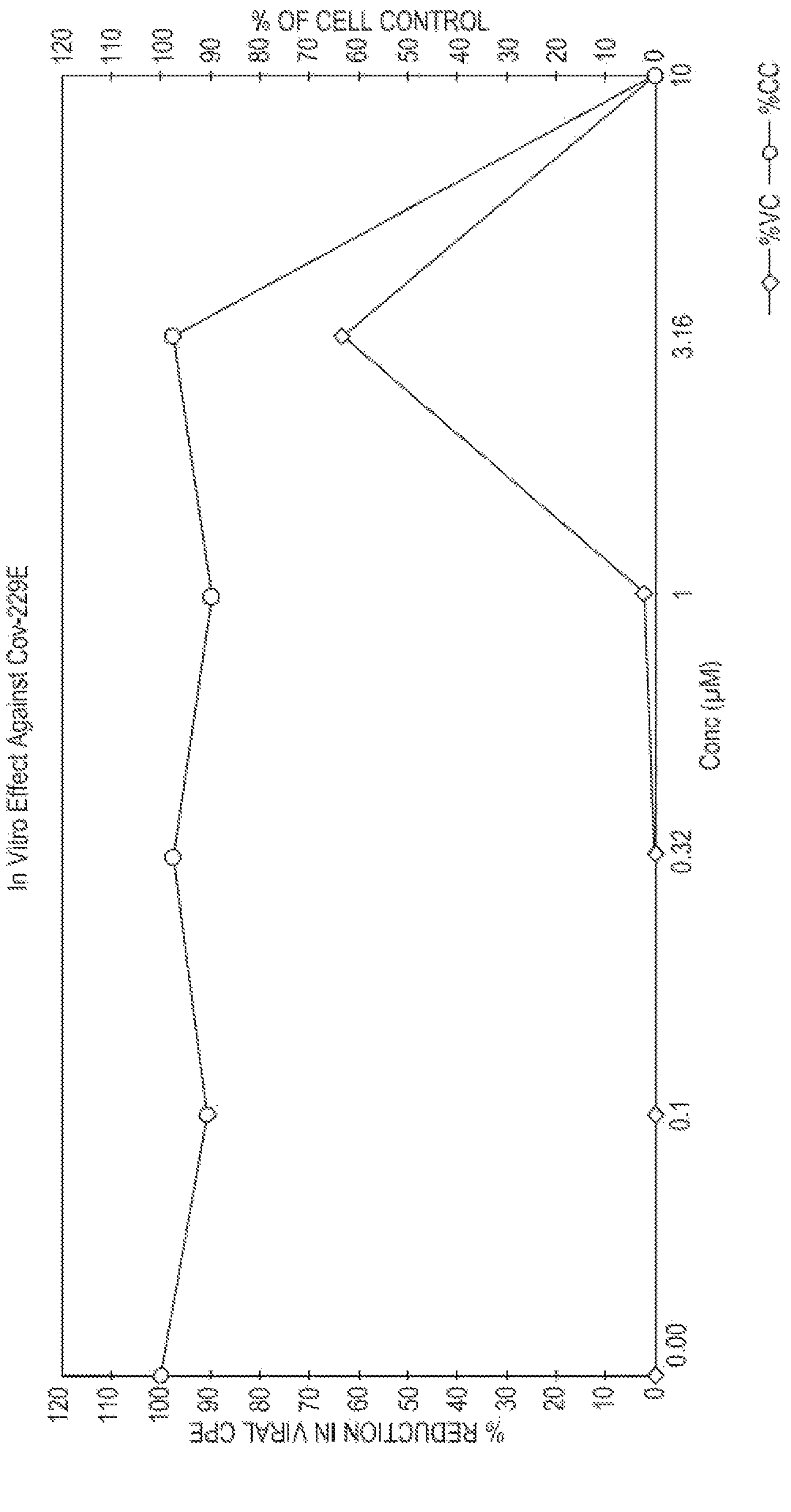

FIG. 1 shows representative raw data used to determine $EC_{50}$ and $TC_{50}$ values for (S)-1-((2',6-bis(difluoromethyl)-[2,4'-bipyridin]-5-yl)oxy)-2,4-dimethylpentan-2-amine phosphate ("Compound 1"). FIG. 2 provides a graphical representation of antiviral data obtained for the compound. The $EC_{50}$ of Compound 1 as determined in this assay about 2.40 μM, and the $TC_{50}$ is 5.62 μM. The compound's therapeutic index is about 2.34.

The antiviral effects determined for various other compounds in this experiment are shown in Table 1.

TABLE 1

| Compound | $EC_{50}$ (μM) | $TC_{50}$ (μM) | Therapeutic Index |
|---|---|---|---|
| Remdesivir | 0.13 | >2.00 | >15.4 |
| Chloroquine | 0.49 | 1.71 | 3.49 |
| Sunitinib | 0.63 | 1.32 | 2.10 |
| Compound 1 | 2.40 | 5.62 | 2.34 |

6.6.2. Example 2. In Vitro Effect Against CoV-OC43 Strain on Huh-7 Cells

Full-dose antiviral effects were tested using Compound 1 and sunitinib malate. Anti-coronaviral assays were performed against the OC43 strain of seasonal human coronavirus (HCoV). All test-items were provided in a powder form. 30 mM stocks of the solid samples were prepared in 100% DMSO and stored at −20° C.

Huh-7 adherent cells (hepatocellular carcinoma from a 57-year-old Japanese man) were used to evaluate the antiviral activity of the test-items against HCoV-OC43. Test-items were pre-incubated with the target cells for 30 min at 33° C., before adding the virus inoculum to cells to initiate infection. Putative inhibitors were present in the cell culture medium for the duration of the virus adsorption. Then, the viral inoculum was washed away and the test-items were added at the same concentrations utilized during the preincubation with cells. Cells were incubated with test-items for 6 days, at which time a neutral red uptake assay was performed to determine the extent of the virus-induced cytopathic effect (CPE). Prevention of the CPE was used as a surrogate marker to determine the antiviral activity of the test-items.

A cell viability assay was set up in parallel for the same duration of the corresponding infectivity assay. Cell viability was determined by the XTT assay.

Eight concentrations (CPE assay) or nine concentrations (cytotoxicity assay) of the samples were tested in duplicates. 3-fold serial dilutions started at 30 μM (CPE) or 90 μM (cytotoxicity). Test-items were diluted using culture medium containing 0.01% DSMO. When possible, $EC_{50}$ (antiviral) and $CC_{50}$ (inhibition of viability) values of the test-items were determined using GraphPad Prism software.

To evaluate antiviral activity against HCoV (OC43 strain), a CPE-based antiviral assay was performed by infecting Huh-7 cells in the presence or absence of test-items. Infection of cells leads to cytopathic effects and cell death. In this assay, reduction of CPE in the presence of inhibitors was used as a surrogate marker to determine the antiviral activity of the tested items. Cell viability was determined using the neutral red uptake assay.

Huh-7 cells were maintained in DMEM with 10% fetal bovine serum (FBS), hereby called DMEM10. Cells were seeded at 12,500 cells per well in 96-well clear flat bottom plates and maintained in DMEM10 at 33° C. for 24 hours. The day of infection, samples were diluted 3-fold in U-bottom plates using DMEM with 2% FBS, hereby called DMEM2. Test-item dilutions were prepared at 1.25× the final concentration and 40 μL were incubated with the target cells at 33° C. for 30 minutes. Following the test-material pre-incubation, 10 μL of virus prepared in DMEM2 was added to each well, and plates were incubated at 33° C. in a humidified incubator with 5% $CO_2$ for 2 hours. After this period, viral inoculum was removed and cells were incubated for 6 days at 33° C. in DMEM2 containing the same concentrations of test-items utilized in the virus adsorption stage. All dilutions for test-items, control inhibitors, mock, and vehicle samples were diluted in DMEM2 containing 0.01% DMSO.

Test-items were evaluated in duplicates using serial 3-fold dilutions. Controls included cells incubated with no virus ("mock-infected"), infected cells incubated with DMEM2 alone (vehicle control+0.01% DMSO), and wells without cells (to determine background). Some wells were treated with 5 μM chloroquine (CQ), an immunosuppressant and anti-malarial with broad antiviral activity against coronaviruses. After 6 days of infection, cells were processed to monitor cell viability with the neutral red (NR) uptake assay.

The virus-induced CPE was monitored under the microscope after 4 and 5 days of infection and at day 6 cells were stained with neutral red to monitor cell viability. Viable cells incorporate neutral red in their lysosomes. The uptake relies on the ability of live cells to maintain the pH inside the lysosomes lower than in the cytoplasm. This process requires ATP. Inside the lysosome the dye becomes charged and is retained there. After a 3 h incubation with neutral red (0.033%) the extra dye was washed and the neutral red taken by lysosomes was then extracted for 15 minutes with a solution containing 50% ethanol and 1% acetic acid to monitor absorbance at 490 nm.

The average signal (absorbance at 490 nm) obtained in wells with no cells was subtracted from all samples. Then, the average NR uptake observed in infected cells (in the absence of vehicle) was calculated and then subtracted from all samples to determine the inhibition of the virus induced CPE. Data points were then normalized to the average signal observed in the mock (uninfected cells) after subtraction of the absorbance signal observed in infected cells. With this method, uninfected cells remained viable and take up NR at high levels. In the absence of antiviral agents the virus-induced CPE kills infected cells, resulting in low uptake of NR by the cell culture (0% inhibition). By contrast, incubation with the antiviral agent CQ prevents the virus induced CPE and leads to higher uptake of NR, similar to that observed in uninfected cells when 100% inhibition of the virus replication is accomplished.

The test-items evaluated (sunitinib and Compound 1) partially prevented the virus induced cytopathic effect (20 to 30% inhibition) when tested at 3.3 μM or 10 μM. The antiviral effect disappeared at 30 μM, likely due to the compound-induced toxicity observed with these molecules at such concentration. By comparison, chloroquine (CQ) tested at 5 μM prevented most of the virus-induced CPE, and cell viability levels remained at about 88% of those observed in uninfected cells ("mock"). Table 2 summarizes the antiviral and compound-induced-cytotoxicity activities ($EC_{50}$ and $CC_{50}$ values) of the test-items.

TABLE 2

| | OC43 CPE Assay | | | Cytotoxicity (Huh-7 cells) | | |
|---|---|---|---|---|---|---|
| Sample | $EC_{50}$ (μM) | S/B* | C.V.# | $CC_{50}$ (μM) | S/B | C.V. |
| Compound 1 | >30 | 7 | 1.2 | 24 | 15 | 2.9 |
| Sunitinib maleate | >30 | 7 | 1.2 | 13 | 15 | 2.9 |

Where:
*signal to background level was calculated by dividing the signal in uninfected cells ("mock-infected"), by the signal in infected cells; and
#C.V. for the assays was calculated as the average of C.V. values determined for all data points displaying Neutral Red uptake of 50% or greater as compared to the signal in uninfected cells.

Selectivity indices were not determined since no antiviral activity displaying 50% inhibition or greater was observed at any of the concentrations tested. Signal-to-background ratios (S/B), and average coefficients of variation (C.V.) of duplicate data-points for which 50% or greater uptake of Neutral Red was observed, as compared to uptake in uninfected cells (CPE assay). When inhibition of OC43, or cell viability ($CC_{50}$) did not reach 50% at the highest concentration tested, the $EC_{50}$ or $CC_{50}$ values are shown as greater than the highest concentration tested.

Quality controls for the infectivity assays were performed on every plate to determine: i) signal to background (S/B) values; ii) inhibition by a known inhibitor of coronavirus (CPE assay) or a known cytotoxic agent (cell viability assay), and iii) variation of the assay, as measured by the coefficient of variation (C.V.) of all data points. All controls worked as anticipated for each assay. Chloroquine (CQ), a known inhibitor of coronaviruses, including HCoV-OC43, potently prevented the virus-induced CPE in the 6-day assay. The viability control used in the XTT assays (emetine) inhibited cell viability by more than 90%.

Overall variation of duplicates in the antiviral assay was 1.2% and overall variation in the viability assays was 2.9%. The signal-to-background (S/B) for this assay was 7-fold, determined as comparing the uptake in uninfected cells with that observed in cells challenged with OC43 in the presence of vehicle alone. Signal-to-background (S/B) for the viability assays was 15.

In the viability assay (XTT) to assess compound-induced cytotoxicity, uninfected cells were incubated with seven concentrations of test-items or control inhibitors dilutions. The incubation temperature and duration of the incubation period mirrored the conditions of the prevention of CPE assay. Cell viability was evaluated with the XTT method. The tetrazolium salt (XTT) is cleaved to an orange formazan dye throughout a reaction that occurs only in viable cells with active mitochondria. The formazan dye is directly quantified using a scanning multi-well spectrophotometer. Background levels obtained from wells with no cells were subtracted from all data-points. The extent of viability was monitored by measuring absorbance at 490 nm.

Quality control and analysis of cytotoxicity data. The average signal obtained in wells with no cells was subtracted from all samples. Readout values were given as a percentage of the average signal observed in uninfected cells treated with vehicle alone (tissue culture media). Controls also included vehicle alone containing 0.1% DMSO. The signal-to-background (S/B) obtained was 15. Emetine was used as a cytotoxic compound control in all viability assays. Emetine blocked cell viability by more than 90% when tested at 5 μM.

TABLE 3

| Raw OD-Absorbance 490 nm | | | | | | | | | | | |
|---|---|---|---|---|---|---|---|---|---|---|---|
| Conc. (μM) | 30 | 10 | 3.3 | 1.1 | 0.4 | 0.12 | 0.04 | 0.01 | Vehicle | CQ (5 μM) | Mock |
| Compd. 1 | 0.057 | 0.322 | 0.292 | 0.115 | 0.092 | 0.092 | 0.078 | 0.102 | 0.097 | 0.693 | 0.776 |
| | 0.056 | 0.297 | 0.253 | 0.165 | 0.092 | 0.099 | 0.089 | 0.101 | 0.103 | 0.689 | 0.784 |
| | | | | | | | | | 0.111 | | 0.769 |
| | | | | | | | | | 0.105 | | 0.762 |
| Sunitinib | 0.051 | 0.214 | 0.312 | 0.094 | 0.086 | 0.101 | 0.094 | 0.102 | | | |
| maleate | 0.053 | 0.280 | 0.136 | 0.101 | 0.090 | 0.105 | 0.098 | 0.120 | | | |

Raw values in Table 3 represent absorbance measured at 490 nm to determine the extent of uptake of neutral red. Infected cells develop extensive CPE after six days of infection and displayed significantly reduced staining with neutral red. A490 values are shown for each test condition. All samples were infected except those indicated as "mock". Samples shown as vehicle were infected in the presence of DMEM2. Samples treated with Chloroquine (CQ) are also shown. Concentrations are shown in μM.

TABLE 4

| Inhibition of OC43 Virus-Induced CPE in Huh-7 Cells (%) | | | | | | | | | | |
|---|---|---|---|---|---|---|---|---|---|---|
| Conc. (μM) | 30 | 10 | 3.3 | 1.1 | 0.4 | 0.12 | 0.04 | 0.01 | CQ (5 μM) | Mock |
| Compd. 1 | −7.1 ± 0.1 | 30.7 ± 2.6 | 25.2 ± 4.1 | 5.4 ± 5.3 | −1.8 ± 0.1 | −1.2 ± 0.8 | −3.0 ± 1.1 | −0.4 ± 0.2 | 87.8 ± 0.4 | 100 ± 1.4 |
| Sunitinib maleate | −7.8 ± 0.2 | 21.4 ± 7.0 | 17.9 ± 18.5 | −1.0 ± 0.8 | −2.4 ± 0.4 | −0.1 ± 0.4 | −1.2 ± 0.4 | 1.1 ± 1.9 | | |

Figure 3:
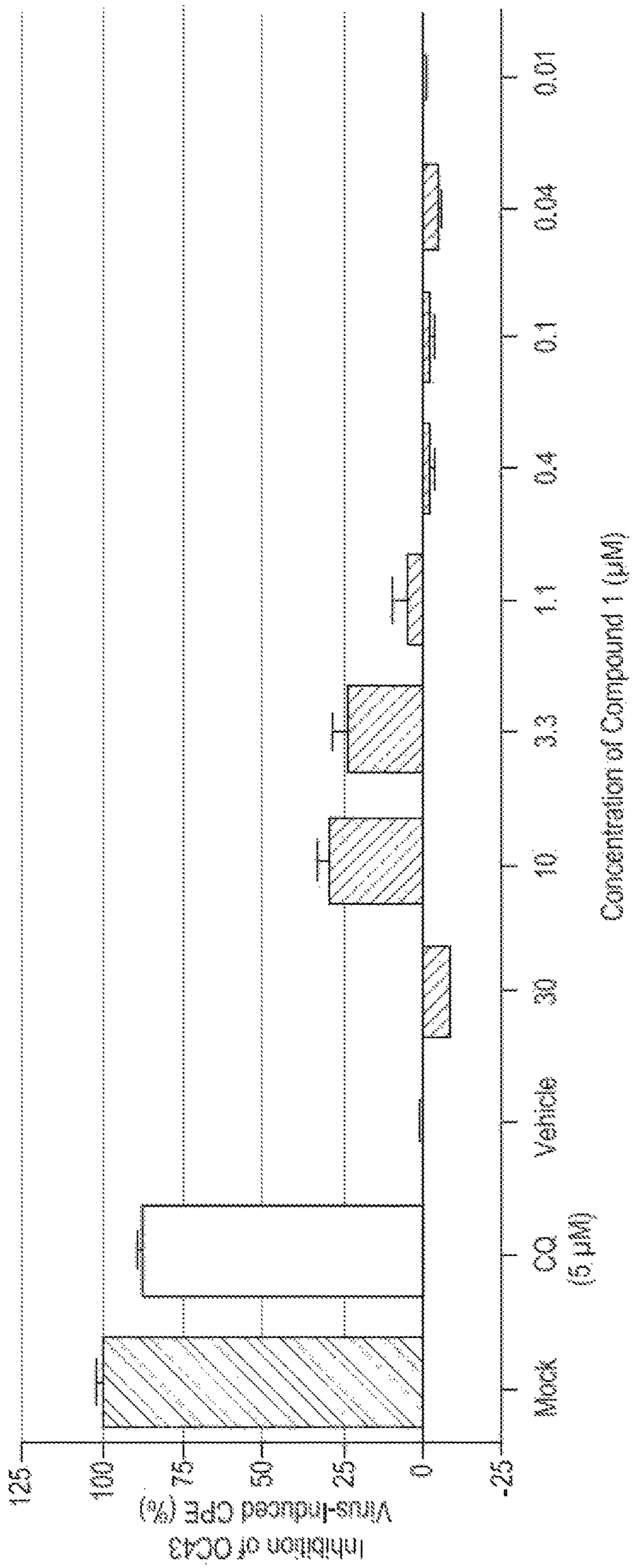

The data in Table 4 and FIG. 3 show the inhibition of the HCoV-OC43-induced CPE in Huh-7 cells. Prevention of the virus induced CPE was used as a surrogate marker to determine the extent of replication of HCoV-OC43. The extent of neutral red uptake in infected cells in the presence of vehicle alone is indicative of no inhibition of the virus-induced CPE. Complete inhibition (100%) results in neutral red uptake equal to those observed in mock-infected cells (0.01% DMSO). To obtain inhibition values, the average absorbance (A490) in cells infected in the absence of test-items ("vehicle") was subtracted from all values, and then all values were normalized to those obtained for uninfected ("mock") to indicate 100% inhibition. Percentage inhibition is shown for each test condition. All samples were infected except those indicated as "mock". Samples treated with chloroquine are shown as CQ. Concentrations are shown in μM. Data shown for test-items represents the average and standard deviation of duplicates.

TABLE 5

| Viability of Huh-7 Cells (A490) | | | | | | | | | |
|---|---|---|---|---|---|---|---|---|---|
| Conc. (μM) | 90 | 30 | 10 | 3.3 | 1.1 | 0.37 | 0.12 | 0.04 | 0.01 |
| Compd. 1 | 0.055 | 0.052 | 0.915 | 1.017 | 0.925 | 0.886 | 0.822 | 0.731 | 0.749 |
| | 0.054 | 0.053 | 1.016 | 1.085 | 0.996 | 0.928 | 0.825 | 0.759 | 0.746 |
| Sunitinib | 0.053 | 0.058 | 0.543 | 0.642 | 0.676 | 0.732 | 0.719 | 0.738 | 0.721 |
| maleate | 0.054 | 0.055 | 0.554 | 0.601 | 0.665 | 0.765 | 0.752 | 0.751 | 0.651 |

Huh-7 cells were incubated for 6 days in the presence of different concentrations of test-items, or with vehicle alone (medium only). For each data point in Table 5, the individual raw data is shown (absorbance values at 490 nm). Table 6 shows raw data values for the control samples, including "no cells" control (background), medium alone (0.01% DMSO), or in the presence of 0.1% DMSO), and the positive control with the cytotoxic agent emetine (1 μM or 5 μM).

TABLE 6

| Controls | Viability (A490) | |
|---|---|---|
| No Cells (background) | 0.051 | 0.051 |
| Medium Only (0.01% DMSO) | 0.761 | 0.720 |
| | 0.738 | 0.747 |
| Medium (0.1% DMSO) | 0.732 | 0.676 |
| Controls | 5 μM | 1 μM |
| Emetine | 0.104 | 0.176 |
| | 0.111 | 0.179 |

Figure 4:
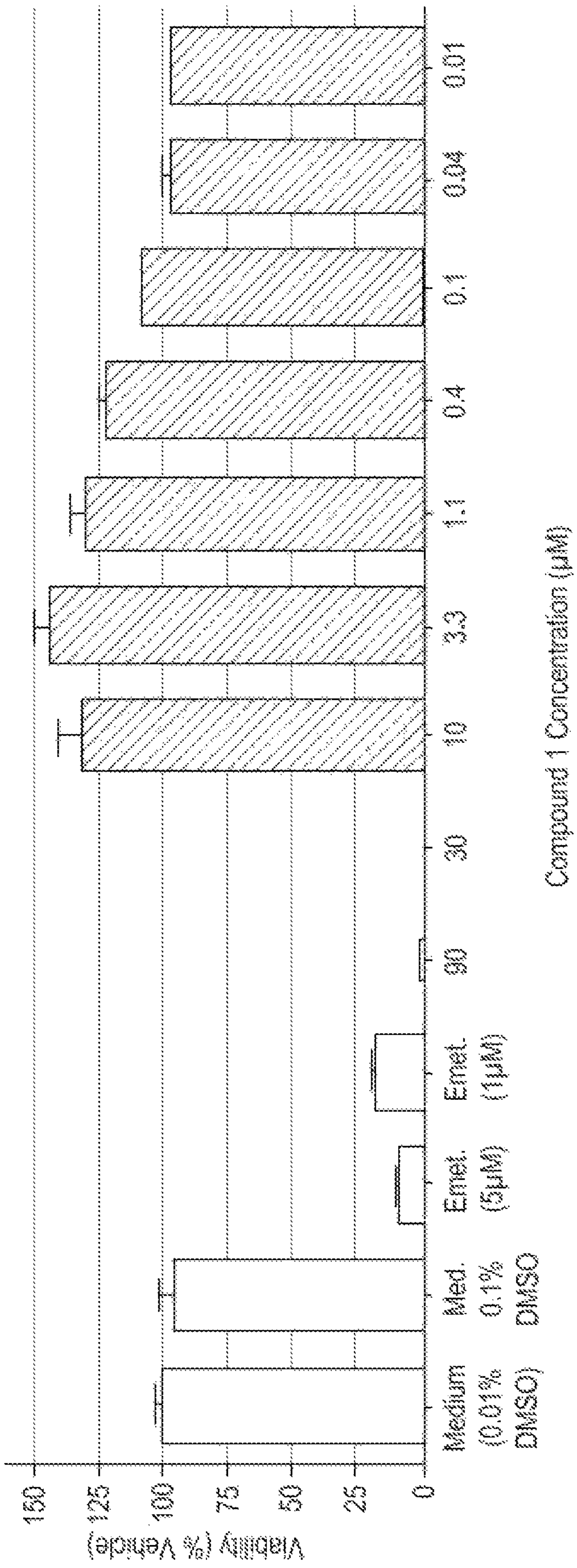
Figure 5:
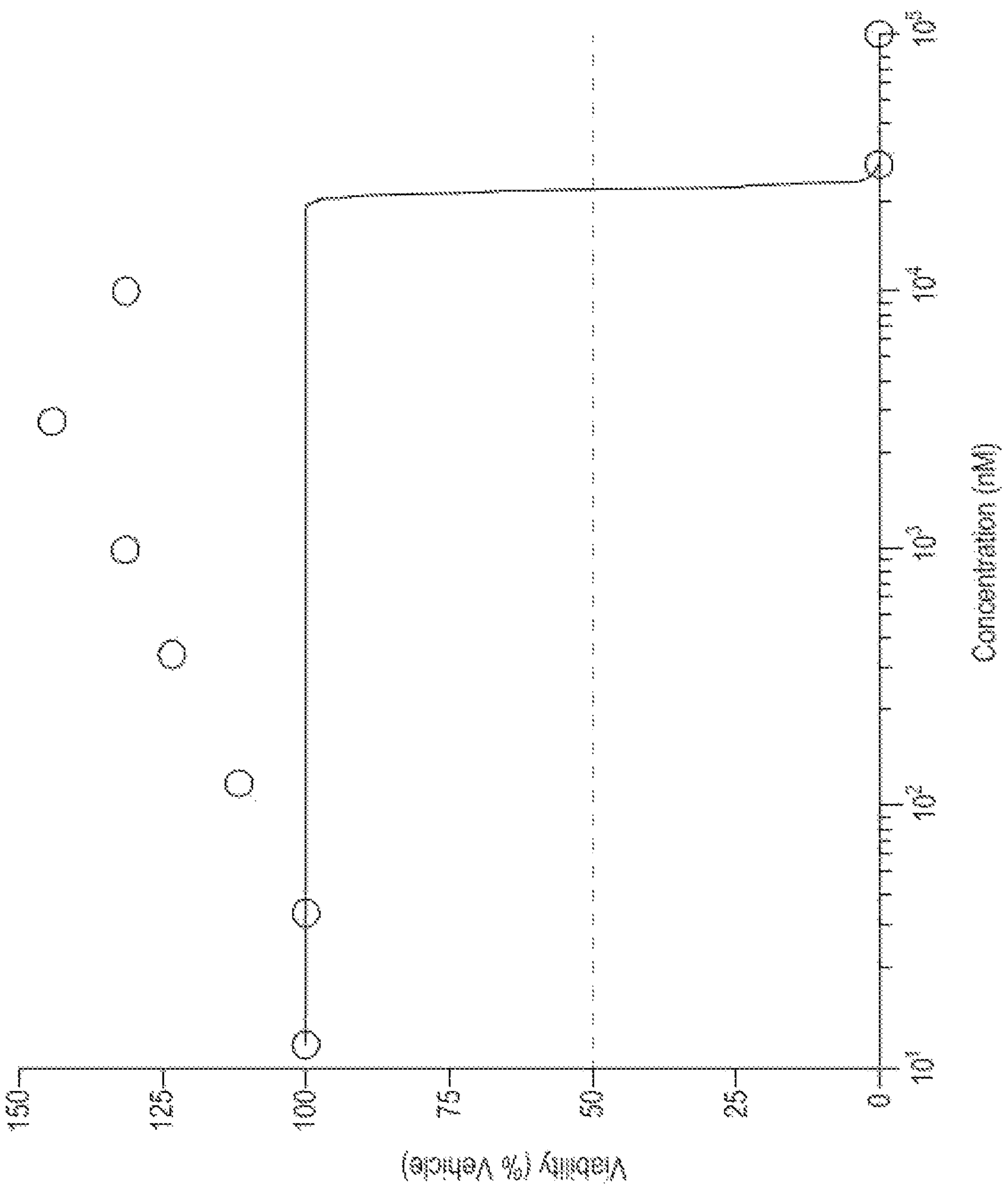

FIG. 4 shows the cell viability of Huh-7 cells at different concentrations of Compound 1. FIG. 5 depicts a plot used in the determination of $CC_{50}$ values.

TABLE 7

| Inhibition of Huh-7 Cells (% vehicle alone) | | | | | | | | | |
|---|---|---|---|---|---|---|---|---|---|
| Conc. (μM) | 90 | 30 | 10 | 3.3 | 1.1 | 0.37 | 0.12 | 0.04 | 0.01 |
| Compd. 1 | 0.5 ± 0.1 | 0.2 ± 0.1 | 132.4 ± 10.3 | 144.8 ± 7.0 | 131.7 ± 7.3 | 124.0 ± 4.3 | 111.9 ± 0.3 | 100.5 ± 2.9 | 100.9 ± 0.3 |
| Sunitinib maleate | 0.4 ± 0.1 | 0.8 ± 0.3 | 72.0 ± 1.1 | 82.6 ± 4.2 | 89.7 ± 1.1 | 101.0 ± 3.4 | 99.1 ± 3.4 | 100.4 ± 1.3 | 92.0 ± 7.2 |

Values in Table 7 indicate the percent viability remaining after a 6-day treatment with test-items. Values are shown as percentage of the viability observed in samples incubated with vehicle alone (medium only). Background levels observed in wells with no cells were subtracted from all data-points. Data represents the mean and standard deviation of duplicates. Table 8 shows the percentage viability observed with several controls, including medium alone (0.01% DSM 0), or in the presence of 0.1% DMSO, and the positive control with the cytotoxic agent emetine (1 μM or 5 μM).

TABLE 8

| Controls | Viability (A490) |
|---|---|
| No Cells (background) | 0.0 ± 0.0 |
| Medium Only (0.01% DMSO) | 100.0 ± 2.5 |
| Medium (0.1% DMSO) | 94.6 ± 5.7 |

TABLE 8-continued

| Controls | 5 μM | 1 μM |
|---|---|---|
| Emetine | 8.2 ± 0.7 | 18.3 ± 0.3 |

6.6.3. Example 3. In Vitro Effect Against HCoV-OC43 Strain on H292 Cells

By selecting an appropriate concentration of virus (one that causes infection in appropriate cell line) this study assessed the virustatic or virucidal properties of titrated test items.

H292 cells (NCI-H292) were seeded into 96 well plates for assessment of efficacy against HCoV-OC43 (Betacoronavirus 1, ATCC® VR-1558™). Media was removed and each test item serially diluted (8-point, 3-fold dose titration) and added to all experimental wells, plates were incubated for 30 minutes with each test item alone. After 30 minutes, virus was added at a single concentration (100× median tissue culture infectious dose ($TCID_{50}$)). One hour following infection, overlay media was added to the wells for the duration of the study. Vehicle and positive control wells were set up to control for any influence on cell viability. Cells were visually inspected daily for the appearance of any CPE. Assay duration was 6 days.

$CC_{50}$ (half maximal cytotoxic concentration) was also determined in the same manner and plates developed to show any cytotoxic effect of the compounds on cells in the absence of viral infection.

For each virus and compound combination determine the $EC_{50}$ values using the MTT colorimetric assay for mammalian cell survival and calculating the $EC_{50}$. For each cell line determine the toxicity of each compound on cells using the MTT colorimetric assay for mammalian cell survival and calculating the $CC_{50}$ value.

HCoV-OC43 was used to infect the NCI-H292 cell line. Cells were grown to sufficient numbers in growth media with supplements. Once cells were confluent, they were seeded into 96 well flat-bottomed plates. When cells reached 90% confluency, media was removed and virus, serially diluted 1:10, was added to all experimental wells. One hour following infection, virus was removed and overlay media was added to the wells for the duration of the study. Vehicle and positive control wells were set up to control for any influence on cell viability. Cells were visually inspected daily for the appearance of any CPE (cytopathic effect apparent from rounding of cells showing infection leading to death of cell and plaques).

For HCoV-OC43, CPE was visually assessed in each well for the presence of viral infection and the $TCID_{50}$ value calculated according to the method described by Reed and Muench (see, Reed et al., A simple method of estimating fifty percent endpoints. American Journal of Epidemiology Vol. 27 Issue 3.1938).

The stock of HCoV-OC43 was determined to have a $TCID_{50}$ value sufficiently high to be used in efficacy studies (>$1\times10^4$ $TCID_{50}$/ml). Specifically, the $TCID_{50}$ of HCoV-OC43 on H292 cells was $4\times10^5$ ($TCID_{50}$/ml).

Figure 6:
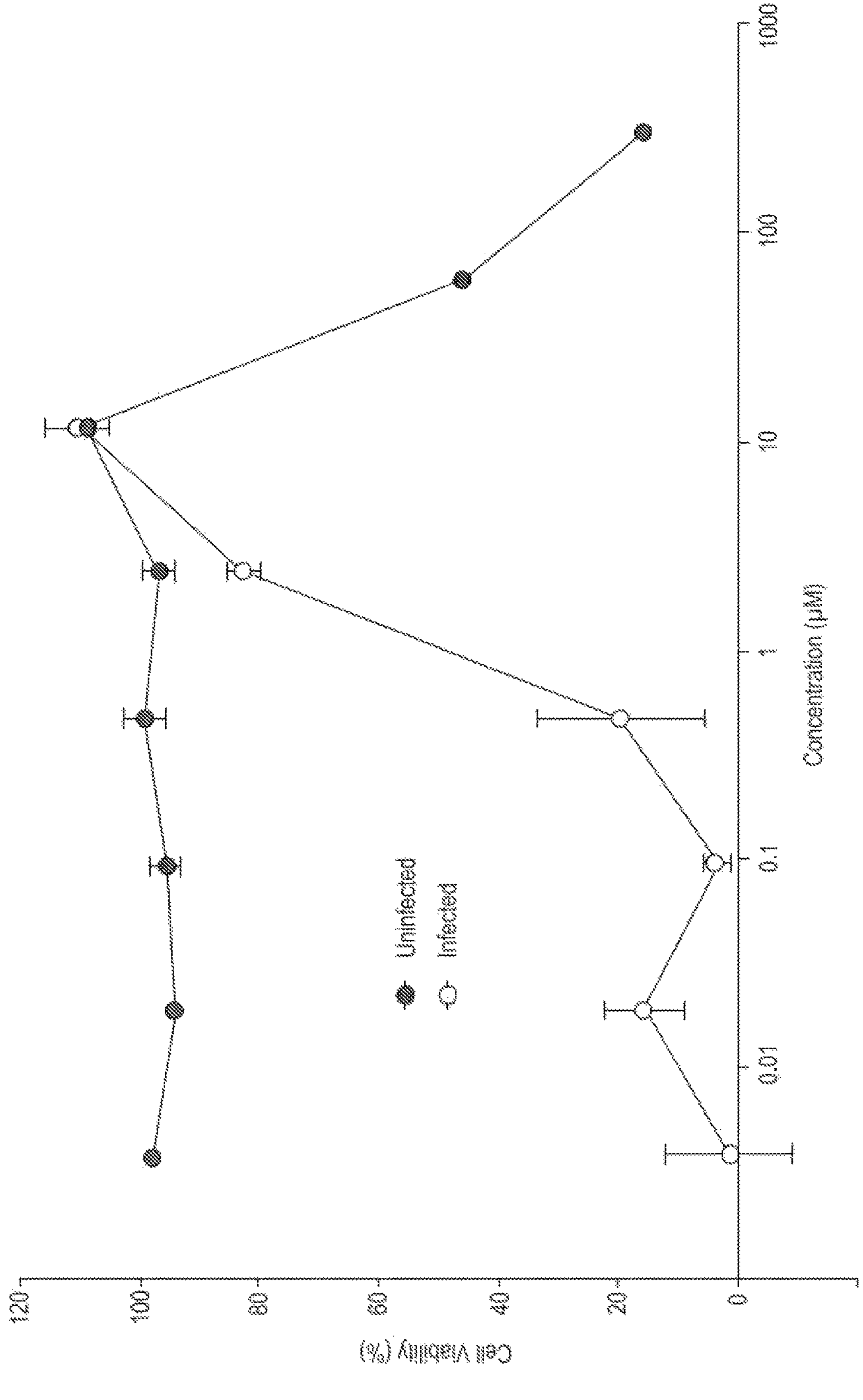
FIG. 6 depicts the effect of Compound 1 on viability of uninfected and HCoV-OC43 infected H292 cells. Data are presented as mean percentage cell viability ±SEM (n=3).

In this experiment, H292 cells were permissible to infection by HCoV-OC43 with cytopathic effects visible in the infected control cells. Good antiviral activity was observed against the β-coronavirus OC43 with all test items. As shown in FIG. 6, the viability of infected H292 cells increased with increased concentrations of Compound 1, while the viability of uninfected cells did not change significantly. Therefore, Compound 1 shows significant antiviral effect against (3-coronavirus OC43 in H292 cells. Similar behavior was observed for chloroquine, sunitinib and remdesivir. As shown in Table 9, all three demonstrated an antiviral effect against (3-coronavirus OC43 in H292 cells.

TABLE 9

| Compound | Cytotoxicity (μM) | Efficacy (μM) |
|---|---|---|
| 1 | 57.72 | 1.432 |
| Chloroquine | 46.04 | 0.3997 |
| Sunitinib | 10-50 | 0.4059 |
| Remdesivir | >20 | 37.48 |

6.6.4. Example 4. In Vitro Effect Against HCoV-OC43 and HCoV-229E Strain on Huh7 Cells and MRC-5 Cells The objective of this study was to evaluate the antiviral activity of test compounds against human coronavirus (HCoV) 229E and OC43 in the cytopathic effect (CPE) assays.

Compound 1 was provided as a dry powder and prepared as 30 mM stock solutions in 100% DMSO solution. Reference compound remdesivir was provided by WuXi AppTec. Compounds were tested at eight concentrations, half-log dilutions, in duplicate for 50% effective concentration ($EC_{50}$) and 50% cytotoxicity concentration ($CC_{50}$) determinations. The final concentration of DMSO in cell culture was 0.5%.

HCoV 229E (ATCC #VR-740) and OC43 (ATCC #VR-1558) were acquired from the ATCC. MRC-5 cells (ATCC #CCL-171) and Huh7 cells were acquired from the ATCC and AppTec, respectively. MRC5 cells were maintained in the Minimum Essential Medium (Sigma #M2279) supplemented with 10% FBS (Hyclone #SV30087.03), 1% L-glutamine (Gibco #25030-081), 1% NEAA (Gibco #11140-050) and 1% penicillin-streptomycin (Hyclone #SV30010). Minimum Essential Medium supplemented with 5% FBS, 1% L-glutamine, 1% NEAA and 1% penicillin-streptomycin was used as the assay medium.

Huh7 cells were maintained in the Dulbecco's Modified Eagle Medium (Gibco #11960-051) supplemented with 10% FBS, 1% L-glutamine, 1% NEAA, and 1% penicillin-streptomycin. The main reagent used in this assay was luminescent cell viability assay kit CellTiter Glo (Promega #G7573). The main instrument used in this assay was Microplate Reader Synergy2 (BioTek).

In 96-well plates, cells were seeded at appropriate densities and cultured at 37° C. and 5% $CO_2$ overnight. Next day, the medium containing serially diluted compounds (8 concentrations, half-log dilutions, in duplicate) was added into cells and incubated at 37° C. and 5% $CO_2$ for 2 hours. Then cells were infected with virus. The resulting cultures were kept at 35° C. (229E) or 33° C. (OC43) and 5% $CO_2$ for additional 3-7 days until that virus infection in the virus control (cells infected with virus, without compound treatment) displays significant CPE. Cell viability was measured with CellTiter Glo according to the manufacturer's manual.

The luminescent signal was measured by Microplate Reader Synergy2 (Molecular Device). The antiviral activity of each compound was calculated based on the inhibition of CPE at each concentration normalized by the virus control.

Cytotoxicity of compounds was assessed under the same conditions but without virus infection, in parallel. Cell viability was measured with CellTiter Glo according to the manufacturer's manual. $CC_{50}$ values were then calculated based on cytotoxicity at the test concentrations normalized by the medium control (medium only).

Antiviral activity and cytotoxicity of compounds were expressed as % inhibition and % cell viability, respectively, and calculated with the formulas below:

$$\text{Inhibition (\%)}=(\text{Raw data}_{CPD}-\text{Average}_{VC})/(\text{Average}_{CC}-\text{Average}_{VC})\times100$$

$$\text{Cell Viability (\%)}=(\text{Raw data}_{CPD}-\text{Average}_{MC})/(\text{Average}_{CC}-\text{Average}_{MC})\times100$$

where the Raw $data_{CPD}$ indicates the values of the compound-treatment wells; $Average_{VC}$, $Average_{CC}$ and $Average_{MC}$ indicate the average values of the virus control, cell control (cells without virus infection or compound treatment) and medium control, respectively.

$EC_{50}$ and $CC_{50}$ values were calculated using GraphPad Prism software (Version 6) and using the equation log (inhibitor) vs. response with variable slope. SI ($CC_{50}/EC_{50}$) was then calculated.

The antiviral experiments were quality controlled with reference compound. Remdesivir showed expected antiviral activity and effect on cell viability, indicating reliability of the experiment. The antiviral and cytotoxic results of the test compounds are summarized in Table 9, wherein SI is $CC_{50}/EC_{50}$.

TABLE 9

| | HCoV 229E CPE assay | | | HCoV OC43 CPE Assay | | |
|---|---|---|---|---|---|---|
| Compound | $EC_{50}$ (μM) | $CC_{50}$ (μM) | SI | $EC_{50}$ (μM) | $CC_{50}$ (μM) | SI |
| 1 | 3.64 | 14.95 | 4.11 | 6.00 | 13.25 | 2.21 |
| Remdesivir | 0.02 | 27.92 | 1327.63 | 0.02 | 6.17 | 276.56 |

Figure 7:
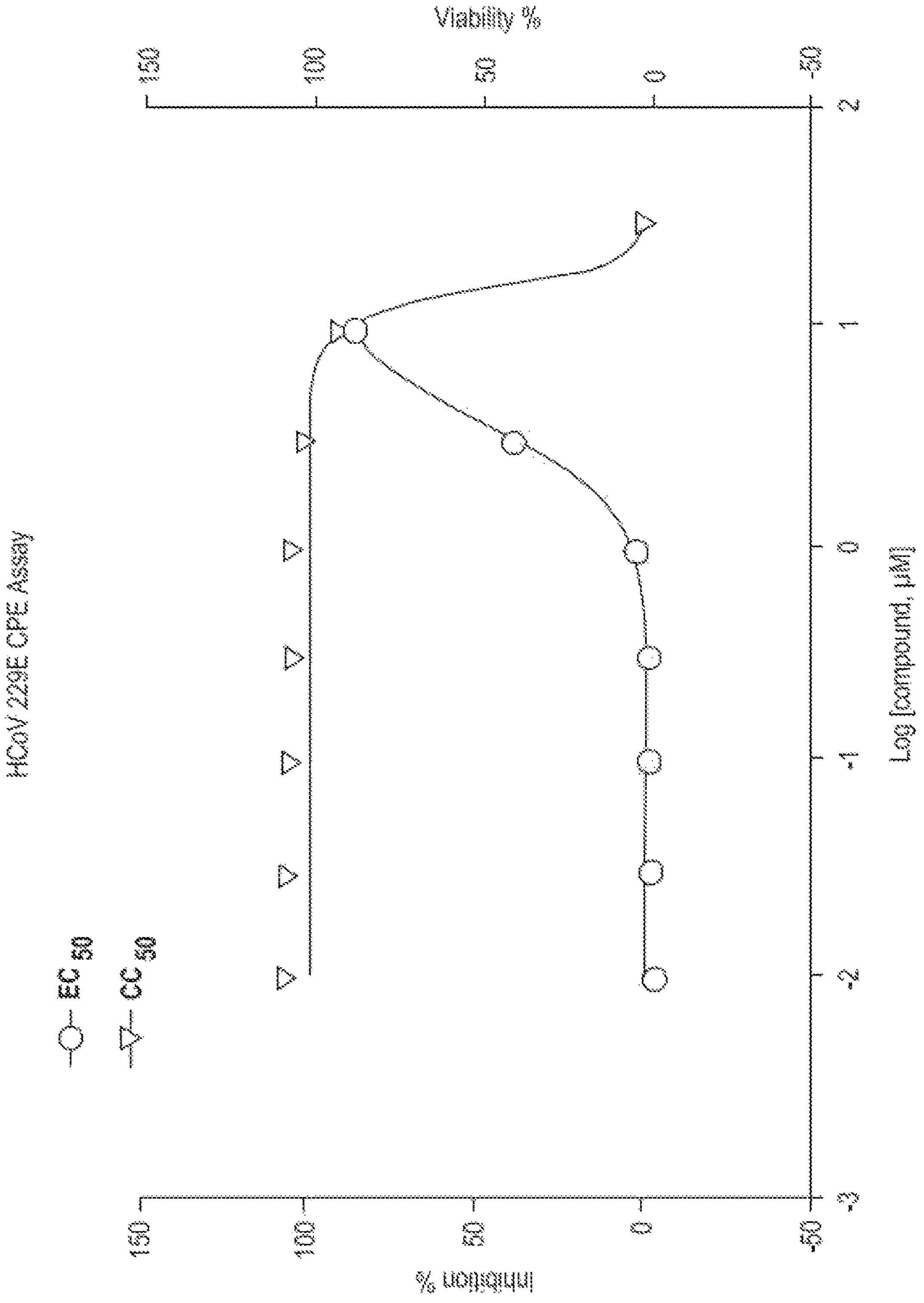
FIG. 7 depicts activity and cytotoxicity curve fitting of Compound 1 in HCoV 229E CPE assay.
Figure 8:
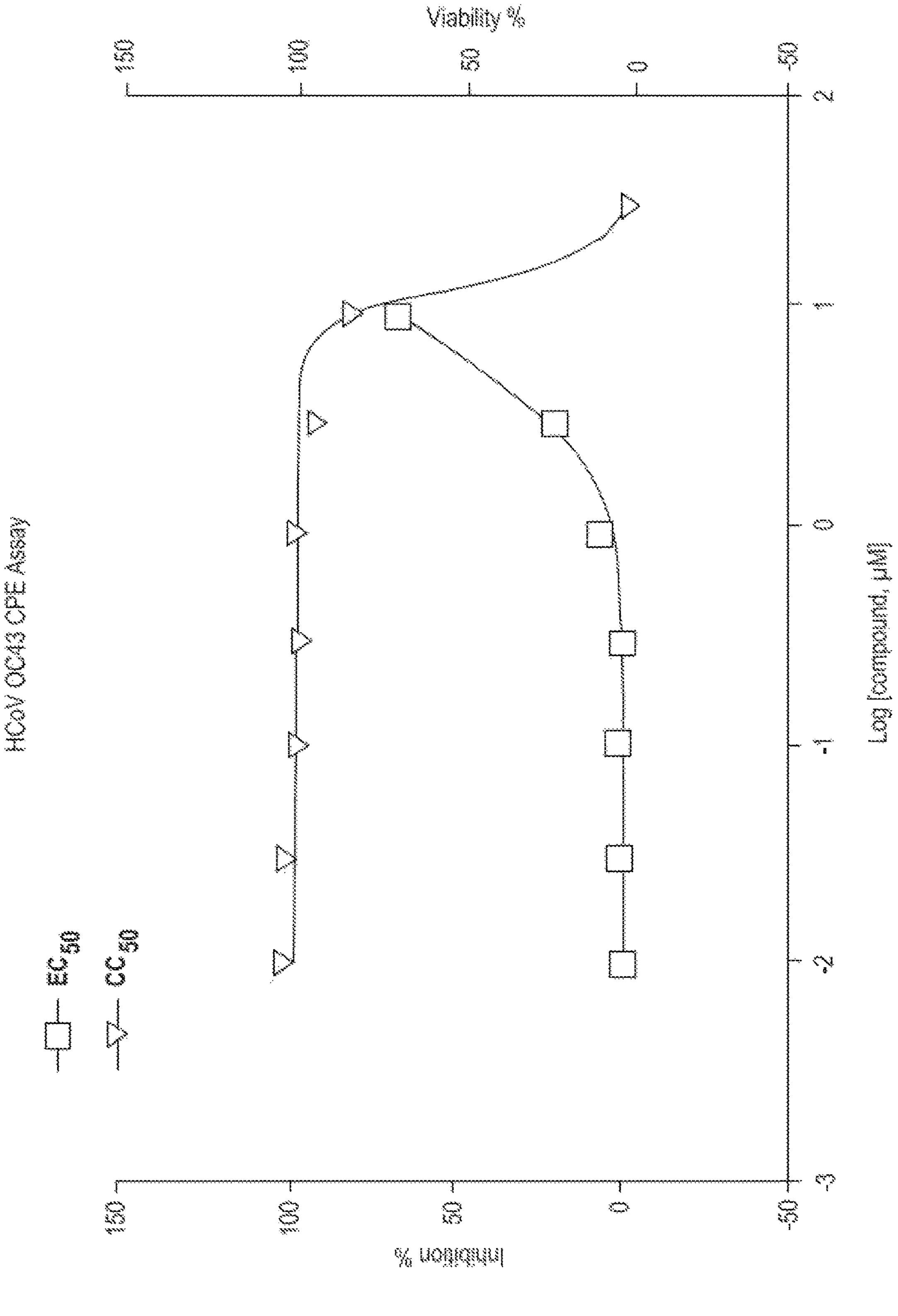
FIG. 8 depicts activity and cytotoxicity curve fitting of Compound 1 in HCoV OC43 CPE assay.

Compound 1 showed inhibitory activities against HCoV 229E with an $EC_{50}$ value of 3.64 μM. Compound 1 showed obvious cytotoxicity on MRC-5 cells with a $CC_{50}$ value of 14.95 μM. Compound 1 showed inhibitory activity against HCoV OC43 with an $EC_{50}$ value of 6.00 μM. Compound 1 showed obvious cytotoxicity on Huh7 cells with a $CC_{50}$ value of 13.25 μM. Inhibition and cytotoxicity curves are shown in FIGS. 7 and 8.

6.6.5. Example 5. In Vitro Effect Against SARS-CoV-2 Strain on VeroE6 Cells

To evaluate antiviral activity against SARS-CoV-2 (USA-WA1/2020), a CPE-based antiviral assay was performed by infecting Vero E6 cells in the presence or absence of test-items. Infection of cells leads to cytopathic effect and cell death after two days of infection. In this assay, reduction of CPE in the presence of inhibitors was used as a surrogate marker to determine the antiviral activity of the tested items. Compound-induced loss of cell viability was determined in parallel using the same readout (CellTiter-Glo®) in uninfected cells.

Vero E6 cells were maintained in DMEM with 10% fetal bovine serum (FBS), hereby called DMEM10. Cells were seeded and incubated for 24 hours before challenged with SARS-CoV-2. The day of infection, samples were first submitted to serial dilutions in a different plate and then added to target cells without changing the cell media. Test-items were incubated with cells for 60 minutes at 37° C. After this period the viral inoculum was added to each well at a multiplicity of infection (m.o.i.) of 0.1. Infection was allowed for 48 h at 37° C. in a humidified incubator. Then, to estimate the virus-induced CPE CellTiter-Glo® Reagent was added to cells and cell viability was estimated by measuring relative light units (RLU) in a plate reader.

Test-items were evaluated in duplicates using serial 2-fold dilutions. Controls included uninfected cells ("mock-infected"), and infected cells to which only vehicle was added. Some wells were also treated with hydroxychloroquine (HCQ) at different concentrations. HCQ is an immunosuppressant and anti-malarial with broad antiviral activity against coronaviruses. Some cells were treated with remdesivir (10 μM). Remdesivir is a broad spectrum antiviral that blocks the RNA polymerase of SARS-CoV-2.

The average relative light units (RLU) observed in infected cells (in the absence of vehicle) was calculated and then subtracted from all samples to determine the inhibition of the virus induced CPE. Data points were then normalized to the average signal observed in uninfected cells (mock) after subtraction of the absorbance signal observed in infected cells. In this assay, uninfected cells remained viable and display high RLU levels. In the absence of antiviral agents the virus-induced CPE kills infected cells and leads to lower RLUs in the cell culture (0% inhibition). By contrast, incubation with the antiviral agent HCQ or remdesivir prevent the virus induced CPE and leads to RLUs similar to those observed in uninfected cells. These values represent 100% inhibition of the virus replication.

The CellTiter-Glo luminescent cell viability assay is a homogeneous method of determining the number of viable cells in culture based on quantitation of the ATP present, an indicator of metabolically active cells. The assay involves adding the reagent directly to cultured cells and generating a luminescent signal proportional to the amount of ATP present, which is directly correlated to the number of cells present in culture. A cytotoxic compound results in lower RLU readouts.

Readout values were given as a percentage of the average signal observed in uninfected cells treated with vehicle alone (tissue culture media). Infected cells developed CPE after two days of infection and displayed significantly reduced RLU levels. As shown in FIG. 9, cell viability was increased compared to vehicle control when cell were treated with Compound 1.

The inhibition of the SARS-CoV-2 (USA-WA1/2020) induced CPE in Vero E6 cells was also measured. Prevention of the virus induced CPE was used as a surrogate marker to determine the extent of replication of SARS-CoV-2. The extent of RLU in infected cells in the presence of vehicle alone is indicative of no inhibition of the virus-induced CPE. Complete inhibition (100%) results in RLU equal to those observed in mock-infected cells (0.01% DMSO). To obtain inhibition values, the average RLU in cells infected in the absence of test-items was subtracted from all values, and then all values were normalized to those obtained for uninfected ("mock) to indicate 100% inhibition. FIG. 10 shows the inhibition of SARS-CoV-2 induced CPE by both Compound 1 and remdesivir. The $IC_{50}$ values for the various compounds were determined as show in FIG. 11, which provides data for Compound 1.

The viability of Vero E6 cells in the CellTiter Glo viability assay as a function of Compound 1 and HCQ concentrations are shown in Table 10. The measured viability of the control (vehicle) was 100.3±0.7.

TABLE 10

| Conc. (μM) | 100 | 50 | 25 | 12.5 | 6.3 | 3.13 | 1.56 |
|---|---|---|---|---|---|---|---|
| Compound 1 | 2.0 ± 0.2 | 17.3 ± 8.4 | 80.7 ± 2.4 | 83.3 ± 1.7 | 86.2 ± 3.2 | 97.1 ± 5.2 | 101.0 ± 5.2 |
| Conc. (μM) | 10 | 5 | 2.5 | 1.25 | 0.63 | 0.31 | 0.16 |
| HCQ | 93.8 ± 6.0 | 93.4 ± 6.5 | 94.4 ± 7.9 | 100.4 ± 0.5 | 103.2 ± 3.4 | 102.3 ± 4.6 | 103.9 ± 6.9 |

Values indicate the percent viability remaining after a 2-day treatment with test-items. Values are shown as percentage of the viability observed in samples incubated with vehicle alone. Data represents the mean and standard deviation of duplicates. Bottom table show the percentage viability observed with medium only control (0.01% DMSO).

As shown in FIG. 12, the viability of Vero E6 cells were not significantly changed by treatment of Compound 1 at concentrations lower than 25 μM or by treatment of HCQ at all concentrations tested. FIG. 13 shows the determination of $CC_{50}$ of Compound 1 measured by Vero E6 cell viability. Table 11 summarizes the $IC_{50}$ and $CC_{50}$ of the compounds tested in this experiment.

TABLE 11

| | Live SARS-CoV-2 Antiviral Assay | | | Cytotoxicity (Vero E6 Cells) | | | |
|---|---|---|---|---|---|---|---|
| Sample | $IC_{50}$ (μM)[1] | Assay S/B* | C.V.[#] | $CC_{50}$ (μM) | S/B* | C.V.[#] | S.I.[2] |
| Compd. 1 | 12.5-25 | 2.1 | 6.4% | 37 | n.d. | 7.6% | n.d. |
| HCQ | ~3 | 2.1 | 6.4% | >10 | n.d. | 7.6% | >3 |

*Signal to background level was calculated by dividing the signal in uninfected cells ("mock-infected"), by the signal in infected cells;
[#]C.V. for the assays was calculated as the average of C.V. values determined for all data points displaying CellTiter Glo readout of 50% or greater for both the antiviral and cytotoxicity assays, as compared to the signal in infected or uninfected cells, respectively;
[1]Exact estimate of the $IC_{50}$ value could not be determined as the dose-response curve did not fit a sigmoidal function due to cell toxicity mediated by Compound 1;
[2]Selectivity Index (S.I.) was determined by dividing $CC_{50}$ by $IC_{50}$ values when possible; and
n.d.: not determined.

$IC_{50}$ (antiviral), and $CC_{50}$ (cytotoxicity) values are shown for Compound 1 and HCQ. Signal-to-background ratios (S/B), and average coefficients of variation (C.V.) of duplicate data-points for which 50s % or greater RLU values were observed, as compared to cells infected in the presence of vehicle alone (CPE assay), or uninfected cells (viability assay). When viral inhibition, or cell viability ($CC_{50}$) did not reach 50% at the highest concentration tested, the $IC_{50}$ or $CC_{50}$ values are shown as greater than the highest concentration tested.

In sum, Compound 1 partially prevented the virus induced cytopathic effect when tested at 25 μM. At this concentration cell viability in the culture reached 80% of the levels observed in uninfected cells. However, the antiviral effect disappeared at higher concentrations, probably due to the compound-induced toxicity present at elevated concentrations in Vero E6 cells, which confounded the ability of Compound 1 to prevent the virus-induced CPE. By comparison, hydroxychloroquine (HCQ) tested at 5 μM, or remdesivir (10 μM) prevented most of the virus-induced CPE, and cell viability levels remained at levels similar to those observed in uninfected cells ("mock").

Compound 1 displayed anti-coronaviral activity against live SARS-CoV-2 at 12.5 μM and 25 μM. However, the toxic properties of the compound prevented the complete inhibition of SARS-CoV-2 replication at higher concentrations. Table 10 summarizes the antiviral and compound-induced-cytotoxicity activities (1050 and $CC_{50}$ values) of the test-items.

Quality controls for the infectivity assays were performed on every plate to determine: i) signal to background (S/B) values; ii) inhibition by a known inhibitor of coronavirus (CPE assay), and iii) variation of the assay, as measured by the coefficient of variation (C.V.) of all data points. All controls worked as anticipated for each assay. Hydroxychloroquine (HCQ), and remdesivir, known inhibitors of SARS-CoV-2, potently prevented the virus-induced CPE in the assay.

Overall variation of duplicates in the antiviral assay was 6.4% and overall variation in the viability assays was 7.6%. The signal-to-background (S/B) for the antiviral assay was 2.1-fold, determined as comparing the RLU values in uninfected cells with that observed in cells challenged with SARS-CoV-2 in the presence of vehicle alone. Signal-to-background (S/B) for the viability assays was not determined.

6.6.6. Example 6 In Vitro Effects Against MERS-CoV Strain on Vero76 Cells

Vero 76 cells permissible to viral infection were seeded at an appropriate concentration into 96 well assay plates and incubated. Serial dilutions of the test items were prepared and added to the cells. M128533, a protease inhibitor was included as the positive control. The cells were then infected with MERS coronavirus (EMC strain) or subjected to mock infection with plain media. Plates were incubated until cytopathic effects (CPE) were seen in the control wells. Cell viability was read microscopically (Visual assay) and by neutral red dye uptake (Neutral Red assay).

In this experiment, Compound 1 inhibited viral infection-induced CPE with an $EC_{50}$ of 6.4 μg/ml and a $CC_{50}$ of 22 μg/ml measured by microscopic visual assay; and an $EC_{50}$ of 5.4 μg/ml and a $CC_{50}$ of 11 μg/ml measured by neutral red assay. The control M128533 inhibited viral infection-induced CPE with an $EC_{50}$ of 5.0 μg/ml and a $CC_{50}$ of >100 μg/ml measured by microscopic visual assay; and an $EC_{50}$ of 5.3 μg/ml and a $CC_{50}$ of >100 μg/ml measured by neutral red assay. These results demonstrate that Compound 1 has an antiviral effect against MERS coronavirus.

6.6.7. Example 7. In Vitro Antiviral Effects Against HBV on HepG2 2.2.15 Cells The primary anti-HBV assay was performed as previously described (see, Korba et al. A cell culture assay for compound which inhibit hepatitis B virus replication. Antiviral Res. 15: 217-228, 1991; and Korba et al., Use of a standardized cell culture assay to assess activities of nucleoside analogs again hepatitis B virus replication. Antiviral Res. 19: 55-70, 1992) with modifications to use real-time qPCR (TaqMan) to measure extracellular HBV DNA copy number associated with virions released from HepG2 2.2.15 cells. The HepG2 2.2.15 cell line is a stable human hepatoblastoma cell line that contains two copies of the HBV wild-type strain ayw1 genome and constitutively produces high levels of HBV. Antiviral compounds blocking any late step of viral replication such as transcription, translation, pregenome encapsidation, reverse transcription, particle assembly and release can be identified and characterized using this cell line.

Briefly, HepG2 2.2.15 cells were plated in 96-well microtiter plates at $1.5\times10^4$ cells/well in Dulbecco's Modified Eagle's Medium supplemented with 2% FBS, 380 μg/mL G418, 2.0 mM L-Glutamine, 100 units/mL Penicillin, 100 μg/mL Streptomycin, and 0.1 mM non-essential amino acids. Only the interior wells were utilized to reduce "edge effects" observed during cell culture; the exterior wells were filled with complete medium to help minimize sample evaporation. After 16-24 hours the confluent monolayer of HepG2 2.2.15 cells was washed and the medium was replaced with complete medium containing various concentrations of a test compound in triplicate. Lamivudine (3TC) was used as the positive control, while media alone was added to cells as a negative control (virus control, VC). Three days later the culture medium was replaced with fresh medium containing the appropriately diluted test compounds. Six days following the initial administration of the test compound, the cell culture supernatant was collected, treated with pronase and then used in a real-time quantitative TaqMan qPCR assay. The PCR-amplified HBV DNA was detected in real-time by monitoring increases in fluorescent signal that result from the exonucleolytic degradation of a quenched fluorescent probe molecule that hybridizes to the amplified HBV DNA. For each PCR amplification, a standard curve was simultaneously generated using dilutions of purified HBV DNA.

Antiviral activity was calculated from the reduction in HBV DNA levels ($EC_{50}$ & $EC_{90}$ values determined). A tetrazolium dye (MTS; 3-(4,5-dimethylthiazol-2-yl)-5-(3-carboxymethoxyphenyl)-2-(4-sulfophenyl)-2H-tetrazolium; Cell Titer®96 Reagent, Promega) uptake assay was then employed to measure cell viability using the same assay plate, and the viability data was used to calculate compound cytotoxicity ($CC_{50}$). The Selectivity Index (S150) is calculated as $CC_{50}/EC_{50}$.

The secondary anti-HBV assay was performed in a manner similar to the primary assay described above; however, at the end of the assay, the cells were processed to isolate total intracellular DNA using the Qiagen DNeasy Blood and Tissue kit following the manufacturer's protocol. The real-time TaqMan qPCR assay was then performed using the isolated DNA to measure reductions in intracellular HBV DNA copy number. In addition, since the cells were harvested to collect intracellular DNA, a separate duplicate plate was processed to evaluate compound cytotoxicity. The results from the secondary assay were used to determine if reductions in extracellular HBV DNA copy number observed in the primary assay correlate to a concomitant reduction in intracellular HBV DNA copy number. The secondary anti-HBV assay was used to confirm potential antiviral activity identified in the primary assay, meanwhile, may provide insights into mode of action of the active compounds.

As shown in Table 12, Compound 1 demonstrated an antiviral effect against HBV with an $EC_{50}$ of 6.35 μM, and a $CC_{50}$ of 29.33. The concentration ranges tested were: Compound 1=0.001-100 μM; Entecavir=0.00001-1.00 μM; 3TC=0.006-2 μM.

TABLE 12

| Compound | $EC_{50}$ (μM) | $EC_{90}$ (μM) | $CC_{50}$ (μM) | $SI_{50}$ | $SI_{90}$ |
|---|---|---|---|---|---|
| 1 | 6.35 | >100.00 | 29.33 | 5 | <1 |
| Entecavir | 0.00044 | >1.00 | >1.00 | >2,273 | 1 |
| 3TC | 0.02827 | >2.00 | >2.00 | >71 | 1 |

6.6.8. Example 8. In Vitro Antiviral Effects of Compound 1 Against Dengue Virus on Vero76 Cells Measured by Immunostaining The antiviral activity of Compound 1 against two dengue virus (DENV) serotype 2 strains (D2Y98P and D2S221) was measured by the concentration of Compound 1 that inhibits 50% virus infectivity ($IC_{50}$) for each strain.

A cytopathic (CPE)-based inhibition assay was conducted in Vero cells. Eight three-fold serial dilutions of test items in triplicate was evaluated against D2Y98P and D2S221. Infection was assessed by immuno-staining and the 50% inhibition dose (ID50) of each test item was determined using "virus-only" and "cells only" as 0% and 100% inhibition respectively.

Vero cells (passage 26) were seeded in 96-well plates at $1\times10^4$ cells/well and incubated overnight at 37° C. and 5% $CO_2$ in MEM supplemented with 10% HI-FBS, 1×P/S and 2 mM L-Gln one day prior.

Eight three-fold dilutions of the each test item were prepared in triplicate in MEM supplemented with 2% HI-FBS, 1×P/S and 2 mM L-Gln in 96-well V-bottom plate for a final starting concentration at 100 μM. Medium was then removed from the 96-well culture plate containing Vero cells and 50 μL of test item was transferred with 50 μL of fresh MEM supplemented with 2% HI-FBS, 1×P/S and 2 mM L-Gln; cells were incubated at 37° C. for 60±5 minutes. 100 μL of virus prepared in MEM supplemented with 2% HI-FBS, 1×P/S and 2 mM L-Gln was then added in each well; MOI of 0.05 for D2Y98P and MOI of 0.08 for D2S221. Virus only without antibody was also added to serve as the baseline control was prepared and plates were incubated at 37° C. and 5% $CO_2$ for 4 or 5 days.

The cells were fixed with ethanol/methanol for 30 minutes at −20° C., then the cells were washed 3× with DPBS before to remove the alcohol solution and cells were blocked by addition of 5% dry nonfat milk prepared in 1×DPBS (blocking buffer) for 30 minutes. Blocking buffer was removed from wells and 100 μL of the diluted primary antibody, 4G2 (1:2,000 in blocking buffer) was added to each well for two hours incubation at room temperature. Plates were washed three times with 1×DPBS. The secondary antibody, Goat Anti-Mouse IgG (H+L)-HRP Conjugate, was diluted 1:2,000 in blocking buffer and 100p L was added to each well for 1-hour incubation at room temperature. The secondary antibody was removed, and the plates were washed three times with 1×DPBS. TrueBlue peroxidase substrate (150 μL/well) was added for approximately 10 minutes (until plaques are visualized). The Bioreader 6000-Vα was used to count plaques.

Data were imported into Excel to calculate the ID50 values. The XLfit 5 plug-in was used with fit #205 (Levenberg-Marquardt algorithm) setting virus-only as 0% efficacy.

As shown in Table 13, Compound 1 demonstrated antiviral effects against both strains of Dengue virus D2Y98P and D2S221, with $IC_{50}$ values of 7.088 μM and 6.66 μM, respectively.

TABLE 13

| Compound | D2Y98P (μM) | D2S221 (μM) |
|---|---|---|
| Compound 1 | 7.088 | 6.66 |
| Chloroquine diphosphate | 11.73 | 23.72 |
| Sunitinib | 5.652 | 4.056 |
| Ribavirin (control) | 120.1 | 71.11 |

In the cytotoxicity assay, Vero cells (passage 24) were seeded in 96-well black plates at $1\times10^4$ cells/well and incubated overnight at 37° C. and 5% $CO_2$ in MEM supplemented with 10% HI-FBS, 1×P/S and 2 mM L-Gln; the last column will remain cell-free to evaluate assay background (background wells)

Eight three-fold dilutions of the each test item were prepared in triplicate in MEM supplemented with 10% HI-FBS, 1×P/S and 2 mM L-Gln in 96-well V-bottom plate for a final starting concentration at 100 μM. Medium was then removed from the 96-well black plate containing Vero cells and 50 μL of test item was transferred with 150 μL of fresh medium; a full column of "cell-only" was also included. Cells were incubated at 37° C. for four days.

Culture medium was removed from the 96-well black plates and 100 μl of CellTiter-Glo® reagent (Promega, Cat #G7570) to all wells except the background wells (last column of each plate). 100 μl of 1×DPBS was then added to all wells except the background wells. Luminescence was read using the Biotek plate reader (Imaging multi-mode reader, Biotek, Cat #Cytation 5)

FIGS. 14-17 provide graphical presentations of the data. The $CC_{50}$ of Compound 1 was found to be 13.51 μM.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Each of the references disclosed herein is incorporated herein in its entirety.

What is claimed is:

1. A method of treating or managing a SARS-CoV-2-like coronavirus infection, the method comprising administering to a subject in need thereof a therapeutically effective amount of a compound, wherein the compound is (S)-1-((2',6-bis(difluoromethyl)-[2,4'-bipyridin]-5-yl)oxy)-2,4-dimethylpentan-2-amine:

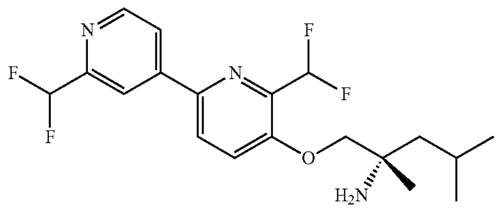 [SMILES: CC(C)C[C@](C)(N)COc1ccc(-c2ccnc(C(F)F)c2)nc1C(F)F]

or a pharmaceutically acceptable salt thereof.

2. A method of treating or managing a CoV-229E-like coronavirus infection, the method comprising administering to a subject in need thereof a therapeutically effective amount of a compound, wherein the compound is (S)-1-((2',6-bis(difluoromethyl)-[2,4'-bipyridin]-5-yl)oxy)-2,4-dimethylpentan-2-amine:

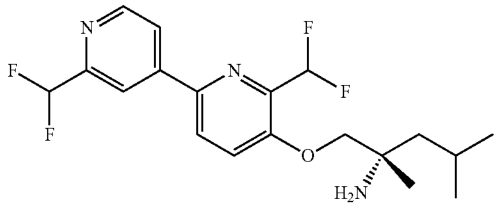 [SMILES: CC(C)C[C@](C)(N)COc1ccc(-c2ccnc(C(F)F)c2)nc1C(F)F]

or a pharmaceutically acceptable salt thereof.

3. A method of treating or managing a CoV-OC43-like coronavirus infection, the method comprising administering to a subject in need thereof a therapeutically effective amount of a compound, wherein the compound is (S)-1-((2',6-bis(difluoromethyl)-[2,4'-bipyridin]-5-yl)oxy)-2,4-dimethylpentan amine:

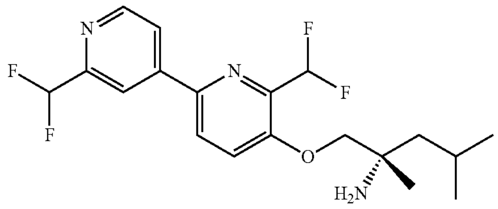 [SMILES: CC(C)C[C@](C)(N)COc1ccc(-c2ccnc(C(F)F)c2)nc1C(F)F]

or a pharmaceutically acceptable salt thereof.

* * * * *

SEQUENCE LISTING

```
<160> NUMBER OF SEQ ID NOS: 12

<210> SEQ ID NO 1
<211> LENGTH: 29903
<212> TYPE: DNA
<213> ORGANISM: Severe acute respiratory syndrome coronavirus 2

<400> SEQUENCE: 1

attaaaggtt tataccttcc caggtaacaa accaaccaac tttcgatctc ttgtagatct      60

gttctctaaa cgaactttaa aatctgtgtg gctgtcactc ggctgcatgc ttagtgcact     120

cacgcagtat aattaataac taattactgt cgttgacagg acacgagtaa ctcgtctatc     180

ttctgcaggc tgcttacggt ttcgtccgtg ttgcagccga tcatcagcac atctaggttt     240

cgtccgggtg tgaccgaaag gtaagatgga gagccttgtc cctggtttca acgagaaaac     300

acacgtccaa ctcagtttgc ctgttttaca ggttcgcgac gtgctcgtac gtggctttgg     360

agactccgtg gaggaggtct tatcagaggc acgtcaacat cttaaagatg gcacttgtgg     420

cttagtagaa gttgaaaaag gcgttttgcc tcaacttgaa cagccctatg tgttcatcaa     480

acgttcggat gctcgaactg cacctcatgg tcatgttatg gttgagctgg tagcagaact     540

cgaaggcatt cagtacggtc gtagtggtga gacacttggt gtccttgtcc ctcatgtggg     600

cgaaatacca gtggcttacc gcaaggttct tcttcgtaag aacggtaata aaggagctgg     660

tggccatagt tacggcgccg atctaaagtc atttgactta ggcgacgagc ttggcactga     720

tccttatgaa gattttcaag aaaactggaa cactaaacat agcagtggtg ttacccgtga     780

actcatgcgt gagcttaacg gaggggcata cactcgctat gtcgataaca acttctgtgg     840

ccctgatggc taccctcttg agtgcattaa agaccttcta gcacgtgctg gtaaagcttc     900

atgcactttg tccgaacaac tggactttat tgacactaag aggggtgtat actgctgccg     960

tgaacatgag catgaaattg cttggtacac ggaacgttct gaaaagagct atgaattgca    1020

gacacctttt gaaattaaat tggcaaagaa atttgacacc ttcaatgggg aatgtccaaa    1080

ttttgtattt cccttaaatt ccataatcaa gactattcaa ccaagggttg aaaagaaaaa    1140

gcttgatggc tttatgggta gaattcgatc tgtctatcca gttgcgtcac caaatgaatg    1200

caaccaaatg tgcctttcaa ctctcatgaa gtgtgatcat tgtggtgaaa cttcatggca    1260

gacgggcgat tttgttaaag ccacttgcga attttgtggc actgagaatt tgactaaaga    1320

aggtgccact acttgtggtt acttacccca aaatgctgtt gttaaaattt attgtccagc    1380

atgtcacaat tcagaagtag gacctgagca tagtcttgcc gaataccata atgaatctgg    1440
```

-continued

```
cttgaaaacc attcttcgta agggtggtcg cactattgcc tttggaggct gtgtgttctc   1500
ttatgttggt tgccataaca agtgtgccta ttgggttcca cgtgctagcg ctaacatagg   1560
ttgtaaccat acaggtgttg ttggagaagg ttccgaaggt cttaatgaca accttcttga   1620
aatactccaa aaagagaaag tcaacatcaa tattgttggt gactttaaac ttaatgaaga   1680
gatcgccatt attttggcat ctttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
agaaggtgat tgtgaagaag aagagtttga gccatcaact caatatgagt atggtactga   3120
agatgattac caaggtaaac ctttggaatt tggtgccact tctgctgctc ttcaacctga   3180
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
agagatggaa cttacaccag ttgttcagac tattgaagtg aatagtttta gtggttattt   3360
aaaacttact gacaatgtat acattaaaaa tgcagacatt gtggaagaag ctaaaaaggt   3420
aaaaccaaca gtggttgtta atgcagccaa tgtttacctt aaacatggag gaggtgttgc   3480
aggagcctta aataaggcta ctaacaatgc catgcaagtt gaatctgatg attacatagc   3540
tactaatgga ccacttaaag tgggtggtag ttgtgtttta agcggacaca atcttgctaa   3600
acactgtctt catgttgtcg gcccaaatgt taacaaaggt gaagacattc aacttcttaa   3660
gagtgcttat gaaaatttta atcagcacga agttctactt gcaccattat tatcagctgg   3720
tatttttggt gctgacccta tacattcttt aagagtttgt gtagatactg ttcgcacaaa   3780
tgtctactta gctgtctttg ataaaaatct ctatgacaaa cttgtttcaa gctttttgga   3840
```

```
aatgaagagt gaaaagcaag ttgaacaaaa gatcgctgag attcctaaag aggaagttaa   3900
gccatttata actgaaagta aaccttcagt tgaacagaga aaacaagatg ataagaaaat   3960
caaagcttgt gttgaagaag ttacaacaac tctggaagaa actaagttcc tcacagaaaa   4020
cttgttactt tatattgaca ttaatggcaa tcttcatcca gattctgcca ctcttgttag   4080
tgacattgac atcactttct taaagaaaga tgctccatat atagtgggtg atgttgttca   4140
agagggtgtt ttaactgctg tggttatacc tactaaaaag gctggtggca ctactgaaat   4200
gctagcgaaa gctttgagaa aagtgccaac agacaattat ataaccactt acccgggtca   4260
gggtttaaat ggttacactg tagaggaggc aaagacagtg cttaaaaagt gtaaaagtgc   4320
cttttacatt ctaccatcta ttatctctaa tgagaagcaa gaaattcttg gaactgtttc   4380
ttggaatttg cgagaaatgc ttgcacatgc agaagaaaca cgcaaattaa tgcctgtctg   4440
tgtggaaact aaagccatag tttcaactat acagcgtaaa tataagggta ttaaaataca   4500
agagggtgtg gttgattatg gtgctagatt ttacttttac accagtaaaa caactgtagc   4560
gtcacttatc aacacactta acgatctaaa tgaaactctt gttacaatgc cacttggcta   4620
tgtaacacat ggcttaaatt tggaagaagc tgctcggtat atgagatctc tcaaagtgcc   4680
agctacagtt tctgtttctt cacctgatgc tgttacagcg tataatggtt atcttacttc   4740
ttcttctaaa acacctgaag aacattttat tgaaaccatc tcacttgctg gttcctataa   4800
agattggtcc tattctggac aatctacaca actaggtata gaatttctta agagaggtga   4860
taaaagtgta tattacacta gtaatcctac cacattccac ctagatggtg aagttatcac   4920
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc cacaagttaa tggtttaact tctattaaat gggcagataa   5280
caactgttat cttgccactg cattgttaac actccaacaa atagagttga agtttaatcc   5340
acctgctcta caagatgctt attacagagc aagggctggt gaagctgcta acttttgtgc   5400
acttatctta gcctactgta ataagacagt aggtgagtta ggtgatgtta gagaaacaat   5460
gagttacttg tttcaacatg ccaatttaga ttcttgcaaa agagtcttga acgtggtgtg   5520
taaaacttgt ggacaacagc agacaaccct taagggtgta gaagctgtta tgtacatggg   5580
cacactttct tatgaacaat ttaagaaagg tgttcagata ccttgtacgt gtggtaaaca   5640
agctacaaaa tatctagtac aacaggagtc accttttgtt atgatgtcag caccacctgc   5700
tcagtatgaa cttaagcatg gtacatttac ttgtgctagt gagtacactg gtaattacca   5760
gtgtggtcac tataaacata taacttctaa agaaactttg tattgcatag acggtgcttt   5820
acttacaaag tcctcagaat acaaaggtcc tattacggat gttttctaca aagaaaacag   5880
ttacacaaca accataaaac cagttactta taaattggat ggtgttgttt gtacagaaat   5940
tgaccctaag ttggacaatt attataagaa agacaattct tatttcacag agcaaccaat   6000
tgatcttgta ccaaaccaac catatccaaa cgcaagcttc gataatttta agtttgtatg   6060
tgataatatc aaatttgctg atgatttaaa ccagttaact ggttataaga aacctgcttc   6120
aagagagctt aaagttacat tttccctga cttaaatggt gatgtggtgg ctattgatta    6180
```

-continued

```
taaacactac acaccctctt ttaagaaagg agctaaattg ttacataaac ctattgtttg   6240
gcatgttaac aatgcaacta ataaagccac gtataaacca aatacctggt gtatacgttg   6300
tctttggagc acaaaaccag ttgaaacatc aaattcgttt gatgtactga agtcagagga   6360
cgcgcaggga atggataatc ttgcctgcga agatctaaaa ccagtctctg aagaagtagt   6420
ggaaaatcct accatacaga aagacgttct tgagtgtaat gtgaaaacta ccgaagttgt   6480
aggagacatt atacttaaac cagcaaataa tagtttaaaa attacagaag aggttggcca   6540
cacagatcta atggctgctt atgtagacaa ttctagtctt actattaaga aacctaatga   6600
attatctaga gtattaggtt tgaaaaccct tgctactcat ggtttagctg ctgttaatag   6660
tgtcccttgg gatactatag ctaattatgc taagcctttt cttaacaaag ttgttagtac   6720
aactactaac atagttacac ggtgtttaaa ccgtgtttgt actaattata tgccttattt   6780
ctttacttta ttgctacaat tgtgtacttt tactagaagt acaaattcta gaattaaagc   6840
atctatgccg actactatag caaagaatac tgttaagagt gtcggtaaat tttgtctaga   6900
ggcttcattt aattatttga agtcacctaa tttttctaaa ctgataaata ttataatttg   6960
gtttttacta ttaagtgttt gcctaggttc tttaatctac tcaaccgctg ctttaggtgt   7020
tttaatgtct aatttaggca tgccttctta ctgtactggt tacagagaag gctatttgaa   7080
ctctactaat gtcactattg caacctactg tactggttct ataccttgta gtgtttgtct   7140
tagtggttta gattctttag acacctatcc ttctttagaa actatacaaa ttaccatttc   7200
atcttttaaa tgggatttaa ctgcttttgg cttagttgca gagtggtttt tggcatatat   7260
tcttttcact aggtttttct atgtacttgg attggctgca atcatgcaat tgtttttcag   7320
ctattttgca gtacatttta ttagtaattc ttggcttatg tggttaataa ttaatcttgt   7380
acaaatggcc ccgatttcag ctatggttag aatgtacatc ttctttgcat cattttatta   7440
tgtatggaaa agttatgtgc atgttgtaga cggttgtaat tcatcaactt gtatgatgtg   7500
ttacaaacgt aatagagcaa caagagtcga atgtacaact attgttaatg gtgttagaag   7560
gtccttttat gtctatgcta atggaggtaa aggcttttgc aaactacaca attggaattg   7620
tgttaattgt gatacattct gtgctggtag tacatttatt agtgatgaag ttgcgagaga   7680
cttgtcacta cagtttaaaa gaccaataaa tcctactgac cagtcttctt acatcgttga   7740
tagtgttaca gtgaagaatg gttccatcca tctttacttt gataaagctg gtcaaaagac   7800
ttatgaaaga cattctctct ctcattttgt taacttagac aacctgagag ctaataacac   7860
taaaggttca ttgcctatta atgttatagt ttttgatggt aaatcaaaat gtgaagaatc   7920
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta aagatgttgt   8220
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
tgctaaaaag aataacttac cttttaagtt gacatgtgca actactagac aagttgttaa   8520
tgttgtaaca acaaagatag cacttaaggg tggtaaaatt gttaataatt ggttgaagca   8580
```

-continued

```
gttaattaaa gttacacttg tgttcctttt tgttgctgct attttctatt taataacacc   8640
tgttcatgtc atgtctaaac atactgactt ttcaagtgaa atcataggat acaaggctat   8700
tgatggtggt gtcactcgtg acatagcatc tacagatact tgttttgcta acaaacatgc   8760
tgattttgac acatggttta gccagcgtgg tggtagttat actaatgaca aagcttgccc   8820
attgattgct gcagtcataa caagagaagt gggttttgtc gtgcctggtt tgcctggcac   8880
gatattacgc acaactaatg gtgacttttt gcatttctta cctagagttt ttagtgcagt   8940
tggtaacatc tgttacacac catcaaaact tatagagtac actgactttg caacatcagc   9000
ttgtgttttg gctgctgaat gtacaatttt taaagatgct tctggtaagc cagtaccata   9060
ttgttatgat accaatgtac tagaaggttc tgttgcttat gaaagtttac gccctgacac   9120
acgttatgtg ctcatggatg gctctattat tcaatttcct aacacctacc ttgaaggttc   9180
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttattt acttgtactt   9600
gacattttat cttactaatg atgtttcttt tttagcacat attcagtgga tggttatgtt   9660
cacaccttta gtacctttct ggataacaat tgcttatatc atttgtattt ccacaaagca   9720
tttctattgg ttctttagta attacctaaa gagacgtgta gtctttaatg gtgtttcctt   9780
tagtactttt gaagaagctg cgctgtgcac ctttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
```

-continued

```
tgaatttaca cctttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
```

acctacaact tgtgctaatg accctgtggg ttttacactt aaaaacacag tctgtaccgt 13380
ctgcggtatg tggaaaggtt atggctgtag ttgtgatcaa ctccgcgaac ccatgcttca 13440
gtcagctgat gcacaatcgt ttttaaacgg gtttgcggtg taagtgcagc ccgtcttaca 13500
ccgtgcggca caggcactag tactgatgtc gtatacaggg cttttgacat ctacaatgat 13560
aaagtagctg gttttgctaa attcctaaaa actaattgtt gtcgcttcca agaaaaggac 13620
gaagatgaca atttaattga ttcttacttt gtagttaaga gacacacttt ctctaactac 13680
caacatgaag aaacaattta taatttactt aaggattgtc cagctgttgc taaacatgac 13740
ttctttaagt ttagaataga cggtgacatg gtaccacata tatcacgtca acgtcttact 13800
aaatacacaa tggcagacct cgtctatgct ttaaggcatt ttgatgaagg taattgtgac 13860
acattaaaag aaatacttgt cacatacaat tgttgtgatg atgattattt caataaaaag 13920
gactggtatg attttgtaga aaacccagat atattacgcg tatacgccaa cttaggtgaa 13980
cgtgtacgcc aagctttgtt aaaaacagta caattctgtg atgccatgcg aaatgctggt 14040
attgttggtg tactgacatt agataatcaa gatctcaatg gtaactggta tgatttcggt 14100
gatttcatac aaaccacgcc aggtagtgga gttcctgttg tagattctta ttattcattg 14160
ttaatgccta tattaacctt gaccagggct ttaactgcag agtcacatgt tgacactgac 14220
ttaacaaagc cttacattaa gtgggatttg ttaaaatatg acttcacgga agagaggtta 14280
aaactctttg accgttattt taaatattgg gatcagacat accacccaaa ttgtgttaac 14340
tgtttggatg acagatgcat tctgcattgt gcaaacttta atgttttatt ctctacagtg 14400
ttcccaccta caagttttgg accactagtg agaaaaatat ttgttgatgg tgttccattt 14460
gtagtttcaa ctggatacca cttcagagag ctaggtgttg tacataatca ggatgtaaac 14520
ttacatagct ctagacttag ttttaaggaa ttacttgtgt atgctgctga ccctgctatg 14580
cacgctgctt ctggtaatct attactagat aaacgcacta cgtgcttttc agtagctgca 14640
cttactaaca atgttgcttt tcaaactgtc aaacccggta attttaacaa agacttctat 14700
gactttgctg tgtctaaggg tttctttaag gaaggaagtt ctgttgaatt aaaacacttc 14760
ttctttgctc aggatggtaa tgctgctatc agcgattatg actactatcg ttataatcta 14820
ccaacaatgt gtgatatcag acaactacta tttgtagttg aagttgttga taagtacttt 14880
gattgttacg atggtggctg tattaatgct aaccaagtca tcgtcaacaa cctagacaaa 14940
tcagctggtt ttccatttaa taaatggggt aaggctagac tttattatga ttcaatgagt 15000
tatgaggatc aagatgcact tttcgcatat acaaaacgta atgtcatccc tactataact 15060
caaatgaatc ttaagtatgc cattagtgca aagaatagag ctcgcaccgt agctggtgtc 15120
tctatctgta gtactatgac caatagacag tttcatcaaa aattattgaa atcaatagcc 15180
gccactagag gagctactgt agtaattgga acaagcaaat tctatggtgg ttggcacaac 15240
atgttaaaaa ctgtttatag tgatgtagaa aaccctcacc ttatgggttg ggattatcct 15300
aaatgtgata gagccatgcc taacatgctt agaattatgg cctcacttgt tcttgctcgc 15360
aaacatacaa cgtgttgtag cttgtcacac cgtttctata gattagctaa tgagtgtgct 15420
caagtattga gtgaaatggt catgtgtggc ggttcactat atgttaaacc aggtggaacc 15480
tcatcaggag atgccacaac tgcttatgct aatagtgttt ttaacatttg tcaagctgtc 15540
acggccaatg ttaatgcact tttatctact gatggtaaca aaattgccga taagtatgtc 15600
cgcaatttac aacacagact ttatgagtgt ctctatagaa atagagatgt tgacacagac 15660

```
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
```

```
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
```

-continued

```
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attacccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
```

-continued gcaaactgga aagattgctg attataatta taaattacca gatgatttta caggctgcgt 22860
tatagcttgg aattctaaca atcttgattc taaggttggt ggtaattata attacctgta 22920
tagattgttt aggaagtcta atctcaaacc ttttgagaga gatatttcaa ctgaaatcta 22980
tcaggccggt agcacacctt gtaatggtgt tgaaggtttt aattgttact ttcctttaca 23040
atcatatggt ttccaaccca ctaatggtgt tggttaccaa ccatacagag tagtagtact 23100
ttcttttgaa cttctacatg caccagcaac tgtttgtgga cctaaaaagt ctactaattt 23160
ggttaaaaac aaatgtgtca atttcaactt caatggttta acaggcacag gtgttcttac 23220
tgagtctaac aaaaagtttc tgcctttcca acaatttggc agagacattg ctgacactac 23280
tgatgctgtc cgtgatccac agacacttga gattcttgac attacaccat gttcttttgg 23340
tggtgtcagt gttataacac caggaacaaa tacttctaac caggttgctg ttctttatca 23400
ggatgttaac tgcacagaag tccctgttgc tattcatgca gatcaactta ctcctacttg 23460
gcgtgtttat tctacaggtt ctaatgtttt tcaaacacgt gcaggctgtt taataggggc 23520
tgaacatgtc aacaactcat atgagtgtga catacccatt ggtgcaggta tatgcgctag 23580
ttatcagact cagactaatt ctcctcggcg ggcacgtagt gtagctagtc aatccatcat 23640
tgcctacact atgtcacttg gtgcagaaaa ttcagttgct tactctaata actctattgc 23700
catacccaca aattttacta ttagtgttac cacagaaatt ctaccagtgt ctatgaccaa 23760
gacatcagta gattgtacaa tgtacatttg tggtgattca actgaatgca gcaatctttt 23820
gttgcaatat ggcagttttt gtacacaatt aaaccgtgct ttaactggaa tagctgttga 23880
acaagacaaa aacacccaag aagtttttgc acaagtcaaa caaatttaca aaacaccacc 23940
aattaaagat tttggtggtt ttaatttttc acaaatatta ccagatccat caaaaccaag 24000
caagaggtca tttattgaag atctactttt caacaaagtg acacttgcag atgctggctt 24060
catcaaacaa tatggtgatt gccttggtga tattgctgct agagacctca tttgtgcaca 24120
aaagtttaac ggccttactg ttttgccacc tttgctcaca gatgaaatga ttgctcaata 24180
cacttctgca ctgttagcgg gtacaatcac ttctggttgg acctttggtg caggtgctgc 24240
attacaaata ccatttgcta tgcaaatggc ttataggttt aatggtattg gagttacaca 24300
gaatgttctc tatgagaacc aaaaattgat tgccaaccaa tttaatagtg ctattggcaa 24360
aattcaagac tcactttctt ccacagcaag tgcacttgga aaacttcaag atgtggtcaa 24420
ccaaaatgca caagctttaa acacgcttgt taaacaactt agctccaatt ttggtgcaat 24480
ttcaagtgtt ttaaatgata tcctttcacg tcttgacaaa gttgaggctg aagtgcaaat 24540
tgataggttg atcacaggca gacttcaaag tttgcagaca tatgtgactc aacaattaat 24600
tagagctgca gaaatcagag cttctgctaa tcttgctgct actaaaatgt cagagtgtgt 24660
acttggacaa tcaaaaagag ttgatttttg tggaaagggc tatcatctta tgtccttccc 24720
tcagtcagca cctcatggtg tagtcttctt gcatgtgact tatgtccctg cacaagaaaa 24780
gaacttcaca actgctcctg ccatttgtca tgatggaaaa gcacactttc ctcgtgaagg 24840
tgtctttgtt tcaaatggca cacactggtt tgtaacacaa aggaattttt atgaaccaca 24900
aatcattact acagacaaca catttgtgtc tggtaactgt gatgttgtaa taggaattgt 24960
caacaacaca gtttatgatc ctttgcaacc tgaattagac tcattcaagg aggagttaga 25020
taaatatttt aagaatcata catcaccaga tgttgattta ggtgacatct ctggcattaa 25080
tgcttcagtt gtaaacattc aaaaagaaat tgaccgcctc aatgaggttg ccaagaattt 25140

```
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
ctgcaaattt gatgaagacg actctgagcc agtgctcaaa ggagtcaaat tacattacac  25380
ataaacgaac ttatggattt gtttatgaga atcttcacaa ttggaactgt aactttgaag  25440
caaggtgaaa tcaaggatgc tactccttca gattttgttc gcgctactgc aacgataccg  25500
atacaagcct cactcccttt cggatggctt attgttggcg ttgcacttct tgctgttttt  25560
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc cccttttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtta  26280
atagttaata gcgtacttct ttttcttgct ttcgtggtat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
gaagagcaac caatggagat tgattaaacg aacatgaaaa ttattctttt cttggcactg  27420
ataacactcg ctacttgtga gctttatcac taccaagagt gtgttagagg tacaacagta  27480
cttttaaaag aaccttgctc ttctggaaca tacgagggca attcaccatt tcatcctcta  27540
```

gctgataaca aatttgcact gacttgcttt agcactcaat ttgcttttgc ttgtcctgac 27600
ggcgtaaaac acgtctatca gttacgtgcc agatcagttt cacctaaact gttcatcaga 27660
caagaggaag ttcaagaact ttactctcca atttttctta ttgttgcggc aatagtgttt 27720
ataacacttt gcttcacact caaaagaaag acagaatgat tgaactttca ttaattgact 27780
tctatttgtg ctttttagcc tttctgctat tccttgtttt aattatgctt attatctttt 27840
ggttctcact tgaactgcaa gatcataatg aaacttgtca cgcctaaacg aacatgaaat 27900
ttcttgtttt cttaggaatc atcacaactg tagctgcatt tcaccaagaa tgtagtttac 27960
agtcatgtac tcaacatcaa ccatatgtag ttgatgaccc gtgtcctatt cacttctatt 28020
ctaaatggta tattagagta ggagctagaa aatcagcacc tttaattgaa ttgtgcgtgg 28080
atgaggctgg ttctaaatca cccattcagt acatcgatat cggtaattat acagtttcct 28140
gtttaccttt tacaattaat tgccaggaac ctaaattggg tagtcttgta gtgcgttgtt 28200
cgttctatga agacttttta gagtatcatg acgttcgtgt tgttttagat ttcatctaaa 28260
cgaacaaact aaaatgtctg ataatggacc ccaaaatcag cgaaatgcac cccgcattac 28320
gtttggtgga ccctcagatt caactggcag taaccagaat ggagaacgca gtggggcgcg 28380
atcaaaacaa cgtcggcccc aaggtttacc caataatact gcgtcttggt tcaccgctct 28440
cactcaacat ggcaaggaag accttaaatt ccctcgagga caaggcgttc caattaacac 28500
caatagcagt ccagatgacc aaattggcta ctaccgaaga gctaccagac gaattcgtgg 28560
tggtgacggt aaaatgaaag atctcagtcc aagatggtat ttctactacc taggaactgg 28620
gccagaagct ggacttccct atggtgctaa caaagacggc atcatatggg ttgcaactga 28680
gggagccttg aatacaccaa aagatcacat tggcacccgc aatcctgcta acaatgctgc 28740
aatcgtgcta caacttcctc aaggaacaac attgccaaaa ggcttctacg cagaagggag 28800
cagaggcggc agtcaagcct cttctcgttc ctcatcacgt agtcgcaaca gttcaagaaa 28860
ttcaactcca ggcagcagta ggggaacttc tcctgctaga atggctggca atggcggtga 28920
tgctgctctt gctttgctgc tgcttgacag attgaaccag cttgagagca aaatgtctgg 28980
taaaggccaa caacaacaag gccaaactgt cactaagaaa tctgctgctg aggcttctaa 29040
gaagcctcgg caaaaacgta ctgccactaa agcatacaat gtaacacaag ctttcggcag 29100
acgtggtcca gaacaaaccc aaggaaattt tggggaccag gaactaatca gacaaggaac 29160
tgattacaaa cattggccgc aaattgcaca atttgccccc agcgcttcag cgttcttcgg 29220
aatgtcgcgc attggcatgg aagtcacacc ttcgggaacg tggttgacct acacaggtgc 29280
catcaaattg gatgacaaag atccaaattt caaagatcaa gtcattttgc tgaataagca 29340
tattgacgca tacaaaacat tcccaccaac agagcctaaa aaggacaaaa agaagaaggc 29400
tgatgaaact caagccttac cgcagagaca gaagaaacag caaactgtga ctcttcttcc 29460
tgctgcagat ttggatgatt tctccaaaca attgcaacaa tccatgagca gtgctgactc 29520
aactcaggcc taaactcatg cagaccacac aaggcagatg ggctatataa acgttttcgc 29580
ttttccgttt acgatatata gtctactctt gtgcagaatg aattctcgta actacatagc 29640
acaagtagat gtagttaact ttaatctcac atagcaatct ttaatcagtg tgtaacatta 29700
gggaggactt gaaagagcca ccacattttc accgaggcca cgcggagtac gatcgagtgt 29760
acagtgaaca atgctaggga gagctgccta tatggaagag ccctaatgtg taaaattaat 29820
tttagtagtg ctatccccat gtgattttaa tagcttctta ggagaatgac aaaaaaaaaa 29880

-continued aaaaaaaaaa aaaaaaaaaa aaa 29903

<210> SEQ ID NO 2
<211> LENGTH: 228
<212> TYPE: DNA
<213> ORGANISM: Severe acute respiratory syndrome coronavirus 2

<400> SEQUENCE: 2
atgtactcat tcgtttcgga agagacaggt acgttaatag ttaatagcgt acttcttttt 60
cttgctttcg tggtattctt gctagttaca ctagccatcc ttactgcgct tcgattgtgt 120
gcgtactgct gcaatattgt taacgtgagt cttgtaaaac cttcttttta cgtttactct 180
cgtgttaaaa atctgaattc ttctagagtt cctgatcttc tggtctaa 228

<210> SEQ ID NO 3
<211> LENGTH: 669
<212> TYPE: DNA
<213> ORGANISM: Severe acute respiratory syndrome coronavirus 2

<400> SEQUENCE: 3
atggcagatt ccaacggtac tattaccgtt gaagagctta aaaagctcct tgaacaatgg 60
aacctagtaa taggtttcct attccttaca tggatttgtc ttctacaatt tgcctatgcc 120
aacaggaata ggtttttgta tataattaag ttaattttcc tctggctgtt atggccagta 180
actttagctt gttttgtgct tgctgctgtt tacagaataa attggatcac cggtggaatt 240
gctatcgcaa tggcttgtct tgtaggcttg atgtggctca gctacttcat tgcttctttc 300
agactgtttg cgcgtacgcg ttccatgtgg tcattcaatc cagaaactaa cattcttctc 360
aacgtgccac tccatggcac tattctgacc agaccgcttc tagaaagtga actcgtaatc 420
ggagctgtga tccttcgtgg acatcttcgt attgctggac accatctagg acgctgtgac 480
atcaaggacc tgcctaaaga aatcactgtt gctacatcac gaacgctttc ttattacaaa 540
ttgggagctt cgcagcgtgt agcaggtgac tcaggttttg ctgcatacag tcgctacagg 600
attggcaact ataaattaaa cacagaccat tccagtagca gtgacaatat tgctttgctt 660
gtacagtaa 669

<210> SEQ ID NO 4
<211> LENGTH: 3822
<212> TYPE: DNA
<213> ORGANISM: Severe acute respiratory syndrome coronavirus 2

<400> SEQUENCE: 4
atgtttgttt ttcttgtttt attgccacta gtctctagtc agtgtgttaa tcttacaacc 60
agaactcaat taccccctgc atacactaat tctttcacac gtggtgttta ttaccctgac 120
aaagttttca gatcctcagt tttacattca actcaggact tgttcttacc tttcttttcc 180
aatgttactt ggttccatgc tatacatgtc tctgggacca atggtactaa gaggtttgat 240
aaccctgtcc taccatttaa tgatggtgtt tattttgctt ccactgagaa gtctaacata 300
ataagaggct ggatttttgg tactacttta gattcgaaga cccagtccct acttattgtt 360
aataacgcta ctaatgttgt tattaaagtc tgtgaatttc aattttgtaa tgatccattt 420
ttgggtgttt attaccacaa aaacaacaaa agttggatgg aaagtgagtt cagagtttat 480
tctagtgcga ataattgcac ttttgaatat gtctctcagc cttttcttat ggaccttgaa 540
ggaaaacagg gtaatttcaa aaatcttagg gaatttgtgt ttaagaatat tgatggttat 600
tttaaaatat attctaagca cacgcctatt aatttagtgc gtgatctccc tcagggtttt 660

```
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacaaagt tgaggctgaa gtgcaaattg ataggttgat cacaggcaga   3000
```

-continued

```
cttcaaagtt tgcagacata tgtgactcaa caattaatta gagctgcaga aatcagagct   3060

tctgctaatc ttgctgctac taaaatgtca gagtgtgtac ttggacaatc aaaaagagtt   3120

gatttttgtg gaaagggcta tcatcttatg tccttccctc agtcagcacc tcatggtgta   3180

gtcttcttgc atgtgactta tgtccctgca caagaaaaga acttcacaac tgctcctgcc   3240

atttgtcatg atggaaaagc acactttcct cgtgaaggtg tctttgtttc aaatggcaca   3300

cactggtttg taacacaaag gaatttttat gaaccacaaa tcattactac agacaacaca   3360

tttgtgtctg gtaactgtga tgttgtaata ggaattgtca acaacacagt ttatgatcct   3420

ttgcaacctg aattagactc attcaaggag gagttagata aatattttaa gaatcataca   3480

tcaccagatg ttgatttagg tgacatctct ggcattaatg cttcagttgt aaacattcaa   3540

aaagaaattg accgcctcaa tgaggttgcc aagaatttaa atgaatctct catcgatctc   3600

caagaacttg gaaagtatga gcagtatata aaatggccat ggtacatttg gctaggtttt   3660

atagctggct tgattgccat agtaatggtg acaattatgc tttgctgtat gaccagttgc   3720

tgtagttgtc tcaagggctg ttgttcttgt ggatcctgct gcaaatttga tgaagacgac   3780

tctgagccag tgctcaaagg agtcaaatta cattacacat aa                        3822
```

<210> SEQ ID NO 5
<211> LENGTH: 27317
<212> TYPE: DNA
<213> ORGANISM: Human coronavirus 229E

<400> SEQUENCE: 5

```
acttaagtac cttatctatc tacagataga aaagttgctt tttagacttt gtgtctactt     60

ttctcaacta aacgaaattt ttgctatggc cggcatcttt gatgctggag tcgtagtgta    120

attgaaattt catttgggtt gcaacagttt ggaagcaagt gctgtgtgtc ctagtctaag    180

ggtttcgtgt tccgtcacga gattccattc tacaaacgcc ttactcgagg ttccgtctcg    240

tgtttgtgtg gaagcaaagt tctgtctttg tggaaaccag taactgttcc taatggcctg    300

caaccgtgtg acacttgccg tagcaagtga ttctgaaatt tctgcaaatg gctgttctac    360

tattgcgcaa gccgtccgcc gttatagcga ggccgctagc aatggtttta gggcatgccg    420

atttgtttca ttagatttgc aggattgcat cgttggcatt gcagacgata catatgttat    480

gggtctgcat ggcaatcaga cgttgttttg caacataatg aaattttctg accgtccttt    540

tatgcttcat gggtggttgg ttttttccaa ttcaaattac cttttggagg aatttgatgt    600

tgtcttcggt aagagaggtg gtggtaatgt gacatacact gaccagtatc tctgtggcgc    660

cgatggcaaa cctgttatga gtgaagattt atggcagttt gttgaccatt tcggtgagaa    720

cgaagaaatt atcatcaatg gtcatactta cgtttgtgct tggcttacta agcgtaagcc    780

cttagattac aaacgtcaga acaaccttgc cattgaagag attgaatatg tgcatggtga    840

tgctttgcat acactacgca atggttctgt tcttgaaatg gctaaggaag tgaagacatc    900

tagtaaagtt gtgttaagcg atgctcttga caaactttac aaagtctttg gttctcctgt    960

tatgacaaat ggttccaaca tcctagaggc ctttactaaa cctgtgttta ttagtgcatt   1020

agttcaatgt acttgtggta ccaagtcttg gtctgttggt gattggaccg gttttaaatc   1080

ctcttgttgc aacgtgatca gtaataaact gtgtgttgtt cccggtaatg ttaaacctgg   1140

tgatgctgtg attaccactc agcaagctgg tgctggtatt aagtattttt gtggcatgac   1200

tcttaagttt gttgcaaata ttgaaggtgt ctctgtttgg agagtgattg ctcttcagag   1260

tgtggattgc tttgttgctt cttccacttt tgtagaagag gaacatgtta atagaatgga   1320
```

-continued

```
tacattctgc ttcaatgtac gcaatagtgt tactgatgag tgtcgtctgg ccatgttggg   1380
tgctgaaatg actagtaatg tcagaagaca agttgcttca ggtgtcatag acattagtac   1440
cggttggttt gatgtttatg atgacatctt tgctgaaagc aaaccatggt ttgttcgcaa   1500
ggctgaagac atttttggcc cttgttggtc cgctcttgct tctgcactta aacaacttaa   1560
agtcactaca ggtgaacttg tgagatttgt taagtctatt tgcaattcag ctgttgctgt   1620
cgtgggtggt actatacaaa ttctcgctag tgtgcctgag aagtttttga atgcgtttga   1680
cgtgtttgtc acagctattc aaactgtctt tgactgtgct gttgaaactt gtactattgc   1740
cggtaaagca tttgacaagg tttttgacta tgttttgctt gataatgcgc ttgtaaaact   1800
tgtcaccaca aagcttaagg gtgttcgtga acgtggcctt aataaagtta agtatgcaac   1860
agttgttgtt ggttccactg aagaagttaa atcttcacgt gttgaacgta gcactgctgt   1920
acttacaatc gccaacaatt attccaaact tttgatgaa gggtatactg ttgtaattgg   1980
cgatgtggcg tactttgtta gtgacggcta cttccgtctt atggccagtc caaatagtgt   2040
gttgactact gcagtctata aaccattgtt tgcttttaat gtgaatgtta tgggtactag   2100
acctgaaaaa tttccaacca ctgtgacttg tgaaaattta gagtctgctg ttttgtttgt   2160
taatgacaaa attactgaat tccaattgga ttacagtatt gatgtcattg ataatgaaat   2220
aattgtcaaa cctaatatca gcctatgtgt tccactttat gtgagagact atgttgacaa   2280
atgggatgat tttgcagac aatatagtaa cgagtcttgg tttgaggatg attacagggc   2340
ttttatcagt gttttggaca tcactgatgc tgctgtgaaa gctgcagagt ctaaagcttt   2400
cgttgatact attgttccac cttgcccatc tattttgaaa gttatagatg gaggcaaaat   2460
atggaatggt gttattaaaa atgttaactc tgttagagac tggcttaagt ctttgaagtt   2520
aaatctcaca caacagggtt tgcttggaac atgtgcaaag cgttttaaac gttggcttgg   2580
cattttgcta gaggcctata atgcgttttt agacactgtg gtttctactg ttaaaattgg   2640
tggcttgacc tttaaaacat atgcttttga taaaccttac attgtgatac gtgatatcgt   2700
gtgtaaggtt gaaaataaaa cagaagcaga atggattgag ctttttccac ataatgacag   2760
gattaagtct tttagtactt tcgagagtgc ttacatgcca attgcagacc ctacacattt   2820
tgacattgaa gaagttgaac ttttagatgc agagtttgta gaaccaggct gtggtggtat   2880
tttggcagta atagatgagc acgtctttta taagaaggat ggtgtttatt atccatcaaa   2940
tggtactaac attctacctg ttgcatttac aaaagccgct ggtggtaaag tttcattttc   3000
tgatgacgtt gaagtaaaag acattgaacc tgtttacaga gtcaagcttt gctttgagtt   3060
tgaagatgaa aaacttgtag atgtttgtga aaaggcaatt ggcaagaaaa ttaaacatga   3120
aggtgactgg gatagctttt gtaagactat tcaatcagca ctttctgttg tttcttgcta   3180
tgtaaatcta cctacttatt acatttatga tgaagaaggc ggtaatgact tgagtttgcc   3240
cgttatgatt tctgaatggc ctctttctgt tcaacaagct caacaagaag ctactttacc   3300
tgatattgct gaggatgttg ttgaccaagt tgaagaagtc aatagcattt ttgacattga   3360
gacagtggat gttaaacatg atgtgagtcc ttttgaaatg ccatttgaag agttaaatgg   3420
tttaaagata ctcaaacaat tggataacaa ctgctgggtt aactcagtta tgttacaaat   3480
acaattaact ggtatacttg atggtgacta tgctatgcag ttttttaaaa tgggccgagt   3540
tgccaagatg attgaacgct gctacactgc tgagcaatgt atacgtggtg ctatgggtga   3600
tgttggtttg tgtatgtata gactgcttaa agacttacac actggtttta tggttatgga   3660
```

-continued

```
ttataaatgt agttgtacca gtggtaggct tgaagaatcg ggagctgttt tgttttgtac   3720
gcccactaag aaggcgtttc cttatggtac ttgtctaaat tgtaacgcac ctcgcatgtg   3780
tacaattagg cagttacaag gtaccataat atttgtgcaa caaaaaccag aacctgttaa   3840
tcctgtttct tttgttgtta aaccagtctg ctcatcaatt tttcgtggtg ctgtgtcttg   3900
tggtcattac cagactaaca tctattcaca aaatttgtgt gtggatggtt ttggtgttaa   3960
caagattcag ccctggacaa atgatgcact taatactatt tgtattaagg atgcagatta   4020
taatgcaaaa gttgaaatat ctgttacacc aattaaaaat acagttgata caacacctaa   4080
ggaagaattt gttgttaaag agaagttgaa cgccttcctc gttcatgaca atgtagcttt   4140
ctaccaaggt gatgttgata ctgttgttaa tggtgttgac tttgacttta ttgtaaatgc   4200
tgctaatgag aaccttgctc atggtggagg acttgccaaa gctttagatg tgtacactaa   4260
aggtaaactt caacgtttat ctaaagaaca cattggatta gcgggtaaag taaaagttgg   4320
tacaggagtt atggttgagt gtgatagcct tagaattttt aatgttgttg gtccacgcaa   4380
gggtaaacat gaacgtgatt tactcataaa agcttacaac actattaata atgaacaagg   4440
cacaccttta acaccaattt tgagctgtgg tatttttggt atcaaactcg aaacttcatt   4500
agaagttttg cttgatgttt gtaatacaaa agaagttaaa gtttttgttt atacagacac   4560
agaggtttgt aaggttaagg attttgtgtc tggtttagtg aatgttcaaa aagttgagca   4620
acctaaaata gaaccaaaac cagtgtccgt aattaaagtt gcacccaagc cttacagggt   4680
agatggtaaa tttagttact ttacagaaga cttgttgtgt gtcgctgatg acaaacccat   4740
tgttttgttt actgactcta tgcttacttt ggatgaccgt ggtttagctc tagacaatgc   4800
acttagtggt gtgcttagtg ctgctattaa ggattgtgtt gacataaata aagctatacc   4860
ttctggtaat cttattaagt ttgatatagg ttctgttgtt gtctacatgt gtgttgtgcc   4920
atccgaaaag gacaaacatt tagataataa tgttcaacga tgcacacgta agttgaatag   4980
acttatgtgt gatatagttt gtactatacc agctgactac atcttgccat tggtgttgtc   5040
tagtttgact tgtaatgttt cttttgtagg tgaacttaaa gctgctgaag ctaaagttat   5100
aactataaag gtgacagagg atggtgttaa tgttcatgat gtgaccgtga caacagacaa   5160
gtcatttgaa caacaagttg gtgttattgc tgataaggac aaagatcttt ctggtgcagt   5220
accaagtgat cttaacacat ctgaattgct tactaaagca atagatgttg attgggtcga   5280
attttatggc tttaaagatg ctgttacttt tgcaacagtt gatcatagtg cttttgccta   5340
tgaaagtgct gttgttaatg gtattagagt gttaaaaact agtgataata attgttgggt   5400
gaatgctgtt tgtattgcac tacagtattc gaaaccccat tttatttcac aaggtcttga   5460
tgctgcgtgg aataaatttg ttttaggcga tgttgaaatt tttgttgcat ttgtttacta   5520
tgttgcaaga ctaatgaaag gtgacaaggg tgatgctgaa gacactttga ctaagttgtc   5580
taagtatctt gctaatgaag ctcaagttca attagaacat tatagttctt gtgttgaatg   5640
tgatgctaaa tttaaaaact ctgttgcatc tatcaattct gctatagttt gtgctagtgt   5700
caaacgtgat ggtgtgcaag ttggttattg tgtccatggt attaagtact attcacgtgt   5760
tagaagtgtt agaggtagag ctattatagt cagtgtcgaa cagcttgaac cgtgtgctca   5820
gtctagactt ttgagtggtg ttgcttatac tgctttttct ggacctgttg acaaaggtca   5880
ttatactgtt tatgatactg caaagaaatc aatgtatgat ggtgatcgtt ttgttaaaca   5940
tgatctttct ctgctgtctg tcacatcagt tgttatggtt ggtggttatg ttgcacctgt   6000
taatacagtg aaacctaaac cagtcattaa tcaacttgat gaaaaggcac agaagttctt   6060
```

-continued tgattttggt gattttttga ttcataattt tgttattttt ttcacatggt tattgagtat 6120
gtttactttg tgtaaaactg cagtaactac aggtgatgtt aaaataatgg ccaaagcacc 6180
acaaaggacg ggtgttgttt taaaacgtag tcttaaatat aacttaaaag cgtcagcagc 6240
tgttcttaaa tctaagtggt ggctgcttgc taagtttacg aaactactgt tactcatata 6300
tacattgtac tcagtagttt tgctttgtgt acgttttgga ccgtttaatt tttgtagtga 6360
gactgttaat ggttatgcta agtcaaactt tgtcaaggat gattactgtg atggttcatt 6420
gggctgcaag atgtgtcttt ttggttacca agagttaagt caatttagcc atttggatgt 6480
tgtgtggaag catataacag accctttgtt tagtaatatg caacctttca ttgtcatggt 6540
tttgctgctt atatttggtg acaattattt gagatgcttc ttgctgtatt ttgttgctca 6600
gatgataagc acagttggtg tttttctagg ttacaaggaa acaaattggt tcttgcactt 6660
tattccattt gatgttattt gtgatgaact gcttgtcact gttattgtta ttaaggttat 6720
ttcttttgtc agacatgtgc tttttggttg tgaaaaccca gattgtattg cgtgttctaa 6780
gagtgctaga cttaagagat tccctgttaa cacaattgtc aatggtgtgc aacgttcatt 6840
ttatgttaat gcaaatggtg gtagtaagtt ttgtaagaaa catagatttt tctgtgttga 6900
ttgtgactct tatggttatg gcagcacgtt tataacaccc gaagtttcta gagaacttgg 6960
taacattacc aaaacaaatg tgcaaccaac agggccggcc tatgtcatga ttgacaaagt 7020
ggagtttgaa aatggttttt acagattgta ttcctgtgaa acattttggc gttacaactt 7080
tgatataact gaaagcaagt attcttgcaa agaggttttt aaaaattgta atgttttgga 7140
tgatttcatc gtgtttaaca ataatgggac caatgtaacg caggttaaaa atgctagtgt 7200
ttacttttca cagttgttgt gtaggcccat taaattagtt gacagtgaac ttttgtccac 7260
tttgtcagtt gattttaatg gtgtcttaca caaggcatac attgatgtac tacgtaatag 7320
ctttggtaaa gatcttaatg ctaatatgtc tttagccgag tgcaagagag ctttaggcct 7380
gtctattagt gatcatgaat ttactagtgc tatttctaat gcacatcgtt gtgacgtgtt 7440
gttatctgat ttgtcattta acaactttgt cagttcgtat gctaaacctg aggaaaaatt 7500
atcagcttat gacttggcgt gttgtatgcg tgcaggtgct aaggttgtta atgccaatgt 7560
tctgacaaag gaccaaactc ctattgtttg gcatgcaaag gattttaaca gtctttctgc 7620
tgaaggtcgc aagtatattg taaaaactag caaagctaag ggtttgactt tcttgttgac 7680
aattaatgaa aaccaagctg tcacgcaaat acctgcaact agcattgttg ctaagcaagg 7740
tgctggtgat gctggccatt cattaacatg gctgtggcta ctgtgtggtc ttgtgtgttt 7800
gattcaattc tacttgtgct ttttcatgcc ctattttatg tacgatatcg tgagtagttt 7860
tgagggttat gattttaagt atatagaaaa tggtcagttg aagaattttg aagcgccact 7920
taaatgcgtc agaaacgttt ttgaaaactt tgaggactgg cattatgcta agtttggctt 7980
cacaccttta aacaagcaaa gctgtcctat tgtagttgga gtttctgaaa ttgttaatac 8040
tgtcgctggc attccatcta atgtgtatct tgttggtaaa actttaattt ttacactaca 8100
agctgctttt ggtaatgctg gtgtttgtta tgacattttt ggagtcacaa cacctgaaaa 8160
gtgcattttt acttctgctt gtactagatt agaaggtttg ggtggtaaca atgtttattg 8220
ttataacaca gcgcttatgg aaggttcttt gccttacagt tcaatacaag ctaatgcata 8280
ttataaatat gacaatggca attttattaa gttgccagaa gttattgcac aaggctttgg 8340
ttttagaaca gtgcgtacta ttgccaccaa atactgccgc gtaggtgaat gtgttgaatc 8400

```
caatgcaggt gtgtgttttg gctttgacaa gtggtttgtt aacgatggac gtgttgccaa   8460
tggttacgtt tgtggtactg gtttgtggaa ccttgtattt aacatacttt ccatgttttc   8520
atcttcattc tctgttgctg caatgtcagg tcaaatttta cttaattgtg cattaggtgc   8580
ttttgctatt ttttgttgtt ttcttgtgac aaagtttaga cgcatgtttg gtgacctttc   8640
tgtaggtgtt tgcactgttg ttgtggctgt tttgcttaac aatgtctctt acattgtaac   8700
tcagaattta gtaacaatga ttgcttatgc catattgtat ttctttgcta ctagaagctt   8760
acgctatgca tggatttggt gtgctgcata tttaattgcg tatatttctt ttgctccatg   8820
gtggttgtgt gcttggtact ttcttgctat gttgacaggt ttgttaccta gtttgctgaa   8880
gcttaaagtt tcgacaaatc ttttcgaagg tgacaaattt gtaggtacat ttgaaagtgc   8940
tgctgcagga acatttgtca ttgacatgcg ttcttatgag aaacttgcta atagcatctc   9000
tccagaaaag ttgaaaagtt atgctgctag ctataataga tataagtact atagtggtaa   9060
tgcaaatgaa gctgattacc gttgcgcttg ttatgcctat ttagcaaaag caatgttgga   9120
cttttcgcgt gatcataatg acatcttgta cacacctccg actgtcagtt atggttctac   9180
attacaggct ggtttgcgca aaatggcaca accatctggc tttgtggaga aatgtgttgt   9240
ccgtgtctgc tatggaaaca ctgtgttgaa tgggttgtgg cttggtgata ttgtttattg   9300
cccacgtcat gttatcgcat ctaacacaac ttctgctata gattatgatc acgaatatag   9360
tattatgcgg ttgcataatt tttctataat atctggtaca gcatttcttg gtgttgtagg   9420
tgctactatg catggagtaa ctcttaaaat taaggtttca cagactaaca tgcacacacc   9480
tagacattct tttagaacac taaaatctgg tgaaggtttt aacatcttag catgctatga   9540
tggttgtgct caaggtgttt ttggtgtgaa catgagaact aattggacta tccgtggttc   9600
atttattaat ggtgcgtgtg gttcccctgg ctacaatctt aaaaatggcg aggtggaatt   9660
tgtttatatg catcaaattg aactcggaag tggtagccat gtaggttcta gctttgatgg   9720
tgttatgtat ggtggttttg aagaccaacc taatcttcaa gttgaatctg caaaccagat   9780
gttaacagtt aatgtggttg catttcttta tgctgctata ttgaatggtt gcacatggtg   9840
gcttaaaggt gaaaaattgt ttgtggagca ttataatgag tgggcacagg ctaatggttt   9900
cacagctatg aatggtgaag acgctttttc cattcttgct gctaaaactg gtgtctgtgt   9960
ggaaagatta cttcatgcta ttcaagtttt gaataatggc tttggtggta aacaaatttt  10020
gggttattct agtctcaatg atgagttcag tattaatgaa gttgtcaaac aaatgtttgg  10080
tgttaacctg caaagtggta aaaccactag tatgtttaaa tccataagct tatttgctgg  10140
cttctttgtc atgttctggg ctgaattatt tgtttatacc accactattt gggttaaccc  10200
tggttttctt actccgttta tgattttgct tgttgctttg tcactctgtc ttacatttgt  10260
tgttaaacat aaggttttgt tttgcaagt gtttttgttg ccttcaatta ttgtggctgc  10320
tattcaaaac tgtgcttggg actaccatgt tacaaaggtg ttggcagaga agtttgatta  10380
taatgtttct gttatgcaaa tggacatcca gggttttgtt aacattttta tttgtctttt  10440
tgttgcactg ttgcatactt ggcgctttgc taaagagcgt tgtacacatt ggtgcactta  10500
tttgttctca ctcattgctg ttttatacac tgcattgtat agttatgact acgttagttt  10560
gctggttatg ctactttgtg caatttctaa tgaatggtat attggtgcta ttatttttag  10620
aatttgtcgt tttggtgttg catttttacc agtggaatac gtgtcttact ttgatggtgt  10680
taaaactgtg ctgttgtttt acatgttgtt aggctttgtt agctgtatgt actatggttt  10740
gttgtactgg attaacaggt tctgtaagtg cacattaggt gtttatgatt tctgtgttag  10800
```

tccagccgaa tttaagtata tggttgctaa tggtttgaat gcaccaaatg gcccttttga 10860
tgcgctcttt ctgtctttta aactaatggg tattggcggt cctagaacca ttaaagtttc 10920
tactgtacag tctaaattga ctgatcttaa gtgcacaaac gtcgttctaa tgggcatttt 10980
gtctaacatg aacatagctt ctaattcaaa ggagtgggca tattgtgttg aaatgcacaa 11040
taaaataaac ttgtgtgacg accctgaaac tgctcaagag ttattgctgg cgttgttggc 11100
ctttttcttg tctaagcata gtgattttgg tcttggtgat cttgtcgatt cttattttga 11160
gaacgactcc attttgcaaa gtgttgcatc ttcttttgtt ggtatgccat cttttgttgc 11220
atatgaaaca gcaagacaag agtatgaaaa tgctgttgca aatggttcct caccacaaat 11280
aatcaaacaa ttgaagaagg ctatgaatgt tgcaaaagct gagtttgaca gggaatcatc 11340
tgttcaaaag aaaattaaca gaatggctga acaagctgct gcagctatgt acaaagaagc 11400
acgtgctgtt aatagaaaat caaaagttgt tagtgccatg catagtttac tctttggcat 11460
gctccgacgt ttggacatgt ctagtgttga cactatcctt aatatggcac gtaatggtgt 11520
tgtccctctt tccgttatcc ctgctacttc tgcagccagg ctcgtcgtcg tagtaccaga 11580
tcatgattca tttgtgaaaa tgatggtaga tggttttgtg cactacgctg gtgttgtttg 11640
gacattacag gaagttaagg ataatgatgg taagaatgtg catcttaaag atgttacaaa 11700
ggaaaaccag gaaatacttg tttggcctct gattttgact tgtgaacgtg tcgttaaatt 11760
gcagaacaat gaaataatgc cgggcaagat gaaggtcaag gccaccaaag gtgaaggtga 11820
tggaggcatt actagtgaag gtaatgctct atacaacaat gaaggtggac gtgcattcat 11880
gtatgcatat gtgactacga agcctggcat gaagtatgtt aaatgggaac atgactctgg 11940
tgtggttaca gttgaattgg aaccaccttg cagatttgtt atagacacac ctactggacc 12000
ccaaattaag tatctttatt ttgttaagaa tcttaacaat ttaaggagag gtgctgtttt 12060
gggttacatt ggtgccactg tgagattgca agctggcaaa cagactgagt ttgtttcaaa 12120
ctcccattta ttaacacatt gttcttttgc tgttgaccca gctgcagcct atcttgatgc 12180
tgttaaacaa ggcgcaaaac ctgttggcaa ttgtgtaaag atgttgacta atggttctgg 12240
tagcggtcag gctattactt gtaccattga ttccaacact acgcaggaca catatggtgg 12300
cgcgtctgtt tgtatttatt gcagagcaca tgttgcacat ccaaccatgg acggtttttg 12360
tcagtacaaa ggcaagtggg tacaagtgcc tataggtaca aatgacccta taagattttg 12420
tcttgaaaat actgtttgta aagtttgtgg ttgttggctt aatcatggct gtacatgtga 12480
ccggactgct atccaaagtt ttgataacag ttatttaaac gagtccgggg ctctagtgcc 12540
gctcgactag agccctgtaa tggtacagac atagattact gtgtccgtgc atttgacgtt 12600
tacaataaag atgcgtcttt tatcggaaaa aatctgaagt ccaattgtgt gcgcttcaag 12660
aatgtagata aggatgacgc gttctatatt gttaaacgtt gcattaagtc agttatggac 12720
cacgagcagt ccatgtataa cttacttaaa ggctgtaatg ctgttgctaa gcatgatttc 12780
tttacttggc atgagggcag aaccatttat ggtaatgtta gtagacagga tcttactaaa 12840
tacaccatga tggatttgtg cttcgctctg cgtaactttg atgaaaaaga ctgtgaagtt 12900
tttaaggaga tattggttct tactggttgt tgtagtactg attactttga aatgaagaat 12960
tggtttgacc ccatagaaaa tgaggacata caccgtgtgt atgctgcttt aggtaaggta 13020
gttgcaaatg caatgcttaa gtgtgttgct ttttgcgacg aaatggtgct caaaggagtt 13080
gttggtgttt tgaccttaga caaccaagat cttaatggga atttctatga cttcggtgac 13140

```
tttgtattgt gtcctcctgg aatgggaata ccctactgca cgtcatacta ttcttatatg  13200
atgcctgtta tgggtatgac taattgttta gctagtgagt gctttatgaa aagtgacatc  13260
tttggtcaag acttcaaaac ttttgatttg ttgaaatatg atttcacaga acataaggag  13320
gttttgttta acaagtactt taagtattgg ggacaggatt atcatcctga ttgtgttgat  13380
tgccatgacg agatgtgtat tttgcattgt tcaaatttta acacactctt cgcaaccaca  13440
attccaaaca cggcttttgg acctctatgc agaaaagtgt ttattgatgg tgtacccgta  13500
gttgctactg ctggttacca ctttaaacaa ttaggacttg tgtggaacaa agatgttaac  13560
actcattcta ccagacttac tattactgaa ctcttacagt ttgtgacaga tccaacgctt  13620
atagttgcgt catcgcctgc cttggtggat aaacgcactg tttgtttttc tgtcgctgct  13680
ttgagtacag gattaacatc ccaaacagta aaacctggcc attttaataa ggagttttat  13740
gacttcttac gttctcaggg gtttttcgat gagggttcag aattaacatt gaagcatttc  13800
tttttacac aaaagggtga tgctgcaatt aaagattttg attattatcg ttacaacaga  13860
cctactatgc tggatattgg acaagctcgc gtagcatatc aagtggcagc tcgctatttt  13920
gactgttacg agggtggctg tattacatct agagaggttg ttgttacaaa ccttaataaa  13980
agcgctggtt ggccccttaa taagtttggt aaagctggtt tatattatga gtctattagt  14040
tatgaggaac aagatgctat tttttcatta acaaagcgta atattctccc tactatgact  14100
cagttaaatc ttaaatacgc catatctggt aaggaacgcg cacgtacagt gggtggcgtc  14160
tctttattag ctactatgac tacaagacag tttcatcaga aatgtctgaa atccatagta  14220
gctaccagaa atgccaccgt tgttatcggc actaccaagt tttatggcgg gtgggataat  14280
atgttaaaga acctgatggc cgatgttgat gatcctaaat tgatgggatg ggactatcct  14340
aagtgtgata gagctatgcc ctcaatgatt cgtatgttgt cggctatgat cttaggttct  14400
aagcatgtca catgttgtac ggctagtgat aaattttata gacttagtaa tgagcttgct  14460
caagttttga ccgaggttgt ttattcaaat ggtgggtttt attttaaacc tggtggtaca  14520
acttctggtg atgcaactac agcctacgcc aattctgtct ttaatatatt tcaggctgta  14580
agttctaaca ttaattgcgt tttgagcgtt aactcgtcaa attgcaataa ttttaatgtt  14640
aagaagttac agagacaact ttatgataat tgctatagaa atagtaatgt tgatgaatct  14700
tttgtggatg acttttatgg ttatttgcaa aagcattttt ctatgatgat tctttctgat  14760
gatagtgttg tgtgctataa taaaacttat gctggacttg gttacattgc tgatattagt  14820
gcttttaaag ccactttgta ttatcagaat ggtgtgttta tgagtacagc taagtgttgg  14880
actgaggaag atctttctat aggacctcat gaattttgct cacagcacac tatgcagatt  14940
gtagatgaaa atggtaagta ttatctacca tatccagatc ctagccgtat tatttctgct  15000
ggtgtttttg tggatgacat cactaagact gatgctgtca ttcttttgga acgctatgtt  15060
tctctggcta tagatgccta cccattgtct aagcatccta aacctgagta caggaaggtg  15120
ttttacgcat tgttagactg ggtcaaacat ctcaacaaga ctcttaacga aggtgttttg  15180
gagtcttttt ctgttacact tttagatgaa catgagtcta agttttggga tgaaagcttt  15240
tatgctagta tgtatgagaa gtctacagta ttacaagctg ctggtctttg tgtagtatgt  15300
ggttctcaaa cagttctaag atgcggtgat tgtttacgca gaccgatgtt gtgcactaag  15360
tgcgcctatg atcatgtgtt tggcactgat cataagttca ttttagctat tacaccatat  15420
gtgtgtaaca catctggctg caatgtaaat gacgttacaa aactgtatct tggaggtttg  15480
aattattact gtgtagacca caaaccacat ctttcattcc cactgtgttc agctggtaat  15540
```

```
gtctttggtt tgtacaaaag ttctgctttg ggttccatgg acattgatgt ctttaacaaa  15600
ctttctacct ctgattggtc tgacattcgc gactacaagc ttgctaatga tgcaaaagag  15660
tcactaaggt tgtttgcagc tgaaacggtc aaggctaaag aggaaagtgt taagtcatca  15720
tacgcttatg ctaccctaaa ggagattgta ggtcctaagg aacttttgct cttatgggaa  15780
agtggaaaag ccaaaccacc gttaaaccgt aattctgttt ttacatgctt ccaaattaca  15840
aaagactcca agtttcaagt tggtgagttt gtgtttgaga aagtagatta cggttctgat  15900
acggttactt acaaatccac tgctactact aagttagtac caggtatgtt gtttattttg  15960
acttctcata atgttgctcc acttagagcg ccaacaatgg caaaccagga gaaatattct  16020
accatttaca agttgcaccc atcatttaat gttagtgatg cttatgcaaa tcttgtacct  16080
tattaccaac ttattggcaa acagcgtata accacaatac agggtcctcc tggtagtgga  16140
aaatcgcatt gttctattgg tattggtgtg tattaccctg gagcgaggat cgtgttcacc  16200
gcttgttctc acgctgctgt tgattcgctc tgtgcaaaag ctgtcacagc ctatagtgtt  16260
gataagtgta cacgtattat tcctgcacgt gccagagttg agtgttatag tggttttaaa  16320
cctaacaata atagtgcaca atacgtgttt agtactgtta atgcgttacc tgaagttaat  16380
gcagacattg ttgtcgtgga tgaggtgtct atgtgcacta actatgactt gtctgtgatt  16440
aaccagcgta tatcatataa acacattgta tatgttggtg atcctcaaca gcttccagct  16500
cctagagttc ttatctctaa aggtgttatg gaaccaattg actataatgt tgtgacacaa  16560
cgtatgtgtg ctataggacc cgatgtcttt ttacacaagt gttacagatg tcctgctgaa  16620
atagttaaca ctgtttcaga gcttgtttat gaaaacaagt ttgtacctgt caaagaagct  16680
agtaagcagt gcttcaaaat ctttgaacgc ggtagtgttc aggtagacaa tggctccagt  16740
ataaataggc gtcaacttga tgttgttaag cgatttatac ataaaaactc cacatggagc  16800
aaggctgtgt ttatctcacc ttacaatagt caaaattatg tagctgccag gcttttaggc  16860
ttacaaactc agacagtgga ttctgctcaa ggtagtgaat atgactatgt tatattcgca  16920
cagacatcag atactgctca tgcctgtaat gccaatcgtt ttaacgttgc cattactaga  16980
gcaaagaaag gtattttctg tattatgtct gacagaactt tgtttgatgc acttaagttc  17040
tttgaaatca ctatgacaga tttacagtct gaaagtagtt gtggtttgtt taaggattgt  17100
gcacgtaacc ctattgattt accaccaagt catgccacta cttatttgtc attgtctgat  17160
agatttaaga ctagtggtga cttggctgtt caaataggta acaacaatgt ttgtacctat  17220
gaacatgtga tttcatatat gggtttcagg tttgatgtta gcatgcctgg tagtcatagt  17280
ttgttctgta ctagagactt tgccatgcgt catgtcagag gttggttagg aatggatgtg  17340
gaaggtgcac atgtcacagg tgacaatgtt ggcactaatg tacctctaca agttggtttt  17400
tccaatggtg ttgattttgt agctcaacct gaaggttgtg ttctaacaaa cactggcagt  17460
gttgtaaaac ctgttcgtgc tcgtgcacca cctggagaac aattcactca cattgtacct  17520
ctgttacgca agggacaacc ttggagtgtg ttgagaaaac gtattgttca aatgatagca  17580
gattttcttg ctggctcatc tgatgtactg gtgtttgtac tttgggctgg cggtttagag  17640
ttgaccacta tgcgttattt tgttaagatt ggagctgtta aacattgcca atgtggtact  17700
gttgcaacat gctacaattc tgttagtaat gactattgtt gctttaaaca tgcattgggc  17760
tgtgactatg tttataatcc atatgtcata gatattcaac aatggggtta tgttggttca  17820
ctctccacta atcaccatgc aatttgtaat gttcatagaa atgagcatgt tgcttctggt  17880
```

-continued gatgctatta tgactagatg tttggctgtg tatgactgct ttgttaagaa tgtggattgg 17940
tcaattacct accctatgat agctaatgaa aatgccataa acaagggcgg tcgcactgtg 18000
cagagtcata ttatgcgtgc tgctattaaa ttgtacaacc ctaaagcaat ccatgacatt 18060
ggtaatccta agggtattcg ttgtgctgta actgatgcca agtggtattg ttatgacaag 18120
aaccctatta attctaatgt gaaaacattg gagtatgatt acatgacaca tggccaaatg 18180
gatggcttgt gtttgttttg gaattgtaat gtggatatgt accctgaatt ctcaattgtt 18240
tgcaggtttg acacacgtac acgatctaca ttgaaccttg aaggtgtaaa tggtgggtca 18300
ttgtatgtca ataatcatgc atttcacact cctgcttatg ataaacgtgc tatggctaaa 18360
ttgaaaccag caccgttttt ctactatgac gacggttcat gtgaggttgt tcacgatcaa 18420
gttaactatg ttcctttgag agccactaat tgcattacca agtgtaatat tggtggtgct 18480
gtatgttcta agcacgctaa tctctataga gcatatgttg agtcatataa catttttact 18540
caagctggtt ttaatatttg ggttcctacc acgtttgatt gttataattt gtggcagaca 18600
ttcacagagg tcaatttaca aggtttagag aacattgctt ttaacgttgt taataaaggt 18660
tcatttgttg gtgctgatgg tgaattacca gtagccatta gtggtgataa agtgttcgta 18720
cgtgatggta acactgataa tttagtcttt gttaacaaaa catcactgcc tacaaacata 18780
gcatttgaac tttttgctaa gaggaaggtt ggtttaacac cacctctcag tattctcaaa 18840
aaccttggtg ttgtcgccac atataagttt gtcttgtggg attatgaagc tgagcgtccc 18900
ttgacaagct ttactaagtc tgtttgtggt tatacagact ttgcagagga tgtttgtact 18960
tgttacgata atagtataca aggttcatac gaacgtttta ctctgtcaac taatgctgtg 19020
ttattctctg ctactgctgt gaaaacaggt ggtaagagtt tgccggctat taaattgaat 19080
tttggaatgc ttaatggtaa tgcaattgct actgtcaaat cagaagatgg taacataaaa 19140
aatattaact ggtttgttta cgtacgcaaa gatggcaaac ctgttgatca ttatgatggt 19200
ttttataccc aaggtcgtaa tttacaagac tttttgcctc gcagcacaat ggaagaagac 19260
tttttgaaca tggatatagg cgtgtttatt caaaagtatg gtctagagga tttcaacttc 19320
gagcacgttg tgtatggtga tgtttcaaaa actactctag gcggtttaca cttgttgatt 19380
tcacaagtac gtctgagtaa aatgggcatc ttaaaggcag aggagtttgt ggcagcatct 19440
gacataacac tcaaatgttg tactgtgact tatcttaatg atcctagttc taagactgtt 19500
tgtacttaca tggatttgtt gttggatgat tttgtttctg tattgaagtc tttggatttg 19560
actgttgtat ccaaggttca tgaggtcata attgacaaca aaccatggag atggatgcta 19620
tggtgtaaag ataatgccgt tgctacattc tatcctcagt tgcagagtgc agaatggaaa 19680
tgcgggtatt ctatgcctgg tatttataag acacaacgta tgtgcttaga accatgtaat 19740
ttgtataatt atggtgcagg tttgaagttg cccagtggca ttatgttcaa tgttgttaaa 19800
tacactcaat tgtgtcaata ttttaacagt accacgttat gtgttcctca taatatgaga 19860
gtgttacact tgggtgctgg ctctgattat ggtgttgcac caggaactgc tgttcttaaa 19920
aggtggttgc cgcacgacgc aattgttgtt gacaacgatg ttgttgacta tgtgagtgac 19980
gctgatttta gtgttactgg tgattgtgca accgtttatt tggaagacaa gtttgacttg 20040
ttaatctctg atatgtacga tggtaggaca aaggcaattg atggtgaaaa tgtttcgaaa 20100
gaaggatttt tcacttacat caatggtttc atttgtgaaa aacttgccat cggaggttcg 20160
attgctatta aagtaacaga gtatagctgg aataagaaat tgtatgaact tgtacaaaga 20220
ttttcttttt ggactatgtt ttgcacttct gttaatacgt catcatcaga agcctttgtt 20280

-continued

```
gtcggaatta actatcttgg tgatttcgca caaggacctt ttatagatgg taacataata  20340
cacgcaaatt atgtattttg gcgtaactcc actgttatga gtttgtccta caactctgtt  20400
ttagacctga gtaaatttaa ttgcaaacac aaagcgactg ttgttgtgca attaaaggat  20460
agtgatatta atgaaatggt gcttagtctt gttaggagtg gtaagttgct tgtaaggggt  20520
aatggcaagt gtttgagttt tagtaatcat ttagtctcaa ctaaataaaa tgtttgtttt  20580
gcttgttgca tatgccttgt tgcatattgc tggttgtcaa actacaaatg ggctgaacac  20640
tagttactct gtttgcaacg gctgtgttgg ttattcagaa aatgtatttg ctgttgagag  20700
tggtggttat ataccctccg actttgcatt caataattgg ttccttctaa ctaatacctc  20760
atctgttgta gatggtgttg tgaggagttt tcagcctttg ttgcttaatt gcttatggtc  20820
tgtttctggc ttgcggttta ctactggttt tgtctatttt aatggtactg ggagaggtga  20880
ttgtaaaggt ttttcctcag atgttttgtc tgatgtcata cgttacaacc tcaattttga  20940
agaaaacctt agacgtggaa ccattttgtt taaaacatct tatggtgttg ttgtgtttta  21000
ttgtaccaac aacactttag tttcaggtga tgctcacata ccatttggta cagttttggg  21060
caatttttat tgctttgtaa atactactat tggcaatgaa actacgtctg cttttgtggg  21120
tgcactacct aagacagttc gtgagtttgt tatttcacgc acaggacatt tttatattaa  21180
tggctatcgc tatttcactt taggtaatgt agaagccgtt aatttcaatg tcactactgc  21240
agaaaccact gatttttgta ctgttgcgtt agcttcttat gctgacgttt tggttaatgt  21300
gtcacaaacc tctattgcta atataattta ttgcaactct gttattaaca gactgagatg  21360
tgaccagttg tcctttgatg taccagatgg tttttattct acaagcccta ttcaatccgt  21420
tgagctacct gtgtctattg tgtcgctacc tgtttatcat aaacatacgt ttattgtgtt  21480
gtacgttgac ttcaaacctc agagtggcgg tggcaagtgc tttaactgtt atcctgctgg  21540
tgttaatatt acactggcca attttaatga aactaaaggg cctttgtgtg ttgacacatc  21600
acacttcact accaaatacg ttgctgttta tgccaatgtt ggtaggtgga gtgctagtat  21660
taacacggga aattgccctt tttcttttgg caaagttaat aactttgtta aatttggcag  21720
tgtatgtttt tcgctaaagg atatacccgg tggttgcgca atgcctatag tggctaattg  21780
ggcttatagt aagtactata ctataggctc attgtatgtt tcttggagtg atggtgatgg  21840
aattactggc gtcccacaac ctgttgaggg tgttagttcc tttatgaatg ttacattgga  21900
caaatgtact aaatataata tttatgatgt atctggtgtg ggtgttattc gcgttagcaa  21960
tgacaccttt cttaatggaa ttacgtacac atcaacttca ggtaaccttc tgggttttaa  22020
agatgttact aagggcacca tctactctat cactccttgt aacccaccag atcagcttgt  22080
tgtttatcag caagctgttg ttggtgctat gttgtctgaa aattttacta gttacggctt  22140
ttctaatgtt gtagaactgc cgaaattttt ctatgcgtcc aatggcactt ataattgcac  22200
agacgctgtt ttaacttatt ctagttttgg cgtttgtgca gatggttcta taattgctgt  22260
tcaaccacgt aatgtttcat atgatagtgt ttcagctatc gtcacagcta atttgtctat  22320
accttccaat tggaccactt cggtccaggt tgagtattta caaattacaa gtacacctat  22380
cgtagttgat tgctccactt atgtttgcaa tggtaatgtg cgctgtgttg aattgcttaa  22440
gcagtatact tctgcttgta aaactattga agacgcctta agaaatagcg ccaggctgga  22500
gtctgcagat gttagtgaga tgctcacttt tgacaagaaa gcgtttacac ttgctaatgt  22560
tagtagtttt ggtgactaca accttagcag cgtcatacct agcttgccca caagtggtag  22620
```

```
tagagtggct ggtcgcagtg ccatagaaga catacttttt agcaaacttg ttacttctgg  22680
acttggcact gtggacgcag actacaaaaa gtgcactaag ggtctttcca ttgctgactt  22740
ggcttgtgct caatattata atggcattat ggttttgcct ggcgtcgctg atgctgaacg  22800
aatggccatg tatacaggtt ctttaattgg tggaattgct ttaggaggtc taacatcagc  22860
cgtttcaata ccattttcat tagcaattca ggcacgttta aattatgttg cattgcagac  22920
tgatgtttta caagaaaatc agaaaattct tgctgcatct tttaacaaag caatgaccaa  22980
catagtagat gcctttactg gtgttaatga tgctattaca caaacttcac aagccctaca  23040
aacagttgct actgcactta acaagatcca ggatgttgtt aatcaacaag gcaactcatt  23100
gaaccattta acttctcagt tgaggcagaa ttttcaagct atctctagct ctattcaggc  23160
tatctatgac agacttgaca ctattcaggc tgatcaacaa gtagataggc tgattactgg  23220
tagattggct gctttgaatg tattcgtttc tcatacattg actaagtaca ctgaagttcg  23280
tgcttccaga cagcttgcac aacaaaaagt gaatgagtgt gtcaaatccc agtctaagcg  23340
ttatggcttc tgtggaaatg gcactcacat tttctcaatt gttaatgctg ctcctgaggg  23400
gcttgttttt ctccacactg tcttgttgcc gacacaatat aaggatgttg aagcgtggtc  23460
tgggttgtgc gttgatggta caaacggtta tgtgttgcga caacctaatc ttgctcttta  23520
caaagaaggc aattattata gaatcacatc tcgcataatg tttgaaccac gtattcctac  23580
catggcagat tttgttcaaa ttgaaaattg caatgtcaca tttgttaaca tttctcgctc  23640
tgagttgcaa accattgtgc cagagtatat tgatgttaat aagacgctgc aagaattaag  23700
ttacaaattg ccaaattaca ctgttccaga cctagttgtc gaacagtaca accagactat  23760
tttgaatttg accagtgaaa ttagcaccct tgaaaataaa tctgcggagc ttaattacac  23820
tgttcaaaaa ttgcaaactc tgattgacaa cataaatagc acattagtcg acttaaagtg  23880
gctcaaccgg gttgagactt acatcaagtg gccgtggtgg gtgtggttgt gcatttcagt  23940
cgtgctcatc tttgtggtga gtatgttgct attatgttgt tgttctactg gttgctgtgg  24000
cttctttagt tgttttgcat cttctattag aggttgttgt gaatcaacta aacttcctta  24060
ttacgacgtt gaaaagatcc acatacagta atggctctag gtttgttcac attgcaactt  24120
gtgtctgctg ttaatcaatc gcttagcaat gcgaaagtta gtgctgaagt ttcacgacag  24180
gttatccaag acgtgaaaga tggcactgtt accttcaact tgctagcgta tacactaatg  24240
agcctctttg ttgtgtattt tgctttattt aaagcaagat cacaccgtgg cagagctgct  24300
cttatagtgt ttaaaattct aatccttttc gtttatgtgc cattgctgta ttggtctcaa  24360
gcatatattt acgcaacttt gattgctgta attttgcttg gaagattttt ccatacagct  24420
tggcactgct ggctctacaa gacatgggat ttcattgtct tcaatgtaac cacactttgc  24480
tatgcaaggt aagtgttggt ttcttgaaaa taaggctctg aaaccattcg tttgttttta  24540
cggaggggat caattccttt acataggcga cagaattgtt tcttatttct caactaacga  24600
cttgtacgtt gctcttagag gacgtattga taaagacctc agcctttcta gaaaggttga  24660
gttatataac ggtgaatgtg tatacttgtt ttgtgaacac ccagctgttg gaatagtcaa  24720
cacagatttc aaattagaaa tccactaaga tgttccttaa gctagtggat gatcatgctt  24780
tggttgttaa tgtactactc tggtgtgtgg tgcttatagt gatactacta gtgtgtatta  24840
caataattaa actaattaag ctttgtttca cttgccatat gttttgtaat agaacagttt  24900
atggccccat taaaaatgtg taccacattt accaatcata tatgcacata gaccctttcc  24960
ctaaacgagt tattgatttc taaactaaac gacaatgtca aatgacaatt gtacgggtga  25020
```

```
cattgtcacc catttgaaga attggaattt tggttggaat gttattctaa ccatattcat  25080
tgttattctt cagtttggac actataaata ctccagattg ttttatggtt tgaagatgct  25140
tgtactgtgg cttctttggc cactcgtact tgctttgtca atctttgaca cctgggctaa  25200
ttgggattct aattgggcct ttgttgcatt tagctttttt atggccgtat caacactcgt  25260
tatgtgggtg atgtacttcg caaacagttt cagacttttc cgacgtgctc gaactttttg  25320
ggcatggaat cctgaggtta atgcaatcac tgtcacaacc gtgttgggac agacatacta  25380
tcaacccatt caacaagctc caacaggcat tactgtgacc ttgctgagcg gcgtgcttta  25440
cgttgacgga catagattgg cttcaggtgt tcaggttcat aacctacctg aatacatgac  25500
agttgccgtg ccgagcacta ctataattta tagtagagtc ggaaggtccg taaattcaca  25560
aaatagcaca ggctgggttt tctacgtacg agtaaaacac ggtgattttt ctgcagtgag  25620
ctctcccatg agcaacatga cagaaaacga aagattgctt catttttttct aaactgaacg  25680
aaaagatggc tacagtcaaa tggctgatg catctgaacc acaacgtggt cgtcagggta  25740
gaatacctta ttctctttat agccctttgc ttgttgatag tgaacaacct tggaaggtga  25800
tacctcgtaa tttggtaccc atcaacaaga aagacaaaaa taagcttata ggctattgga  25860
atgttcaaaa acgtttcaga actagaaagg gcaaacgggt ggatttgtca cccaagctgc  25920
atttttatta tcttggcaca ggaccccata aagatgcaaa atttagagag cgtgttgaag  25980
gtgtcgtctg ggttgctgtt gatggtgcta aaactgaacc tacaggttac ggtgttaggc  26040
gcaagaattc agaaccagag ataccacact tcaatcaaaa gctcccaaat ggtgttactg  26100
ttgttgaaga acctgactcc cgtgctcctt cccggtctca gtcgaggtcg cagagtcgcg  26160
gtcgtggtga atccaaacct caatctcgga atccttcaag tgacagaaac cataacagtc  26220
aggatgacat catgaaggca gttgctgcgg ctcttaaatc tttaggtttt gacaagcctc  26280
aggaaaaaga taaaaagtca gcgaaaacgg gtactcctaa gccttctcgt aatcagagtc  26340
ctgcttcttc tcaaacttct gccaagagtc ttgctcgttc tcagagttct gaaacaaaag  26400
aacaaaagca tgaaatgcaa aagccacggt ggaaaagaca gcctaatgat gatgtgacat  26460
ctaatgtcac acaatgtttt ggccccagag accttgacca caactttgga agtgcaggtg  26520
ttgtggccaa tggtgttaaa gctaaaggct atccacaatt tgctgagctt gtgccgtcaa  26580
cagctgctat gctgtttgat agtcacattg tttccaaaga gtcaggcaac actgtggtct  26640
tgactttcac tactagagtg actgtgccca aagaccatcc acacttgggt aagtttcttg  26700
aggagttaaa tgcattcact agagaaatgc aacaacatcc tcttcttaac cctagtgcac  26760
tagaattcaa cccatctcaa acttcacctg caactgctga accagtgcgt gatgaagttt  26820
ctattgaaac tgacataatt gatgaagtaa actaaacatg ccactgtgtt gtttgaaatt  26880
caggctttag ttggaatttt gcttttgttc tttcttttat tatctttctt ttgcctgttt  26940
ttagagagat ttggcgcctt ggtgccgtag atgaatacat tgcttttctc tgatctatgt  27000
atgatggtac gatcagagct gcttttaatt aacatgatcc cttgctttgg cttgacaagg  27060
atctagtctt atacacaatg gtaagccagt ggtagtaaag gtataagaaa tttgctacta  27120
tgttactgaa cctaggtgaa cgctagtata actcattaca aatgtgctgg agtaatcaaa  27180
gatcgcattg acgagccaac aatggaagag ccagtcattt gtcttgagac ctatctagtt  27240
agtaactgct aatggaacgg tttcgatatg gatacacaaa aaaaaaaaaa aaaaaaaaaa  27300
aaaaaaaaaa aaaaaaa                                                 27317
```

-continued

<210> SEQ ID NO 6
<211> LENGTH: 234
<212> TYPE: DNA
<213> ORGANISM: Human coronavirus 229E

<400> SEQUENCE: 6
atgttcctta agctagtgga tgatcatgct ttggttgtta atgtactact ctggtgtgtg 60
gtgcttatag tgatactact agtgtgtatt acaataatta aactaattaa gctttgtttc 120
acttgccata tgttttgtaa tagaacagtt tatggcccca ttaaaaatgt gtaccacatt 180
taccaatcat atatgcacat agaccctttc cctaaacgag ttattgattt ctaa 234

<210> SEQ ID NO 7
<211> LENGTH: 678
<212> TYPE: DNA
<213> ORGANISM: Human coronavirus 229E

<400> SEQUENCE: 7
atgtcaaatg acaattgtac gggtgacatt gtcacccatt tgaagaattg gaattttggt 60
tggaatgtta ttctaaccat attcattgtt attcttcagt ttggacacta taaatactcc 120
agattgtttt atggtttgaa gatgcttgta ctgtggcttc tttggccact cgtacttgct 180
ttgtcaatct ttgacacctg ggctaattgg gattctaatt gggcctttgt tgcatttagc 240
ttttttatgg ccgtatcaac actcgttatg tgggtgatgt acttcgcaaa cagtttcaga 300
cttttccgac gtgctcgaac tttttgggca tggaatcctg aggttaatgc aatcactgtc 360
acaaccgtgt tgggacagac atactatcaa cccattcaac aagctccaac aggcattact 420
gtgaccttgc tgagcggcgt gctttacgtt gacggacata gattggcttc aggtgttcag 480
gttcataacc tacctgaata catgacagtt gccgtgccga gcactactat aatttatagt 540
agagtcggaa ggtccgtaaa ttcacaaaat agcacaggct gggttttcta cgtacgagta 600
aaacacggtg atttttctgc agtgagctct cccatgagca acatgacaga aaacgaaaga 660
ttgcttcatt ttttctaa 678

<210> SEQ ID NO 8
<211> LENGTH: 3522
<212> TYPE: DNA
<213> ORGANISM: Human coronavirus 229E

<400> SEQUENCE: 8
atgtttgttt tgcttgttgc atatgccttg ttgcatattg ctggttgtca aactacaaat 60
gggctgaaca ctagttactc tgtttgcaac ggctgtgttg gttattcaga aaatgtattt 120
gctgttgaga gtggtggtta tataccctcc gactttgcat tcaataattg gttccttcta 180
actaatacct catctgttgt agatggtgtt gtgaggagtt ttcagccttt gttgcttaat 240
tgcttatggt ctgtttctgg cttgcggttt actactggtt ttgtctattt taatggtact 300
gggagaggtg attgtaaagg tttttcctca gatgttttgt ctgatgtcat acgttacaac 360
ctcaattttg aagaaaacct tagacgtgga accattttgt ttaaaacatc ttatggtgtt 420
gttgtgtttt attgtaccaa caacacttta gtttcaggtg atgctcacat accatttggt 480
acagttttgg gcaatttttta ttgctttgta aatactacta ttggcaatga aactacgtct 540
gcttttgtgg gtgcactacc taagacagtt cgtgagtttg ttatttcacg cacaggacat 600
ttttatatta atggctatcg ctatttcact ttaggtaatg tagaagccgt taatttcaat 660
gtcactactg cagaaaccac tgatttttgt actgttgcgt tagcttctta tgctgacgtt 720

-continued

```
ttggttaatg tgtcacaaac ctctattgct aatataattt attgcaactc tgttattaac    780
agactgagat gtgaccagtt gtcctttgat gtaccagatg gtttttattc tacaagccct    840
attcaatccg ttgagctacc tgtgtctatt gtgtcgctac ctgtttatca taaacatacg    900
tttattgtgt tgtacgttga cttcaaacct cagagtggcg gtggcaagtg ctttaactgt    960
tatcctgctg gtgttaatat tacactggcc aattttaatg aaactaaagg gcctttgtgt   1020
gttgacacat cacacttcac taccaaatac gttgctgttt atgccaatgt tggtaggtgg   1080
agtgctagta ttaacacggg aaattgccct ttttcttttg gcaaagttaa taactttgtt   1140
aaatttggca gtgtatgttt ttcgctaaag gatatacccg gtggttgcgc aatgcctata   1200
gtggctaatt gggcttatag taagtactat actataggct cattgtatgt ttcttggagt   1260
gatggtgatg gaattactgg cgtcccacaa cctgttgagg gtgttagttc ctttatgaat   1320
gttacattgg acaaatgtac taaatataat atttatgatg tatctggtgt gggtgttatt   1380
cgcgttagca atgacacctt tcttaatgga attacgtaca catcaacttc aggtaacctt   1440
ctgggtttta aagatgttac taagggcacc atctactcta tcactccttg taacccacca   1500
gatcagcttg ttgtttatca gcaagctgtt gttggtgcta tgttgtctga aaattttact   1560
agttacggct tttctaatgt tgtagaactg ccgaaatttt tctatgcgtc caatggcact   1620
tataattgca cagacgctgt tttaacttat tctagttttg gcgtttgtgc agatggttct   1680
ataattgctg ttcaaccacg taatgtttca tatgatagtg tttcagctat cgtcacagct   1740
aatttgtcta taccttccaa ttggaccact tcggtccagg ttgagtattt acaaattaca   1800
agtacaccta tcgtagttga ttgctccact tatgtttgca atggtaatgt gcgctgtgtt   1860
gaattgctta agcagtatac ttctgcttgt aaaactattg aagacgcctt aagaaatagc   1920
gccaggctgg agtctgcaga tgttagtgag atgctcactt ttgacaagaa agcgtttaca   1980
cttgctaatg ttagtagttt tggtgactac aaccttagca gcgtcatacc tagcttgccc   2040
acaagtggta gtagagtggc tggtcgcagt gccatagaag acatactttt tagcaaactt   2100
gttacttctg gacttggcac tgtggacgca gactacaaaa agtgcactaa gggtctttcc   2160
attgctgact tggcttgtgc tcaatattat aatggcatta tggttttgcc tggcgtcgct   2220
gatgctgaac gaatggccat gtatacaggt tctttaattg gtggaattgc tttaggaggt   2280
ctaacatcag ccgtttcaat accattttca ttagcaattc aggcacgttt aaattatgtt   2340
gcattgcaga ctgatgtttt acaagaaaat cagaaaattc ttgctgcatc ttttaacaaa   2400
gcaatgacca acatagtaga tgcctttact ggtgttaatg atgctattac acaaacttca   2460
caagccctac aaacagttgc tactgcactt aacaagatcc aggatgttgt taatcaacaa   2520
ggcaactcat tgaaccattt aacttctcag ttgaggcaga attttcaagc tatctctagc   2580
tctattcagg ctatctatga cagacttgac actattcagg ctgatcaaca agtagatagg   2640
ctgattactg gtagattggc tgctttgaat gtattcgttt ctcatacatt gactaagtac   2700
actgaagttc gtgcttccag acagcttgca caacaaaaag tgaatgagtg tgtcaaatcc   2760
cagtctaagc gttatggctt ctgtggaaat ggcactcaca ttttctcaat tgttaatgct   2820
gctcctgagg ggcttgtttt tctccacact gtcttgttgc cgacacaata taaggatgtt   2880
gaagcgtggt ctgggttgtg cgttgatggt acaaacggtt atgtgttgcg acaacctaat   2940
cttgctcttt acaaagaagg caattattat agaatcacat ctcgcataat gtttgaacca   3000
cgtattccta ccatggcaga ttttgttcaa attgaaaatt gcaatgtcac atttgttaac   3060
```

-continued

```
atttctcgct ctgagttgca aaccattgtg ccagagtata ttgatgttaa taagacgctg   3120

caagaattaa gttacaaatt gccaaattac actgttccag acctagttgt cgaacagtac   3180

aaccagacta ttttgaattt gaccagtgaa attagcaccc ttgaaaataa atctgcggag   3240

cttaattaca ctgttcaaaa attgcaaact ctgattgaca acataaatag cacattagtc   3300

gacttaaagt ggctcaaccg ggttgagact tacatcaagt ggccgtggtg ggtgtggttg   3360

tgcatttcag tcgtgctcat ctttgtggtg agtatgttgc tattatgttg ttgttctact   3420

ggttgctgtg gcttctttag ttgttttgca tcttctatta gaggttgttg tgaatcaact   3480

aaacttcctt attacgacgt tgaaaagatc cacatacagt aa                      3522
```

<210> SEQ ID NO 9
<211> LENGTH: 30738
<212> TYPE: DNA
<213> ORGANISM: Human coronavirus OC43

<400> SEQUENCE: 9

```
gattgtgagc gatttgcgtg cgtgcatccc gcttcactga tctcttgtta gatctttttg     60

taatctaaac tttataaaaa catccactcc ctgtaatcta tgcttgtggg cgtagatttt    120

tcatagtggt gtttatattc atttctgctg ttaacagctt tcagccaggg acgtgttgta    180

tcctaggcag tggcccgccc ataggtcaca atgtcgaaga tcaacaaata cggtctcgaa    240

ctacactggg ctccagaatt tccatggatg tttgaggacg cagaggagaa gttggataac    300

cctagtagtt cagaggtgga tatgatttgc tccaccactg cgcaaaagct ggaaacagac    360

ggaatttgtc ctgaaaatca tgtgatggtg gattgtcgcc gacttcttaa acaagagtgt    420

tgtgtgcagt ctagcctaat acgtgaaatt gttatgaatg caagtccata tgatttggag    480

gtgctacttc aagatgcttt gcagtcccgt gaagcagttt tggttacaac ccccttaggt    540

atgtctttag aggcatgcta tgtgagaggt tgtaatccta aaggatggac catgggtttg    600

tttcggcgta gaagtgtgtg taacactggt cgttgcactg ttaataagca tgtggcctat    660

cagttatata tgattgatcc tgcaggtgtc tgtcttggtg caggtcaatt cgtgggttgg    720

gtcataccct tagcctttat gcctgtgcaa tcccggaaat ttattgttcc atgggttatg    780

tacttgcgta agcgtggcga aaagggtgct tacaataaag atcatggacg tggcggtttt    840

ggacatgttt atgattttaa agttgaagat gcttatgacc aggtgcatga tgagcctaag    900

ggtaagtttt ctaagaaggc ttatgcttta attagagggt atcgtggtgt taaaccactt    960

ctctatgtag accagtatgg ttgtgattat actggtagtc ttgcagatgg cttagaggct   1020

tatgctgata agacattgca agaaatgaag gcattatttc ctacttggag tcaggaactc   1080

ctttttgatg taattgtggc atggcatgtt gtgcgtgatc cacgttatgt tatgagattg   1140

cagagtgctg ctactatacg tagtgttgca tatgttgcta atcctactga agacttgtgt   1200

gatggttctg ttgttataaa agaacctgtg catgtttatg cagatgactc tattatttta   1260

cgtcaatata atttagttga cattatgagt catttttata tggaggcaga tacagttgta   1320

aatgcttttt atggtgttgc tttgaaagat tgcggttttg ttatgcagtt tggttacatt   1380

gattgcgaac aagactcgtg tgattttaaa ggttggattc ctggtaacat gatagatggt   1440

tttgcttgca ccacttgtgg tcatgtttat gaagtaggtg atttgatagc acaatcttca   1500

ggtgttttgc ctgttaaccc tgtattgcat actaagagtg cagcaggcta tggtggtttt   1560

ggttgtaaag attcttttac tctgtatggc caaactgtag tttattttgg aggttgtgtg   1620

tattggagtc cagcacgtaa tatatggatt cctatattaa aatcctctgt taagtcatat   1680
```

-continued

```
gacagtttgg tttatactgg agttttaggt tgcaaggcta ttgtaaagga aacaaatctc   1740
atttgcaaag ctttgtacct tgattatgtt caacacaagt gtggcaattt acaccaacgg   1800
gagttgctag gtgtttcaga tgtgtggcat aaacaattgc tattaaatag aggtgtttat   1860
aaacctctgt tagagaatat tgattatttt aatatgcggc gcgctaaatt tagtttagaa   1920
acttttactg tttgtgcaga tggctttatg ccttttcttt tagatgattt agttccacgc   1980
gcatattatt tggcagtaag tggtcaagca ttttgtgatt atgcagataa actttgccat   2040
gccgttgtgt ctaagagtaa agagttactt gatgtgtctc tggattcttt aggtgcagct   2100
atacattatt tgaattctaa gattgttgat ttggctcaac attttagtga ttttggaaca   2160
agtttcgttt ctaaaattgt tcatttcttt aagactttta ctactagcac tgctcttgca   2220
tttgcatggg ttttatttca tgttttgcat ggtgcttata tagtagtgga gagtgatata   2280
tattttgtta aaaacattcc tcgttatgct agtgctgttg cacaagcatt tcagagtgtt   2340
gctaaagttg tactggactc tttaagagtt acttttattg atggcctttc ttgttttaag   2400
attggacgta gaagaatttg tctttcaggc agaaaaattt atgaagttga gcgtggcttg   2460
ttacattcat cccaattgcc attagatgtt tatgatttaa ccatgcctag tcaagttcag   2520
aaagccaagc aaaaacctat ttatttaaaa ggttctggtt ctgatttttc attagcggat   2580
agtgtagttg aagttgttac aacttcactt acaccatgtg gttattctga accacctaaa   2640
gttgcagata aaatttgcat tgtggataat gtttatatgg ccaaggctgg tgacaaatat   2700
taccctgttg tggttgatga tcatgttgga ctcttggatc aagcatggag agttccttgt   2760
gctggaaggc gtgttacatt taaggaacag cctacagtaa aggagattat aagcatgcct   2820
aagattatta aggtttttta tgagcttgac aacgatttta atactatttt aaatactgcg   2880
tgtggagtgt ttgaagtgga tgatactgtt gatatggagg aattttatgc tgtggtgatt   2940
gatgccatag aagagaaact ttctccatgt aaggagcttg aaggtgtagg tgctaaagtt   3000
agtgcctttt tacagaaatt agaggataat cccctatttt tatttgatga ggctggcgag   3060
gaagttcttg ctcctaaatt gtattgtgcc tttacagctc ctgaagatga tgactttctt   3120
gaggaaagtg atgttgaaga agatgatgta gaaggtgagg aaactgattt aactgtcaca   3180
agtgctggac agccttgtgt tgctagtgaa caggaggagt cttctgaagt cttagaggac   3240
actttggatg atggtccaag tgtggagaca tctgattcac aagttgaaga agatgtagaa   3300
atgtcggatt ttgttgatct tgaatctgtg attcaggatt atgaaaatgt ttgttttgag   3360
ttttatacta cagagccaga atttgttaaa gttttgggtc tgtatgtgcc taaagcaact   3420
cgcaacaatt gctggttgcg atcagttttg gcagtgatgc agaaattgcc ctgtcaattt   3480
aaagataaaa atttgcagga tctttgggtg ttatacaagc aacagtatag tcagttgttt   3540
gttgatacct tggttaataa gatacctgct aatattgtac ttccacaagg tggttatgtt   3600
gctgattttg catattggtt tttaacctta tgtgattggc agtgtgttgc atactggaaa   3660
tgcattaaat gtgatttagc tcttaagctt aaaggcttgg atgctatgtt cttttatggt   3720
gatgttgttt cacatatatg caagtgtggt gagtctatgg tacttattga tgttgatgtg   3780
ccatttacag cccactttgc tcttaaagat aagttgtttt gtgcatttat tactaagcgt   3840
attgtgtata aagcagcttg tgttgtggat gttaatgata gtcattctat ggctgttgtt   3900
gatggtaaac aaattgatga tcatcgtatc actagtatta ctagtgataa gtttgatttt   3960
attattgggc atggtatgtc attttcaatg actacttttg aaattgccca attgtatggt   4020
```

-continued

```
tcttgtataa cacctaatgt gtgttttgtt aaaggtgata taattaaagt atctaagctt   4080
gttaaagcag aagttgttgt aaaccctgct aatggccata tggcacatgg tggtggtgtt   4140
gcaaaagcta ttgcagtagc agctggacag cagtttgtta aagagactac cgatatggtt   4200
aagtctaaag gagtttgtgc tactggagat tgttatgtct ctacaggggg caaattatgt   4260
aaaactgtgc ttaatgttgt tggacctgat gcgagaacac agggtaaaca aagttatgta   4320
ttgttagagc gtgtttataa acatcttaac aactatgact gtgttgttac aactttgatc   4380
tcagctggta tatttagtgt gccttctgat gtgtctttaa catatctact tggtactgct   4440
aagaaacaag ttgttcttgt tagcaataat caagaggatt ttgatcttat ttctaagtgt   4500
cagataactg ctgttgaggg cactaagaaa ttggcagcgc gtctttcttt taatgttgga   4560
cgttccattg tttacgaaac agatgctaat aagttgattt taatcaatga cgttgcattt   4620
gtttcgacat ttaatgtttt acaggatgtt ttatccttaa gacatgatat agcacttgat   4680
gatgatgcac gaaccttcgt tcagagcaat gttgatgttg tacctgaggg ttggcgtgtt   4740
gtcaataagt tttatcaaat taatggtgtt agaaccgtta agtattttga gtgtactgga   4800
ggcatagata tatgcagcca ggataaagtt tttggttatg tacagcaggg tatttttaat   4860
aaggctactg ttgctcaaat taaagccttg tttttggata aagtggacat cttgctaact   4920
gttgatggtg ttaatttcac taataggttt gtgcctgttg gtgaaagttt tggtaagagt   4980
ctaggaaatg tgttttgtga tggagttaat gtcacgaagc ataagtgtga tataaattat   5040
aaaggtaaag tctttttcca gtttgataat ctttctagtg aagatttaaa ggctgtaaga   5100
agttccttta attttgatca gaaggaattg cttgcctatt acaacatgct tgttaattgt   5160
tttaagtggc aggttgttgt taatggtaag tatttcactt ttaagcaagc taataacaat   5220
tgttttgtta atgtttcttg cttaatgctc cagagtttgc atctgacatt taaaattgtt   5280
caatggcaag aggcatggct tgaatttcgt tctggccgcc ctgctagatt tgtagctttg   5340
gttttggcca aaggtgggtt taaatttgga gatcctgctg attctagaga tttcttgcgt   5400
gttgtgttta gtcaagttga tttgactggg gcaatatgtg attttgaaat tgcatgtaaa   5460
tgtggtgtaa agcaggaaca gcgtactggt ctggacgctg ttatgcattt tggtacattg   5520
agtcgtgaag atcttgagat tggttatacc gtggactgtt cttgcggtaa aaagctaatt   5580
cattgtgtac gatttgatgt accattttta atttgcagta atacacctgc tagtgtaaaa   5640
ttacctaagg gtgtaggaag tgcaaatatt tttataggtg ataaggttgg tcattatgtt   5700
catgttaagt gtgaacaatc ttatcagctt tatgatgctt ctaatgttaa gaaggttaca   5760
gatgttactg gcaagttgtc agattgtctg tatcttaaaa atttgaaaca aacttttaaa   5820
tcggtgttaa ccacctatta tttggatgat gttaagaaaa ttgagtataa acctgacttg   5880
tcacaatatt attgtgacgg aggtaagtat tatactcagc gtattattaa agcccaattt   5940
aaaacattcg agaaagtaga tggtgtgtat actaatttta aattgatagg acacaccgtc   6000
tgtgacagtc ttaatgctaa gttgggtttt gatagctcta aagagtttgt tgaatataag   6060
attactgagt ggccaacagc tacaggtgat gtggtgttgg ctactgatga tttgtatgtt   6120
aagagatatg agaggggttg tattactttt ggtaaacctg ttatatggtt aagccatgag   6180
aaagcttccc tcaattcttt aacatatttt aatagacctt cattggttga tgataataaa   6240
tttgatgttt taaaagtgga tgatgttgac gatggtggtg acagctcaga gagtggtgcc   6300
aaagaaacca aagaaatcaa cattattaag ttaagtggtg ttaaaaaacc atttaaggtt   6360
gaagatagtg tcattgttaa tgatgatact agtgaaacca aatatgttaa gagtttgtct   6420
```

```
attgttgatg tgtatgatat gtggcttaca ggttgtaagt atgttgttag aactgctaat   6480
gctttgagca gagcagttaa cgtacctaca atacgtaagt ttataaaatt tggtatgact   6540
cttgttagta taccaattga tttgttaaat ttaagagaga ttaagcctgc tgttaatgtg   6600
gttaaagctg tgcgaaataa aatttctgta tgctttaatt ttattaaatg gctttttgtc   6660
ttattatttg gctggattaa aatatccgct gataataaag taatctacac cacagaaatt   6720
gcatcaaagc ttacgtgtaa gcttgtagct ttagctttta aaaatgcatt tttgacattt   6780
aagtggagta tggttgctag aggtgcttgc attatagcga ctatatttct attgtggttt   6840
aattttatat atgccaatgt aatttttagt gatttttatt tgcctaaaat cggtttcttg   6900
ccgacttttg ttggtaagat tgcacagtgg attaagaaca cttttagtct tgtaactatt   6960
tgtgatctat attccatgca ggatgtgggt tttaagaatc agtattgtaa tggaagtatt   7020
gcatgtcagt tctgcttggc aggatttgat atgttagata attataaagc cattgatgta   7080
gtacagtatg aagctgatag gagagcattt gttgattata caggtgtgtt aaagattgtc   7140
attgaattga tagttagtta cgccctgtat acggcatggt tttatccatt gtttgccctt   7200
atcagtattc agatcttgac cacttggctg cctgagcttt ttatgcttag tacattacat   7260
tggagtttta ggttgctggt ggctttagct aatatgttac cagcacatgt gtttatgagg   7320
ttttatatta ttattgcctc ttttattaag ctctttagct tgtttaggca tgttgcctat   7380
ggttgtagta aatctggttg tttgttttgt tacaagagga atcgtagtct acgtgttaaa   7440
tgtagtacta tcgttggtgg catgatacgc tattacgatg ttatggctaa tggtggcact   7500
ggcttttgtt caaaacatca atggaattgc attgattgtg attcttataa accaggtaat   7560
acttttatta ctgttgaggc cgctcttgat ctatctaagg aattgaaacg gcccattcag   7620
cctacagatg ttgcttatca tacggttact gatgttaagc aagttggttg ttctatgcgc   7680
ttgttctatg atcgtgatgg acagcgcaca tatgatgatg ttaatgctag tttgtttgtg   7740
gattatagta atttgctaca ttctaaggtt aagagtgtgc ctaatatgca tgttgtggta   7800
gtggaaaatg atgctgataa agccaatttt ctgaatgctg ctgtatttta tgcacagtct   7860
ttgtttagac ctattttaat ggttgataaa aatctgataa ctactgctaa cactggtacg   7920
tctgttacag aaactatgtt tgatgtttat gtggatacat tttgtctat gtttgatgtg   7980
gataaaaaga gtcttaatgc tttaatagca actgcgcatt cttctataaa acagggtacg   8040
cagatttata aagttttgga taccttttta agctgtgctc gtaaaagttg ttctattgat   8100
tcagatgttg atactaagtg tttagctgat tctgtcatgt ctgctgtatc ggcaggtctt   8160
gaattgacgg atgaaagttg taataacttg gtgccaacat atttgaagag tgacaacatt   8220
gtggcagctg atttaggtgt tctgattcaa aattctgcaa agcatgtgca gggtaatgtt   8280
gctaaaatag ctggtgtttc ctgtatatgg tctgtggatg cttttaatca gtttagttct   8340
gatttccagc ataaattgaa gaaagcatgt tgtaaaactg gtttgaaact gaagcttact   8400
tataataagc agatggctaa tgtctctgtt ttaactacac cctttagtct taaagggggt   8460
gcagttttta gttattttgt ttatgtgtgt tttgtgttga gtttggtctg ttttattgga   8520
ctgtggtgct taatgcccac ttacacagta cacaaatcag attttcagct tcccgtttat   8580
gccagttata aagttttaga taatggtgtt attagagatg ttagcgttga agatgtttgt   8640
ttcgctaaca aatttgaaca atttgatcaa tggtatgagt ctacatttgg tctaagttat   8700
tatagtaaca gtatggcttg tcccattgtt gttgctgtaa tagatcagga ttttggctct   8760
```

-continued

```
acagtgttta atgtccctac caaagtgtta cgatatggtt atcatgtgtt gcactttatt   8820
acacatgcac tttctgctga tggagtgcag tgttatacgc cacatagtca aatatcgtat   8880
tctaattttt atgctagtgg ctgtgtgctt tcctctgctt gcactatgtt tacaatggcc   8940
gatggtagtc cacaacctta ttgttataca gaggggctta tgcaaaatgc ttctctgtat   9000
agttcattgg tacctcacgt gcggtataat cttgctaatg ctaaaggttt tatccgtttt   9060
ccagaagtgt tgcgagaagg gcttgtacgt atcgtgcgta ctcgttctat gtcgtattgc   9120
agagttggat tatgtgagga agctgatgag ggtatatgct ttaattttaa tggttcttgg   9180
gtgcttaata atgattatta tagatcattg cctgggacct tttgtggtag agatgttttt   9240
gatttaattt atcagctatt taaaggttta gcacagcctg tggatttttt ggcattgact   9300
gctagttcca ttgctggtgc tatactcgct gtaattgttg ttttggtgtt ttattaccta   9360
ataaagctta aacgtgcttt tggtgattac accagtgttg tttttgttaa cgtgattgtg   9420
tggtgtgtaa attttatgat gctttttgtg tttcaagttt accccatact ttcttgtgta   9480
tatgctattt gttattttta tgccacgctt tatttccctt cggagataag tgtgataatg   9540
cacttacaat ggctagttat gtatggcact attatgcctt tatggttttg tttgctatat   9600
atagctgttg ttgtttcaaa tcatgctttt tgggtatttt cttactgcag aaagcttggt   9660
acttctgttc gtagtgatgg tacatttgaa gaaatggctc tcactacttt tatgattaca   9720
aaagattctt attgtaagct taagaattct ttgtctgatg ttgcttttaa tagatatttg   9780
agtttgtata ataaatatag gtattacagc ggtaaaatgg atactgctgc atatagggag   9840
gctgcttgct ctcagttggc taaagcaatg gacacattta ccaataataa tggtagtgat   9900
gtgctttacc aaccgcctac tgcttccgtc tcaacttcat tcttgcaatc tggtattgtg   9960
aaaatggtaa atcctacttc taaggtagaa ccatgtgttg tcagtgttac ctatggtaat  10020
atgacattga atggtttatg gttggatgac aaggtctact gtcccagaca tgtaatatgt  10080
tctgcttcag atatgactaa tccagattat acaaatttgt tgtgtagagt aacatcaagt  10140
gattttactg tattgtttga tcgtctaagc cttacagtga tgtcttatca aatgcggggt  10200
tgtatgcttg ttcttacagt gaccctgcaa aattctcgta cgccaaaata tacatttggt  10260
gtggttaaac ctggtgagac ttttactgtt ttagctgctt ataacggcaa accacaagga  10320
gcctttcatg taactatgcg tagtagttat accattaagg gttccttttt atgcggatct  10380
tgtggatctg ttggttatgt aataatgggt gattgtgtta aatttgttta tatgcatcaa  10440
ttggagctta gtactggttg tcatactggt actgacttca atggggattt ttatggtcct  10500
tataaggatg ctcaggttgt tcagttgctc attcaggatt atatacaatc tgttaatttt  10560
gtagcatggc tttatgctgc tatacttaac aattgtaatt ggtttgtaca aagtgataag  10620
tgttctgtag aagattttaa tgtgtgggct ctgtccaatg gatttagcca agttaaatct  10680
gaccttgtta tagatgcttt agcttctatg actggtgtgt ctttggaaac actgttggct  10740
gctattaagc gtcttaagaa tggtttccaa ggacgtcaga ttatgggtag ttgctctttt  10800
gaggatgaat tgacacctag cgatgtttat caacaactcg ctggtatcaa gttacaatca  10860
aaacgcacta gattgtttaa aggcactgtt tgttggatta tggcttctac atttttgttt  10920
agttgcataa ttacagcatt tgtgaaatgg actatgttta tgtatgtaac tactaatatg  10980
tttagtatta cgttttgtgc actttgtgtt ataagtttgg ccatgttgtt ggttaagcat  11040
aagcatcttt atttgactat gtatataact cctgtgcttt ttacactgtt gtataacaac  11100
tatttggttg tgtacaagca tacatttaga ggctatgtct atgcatggct atcatattat  11160
```

gttccatcag ttgagtacac ttatactgat gaagttattt atggcatgtt attgcttgta 11220
ggaatggtct ttgttacatt acgtagcatt aaccatgatt tgttttcttt tataatgttt 11280
gttggtcgtt tgatttctgt tttctctttg tggtacaagg gttctaactt agaggaagaa 11340
attcttctta tgttggcttc cctttttggt acttacacat ggacaacagt tttatctatg 11400
gctgtagcaa aggttattgc taagtgggtt gctgtgaatg tcttgtattt cacagatata 11460
cctcaaatta agatagtgct tttgtgctat ttgtttattg gttatattat tagctgttat 11520
tggggcttgt tttccttgat gaacagtttg tttagaatgc ctttgggtgt ttataattat 11580
aaaatttcag tacaggaatt aagatatatg aatgctaatg gattgcgccc tcctaagaat 11640
agttttgaag cccttatgct taattttaag ctgttgggta ttggaggtgt tccaatcatt 11700
gaagtatctc aatttcaatc aaaattgact gatgtcaaat gtgctaatgt cgtcttgctt 11760
aattgcttgc aacatttgca tgttgcttct aattctaagt tgtggcatta ttgtagcact 11820
ttgcacaatg aaatacttgc cacttcggat ctgagtgttg cttttgaaaa gcttgctcag 11880
ttattaattg ttttgtttgc taatccagct gctgtggata gcaagtgcct gactagtatt 11940
gaagaagttt gcgatgatta cgcaaaggac aatactgttt tgcaggcttt acagagtgaa 12000
tttgttaata tggctagctt cgttgaatat gaagttgcta agaaaaatct tgatgaggcg 12060
cgttttagtg gttctgctaa tcaacagcag ttaaaacagc tagagaaagc ctgtaatatt 12120
gctaaatctg cttatgaacg cgaccgtgct gtagcaaaaa agttggagcg tatggctgat 12180
ttggctctca ctaatatgta taaagaagct agaattaatg ataagaagag taaggttgtt 12240
tctgccttgc aaactatgct tttagtatg gtgcgtaagt tagataatca agctctgaat 12300
tcaatattag ataacgctgt gaagggttgt gtaccattga atgcaatacc ttcattggca 12360
gcaaatactc tgaatataat tgtaccagat aaaagtgttt atgaccaggt agttgataat 12420
gtctatgtta cctatgcggg taatgtatgg cagattcaaa ctatccagga ttcagatggt 12480
acaaataagc agttgaatga gatatctgat gattgtaact ggccactagt tattattgca 12540
aatcggtata atgaggtatc tgctactgtt ttgcaaaata atgaattaat gcctgctaag 12600
ttgaaaattc aggttgttaa tagtggtcca gatcagactt gtaatacacc tactcaatgt 12660
tactataata atagtaacaa tgggaagatt gtttatgcta tacttagtga tgttgatggt 12720
cttaagtata caaaaattct taaagatgat ggcaattttg ttgttttgga gttagatcct 12780
ccttgtaaat ttactgttca agatgctaaa ggtcttaaaa ttaagtacct ttattttgta 12840
aaaggttgta acacactagc aagaggctgg gttgttggta caatttcttc tacagttaga 12900
ttgcaagctg gaactgctac tgaatatgct tccaactcat ctatattgtc tttatgtgcg 12960
ttttctgtag atcctaagaa aacgtattta gattttatac aacaaggagg aacacctatt 13020
gccaattgtg ttaaaatgtt gtgtgaccat gctggtaccg gtatggccat tactgttaaa 13080
cccgatgcta ccactagtca ggattcatat ggtggtgcgt ctgtttgtat atattgccgc 13140
gcacgagttg aacacccaga tgttgatggg ttgtgcaaat tacgcggcaa gtttgtacaa 13200
gtgcctgtag gtataaaaga tcctgtgtct tatgttttga cacatgatgt ttgtcgagtt 13260
tgtggatttt ggcgggatgg aagttgttca tgtgttagca ctgacactac tgttcaatca 13320
aaagatacta attttttaaa cgggttcggg gtacgagtgt agatgcccgt ctcgtaccct 13380
gcgccagtgg tttatctact gatgtacaat taagggcatt tgatatttac aatgctagtg 13440
ttgctggcat tggtttacat ttaaaagtta attgttgccg ttttcagcgt gttgatgaga 13500

-continued

```
acggtgataa attagatcag ttctttgttg ttaagaggac agatctgact atatataata  13560
gagagatgaa atgctatgag cgtgtaaaag attgtaagtt tgtggctgaa cacgatttct  13620
ttacatttga tgtagaaggt agtcgtgtgc cacacattgt acgcaaggat ttaacaaagt  13680
atactatgtt ggatctttgc tatgcattgc gacattttga tcgcaatgat tgcatgctgc  13740
tttgtgacat tctctctata tatgctggtt gtgaacaatc ctactttact aagaaggatt  13800
ggtatgattt tgttgaaaat cctgatatta ttaatgtgta taaaaagcta ggacctattt  13860
ttaatagagc cctagttagc gctactgagt ttgcggacaa attggtggag gtaggcttag  13920
taggcgtttt aacacttgat aatcaagatt taaatggtaa atggtatgat tttggtgact  13980
atgttattgc agccccagga tgtggtgttg ctatagcaga ttcttattat tcttatatca  14040
tgcctatgct gaccatgtgt catgcattgg attgcgaatt gtatgtgaat aatgcttata  14100
gactatttga tcttgtacag tatgatttta ctgattacaa gcttgaattg tttaataagt  14160
attttaagca ctggagtatg ccatatcatc ctaacactgt tgattgtcag gatgatcggt  14220
gtattataca ttgtgctaat tttaacatac tttttagtat ggttttacct aatacatgtt  14280
ttgggcctct tgttaggcaa atttttgtgg atggtgtgcc ttttgttgtt tcaattggct  14340
accattataa agaacttggt attgtgatga atatggatgt ggatacacat cgttatcgct  14400
tgtctttaaa agacttgctt ttatatgctg ctgatccagc tttgcatgta gcttctgcta  14460
gtgcattgta tgatttacgc acttgctgtt ttagtgttgc cgctataaca agcggtgtaa  14520
aatttcaaac agttaaacct ggtaatttta atcaggattt ttatgatttt gttttaagta  14580
aaggcctgct taaagagggt agctcagttg atctgaagca ctttttcttt acacaggatg  14640
gtaatgctgc tattactgat tataattatt ataagtataa tttgcccacc atggtggaca  14700
ttaagcagtt gttgtttgtt ttggaagttg tttataagta ttttgagatt tatgatggtg  14760
ggtgtatacc ggcatcacaa gtcattgtta ataattatga taagagtgct ggctatccat  14820
ttaacaaatt tggaaaagcc aggctctatt atgaagcatt atcatttgag gaacaggatg  14880
aaatttacgc ttatactaag cgtaatgtcc tgccaacact tactcaaatg aatttgaaat  14940
atgctattag tgctaagaat agagcccgca ctgttgctgg tgtttccata cttagtacta  15000
tgactggcag aatgtttcat caaaaatgtt tgaaaagtat agcagctaca cgtggtgttc  15060
ctgtagttat aggcaccact aaattttatg gtggctggga tgatatgtta cgccgcctta  15120
ttaaagatgt tgacaatcct gtacttatgg gttgggatta tcctaagtgt gatcgtgcta  15180
tgccaaacct actacgtatt gttagtagtt tggtattagc ccgaaaacat gagacatgtt  15240
gttcgcaaag cgataggttt tatcgacttg cgaatgaatg cgcacaagtt ttgagtgaaa  15300
ttgttatgtg tggtggctgt tattatgtta agcctggtgg cactagtagt ggtgatgcaa  15360
ctactgcttt tgctaattca gtctttaaca tatgtcaagc tgtttcagcc aatgtatgtg  15420
ccttaatgtc atgcaatggc aataagattg aagatcttag tatacgtgct cttcagaagc  15480
gcttatactc acatgtgtat agaagtgata aggttgattc aacctttgtc acagaatatt  15540
atgaattttt aaataagcat tttagtatga tgattttgag tgatgatggg gttgtgtgtt  15600
ataattctga ttatgcgtcc aaagggtata ttgctaatat aagtgccttt caacaggtat  15660
tatattatca aaataacgtt tttatgtcag aatccaaatg ttgggttgaa catgacataa  15720
ataatggacc tcatgaattc tgttcacaac acacaatgct tgtaaagatg gatggtgacg  15780
atgtctacct tccatatcct aatcctagtc gtatattagg agctggatgt tttgtagatg  15840
atttgttaaa gactgatagt gttcttttaa tagaacgatt tgtaagtctt gcaatagatg  15900
```

```
cttatccact tgtgtatcat gaaaatgaag aataccaaaa ggtttttcgt gtttatttgg  15960
cgtatataaa gaagttgtac aatgacctgg gtaatcagat cttggatagc tacagtgtta  16020
ttttaagtac ttgtgatgga caaaagttca ctgatgagtc cttttacaag aacatgtatt  16080
taagaagtgc agttatgcag agtgttggag cttgcgtggt ctgctcttct caaacatcat  16140
tacgttgtgg cagttgcatc agaaagcctc ttctttgctg caagtgttgt tatgatcatg  16200
ttatggcgac tgatcataaa tatgtcttga gtgtttcacc atatgtgtgt aatgcaccag  16260
gatgtgatgt aaatgatgtt accaaattgt atctaggtgg tatgtcatat tattgtgaag  16320
accataagcc acaatattca ttcaagttgg taatgaatgg tctggttttt ggtctatata  16380
aacaatcttg tacaggatct ccgtacatag acgattttaa tcgtatagct agttgtaaat  16440
ggaccgatgt ggatgattac atactagcta atgaatgtac agagcgcttg aaattgtttg  16500
ctgcagaaac gcaaaaggca accgaggaag cctttaagca gagttatgca tcagcaacaa  16560
tacaagagat tgttagtgag cgcgaattga ttctctcttg ggagattgga aaagttaagc  16620
caccacttaa taaaaattat gtttttactg gctaccattt tactaaaaat ggtaagacag  16680
ttttaggtga gtatgttttt gataagagtg agttgactaa tggtgtgtat tatcgcgcca  16740
caaccactta taagctatct gtaggagatg tttttgtttt aacctctcat tcagtagcta  16800
atttaagtgc tcctacgctt gttccgcagg agaattatag tagtattaga tttgctagtg  16860
tttatagtgt gcttgagacg tttcagaaca atgttgttaa ttatcaacac attggtatga  16920
aacgttactg caccgtgcaa ggacctcctg gtacagggaa gtcacatctt gctattggtc  16980
ttgctgtatt ctattgtaca gcacgtgttg tatacacagc ggccagccat gcagctgttg  17040
acgcattgtg tgaaaaagca tataaatttt tgaatataaa tgattgcact cgtattgttc  17100
cggccaaggt cagggtggag tgctatgata agtttaaaat taatgacacc actcgtaagt  17160
atgtgtttac taccataaat gcattacctg agatggtgac tgatattgtt gttgtagatg  17220
aagttagtat gcttaccaat tatgagcttt ctgttattaa tgctcgtatt cgcgctaagc  17280
attatgttta tattggtgat cctgctcaat tgccagcacc acgtgtgtta ttgagcaagg  17340
gtacacttga acctaaatat tttaacactg ttactaagct catgtgttgc ttagggccag  17400
acatttttct tggtacatgt tatagatgtc ctaaggaaat cgttgataca gtgtccgcct  17460
tggtttatga aaataagctt aaggctaaga atgagagtag ttcattgtgt tttaaggtct  17520
attataaggg cgttacaaca catgaaagtt ctagtgctgt aaatatgcag cagatttatt  17580
tgattaataa gtttttgaag gctaaccctt tgtggcataa agctgttttt attagcccat  17640
ataatagtca gaactttgca gctaagcgtg ttttgggttt acaaacccaa accgtggatt  17700
ctgctcaagg ttctgaatat gattatgtta tatattcaca gactgcagaa acagcgcatt  17760
ctgtaaatgt taatcgcttc aatgttgcta ttactcgagc caagaaaggt attctttgtg  17820
ttatgagtaa tatgcagttg tttgaagcat tacagtttac tacattgacc ttagataaag  17880
tgccacaggc cgtcgaaact aaagttcaat gtagtactaa tttatttaaa gattgtagca  17940
agagttatag cggttatcac ccagctcatg ctccttcatt tttggcagta gatgacaaat  18000
ataaggcaac tggcgattta gccgtgtgtc ttggtattgg tgattctgct gttacatatt  18060
caagattaat atcactcatg ggttttaaat tggatgttac ccttgatggg tattgtaagc  18120
tttttataac taaagaagaa gctgttaaac gcgtgcgtgc ctgggttggc tttgatgctg  18180
aaggtgctca tgccacgcgt gatagcattg ggacaaattt cccacttcaa ttaggatttt  18240
```

```
ccacaggaat tgattttgtt gtggaagcca ctggtttgtt tgctgataga gatggttaca  18300
gctttaaaaa ggctgtggcg aaagctcctc ctggtgaaca atttaagcac ctcatccctt  18360
tgatgacgag aggtcatcgc tgggatgttg ttagacctag aatagtacaa atgtttgcag  18420
atcatttaat tgatctgtct gattgtgttg tgctagttac atgggcagcc aactttgagc  18480
tcacttgtct ccgctacttt gcaaaagtag ggcgtgagat ttcttgtaat gtatgcacta  18540
aacgtgccac agtttacaat tctagaactg gttactatgg ttgttggcgc catagtgtta  18600
catgtgatta cttgtataat ccacttattg ttgatattca acagtgggga tatattggtt  18660
ctttatcaag taatcatgat ttatattgta gtgtccataa aggagcacat gttgcttcct  18720
ctgatgctat aatgacacgg tgtttggccg tttatgattg cttttgcaat aatattaatt  18780
ggaatgtgga gtatcccatc atttcaaatg agttaagtat taatacctct tgtagggtct  18840
tgcagcgtgt gattcttaaa gctgccatgc tctgcaacag atatactttg tgttatgata  18900
ttggcaaccc aaaagcgatt gcctgtgtca aagattttga ttttaagttc tatgatgccc  18960
aaccaattgt taagtctgtt aagactcttt tgtattcttt tgaggcacat aaggactctt  19020
ttaaagacgg tttgtgtatg ttttggaact gtaatgtgga taagtatcca ccgaatgcag  19080
ttgtatgtag atttgacact agagtgttga ataatttaaa tcttcctggc tgtaatggag  19140
gtagtttgta tgttaataaa catgcattcc acactaaacc ctttgctagg gcagcctttg  19200
agcatttgaa gcctatgcca ttcttctatt attcagatac gccttgtgtg tatatggatg  19260
gcatggatgc taagcaggtt gattatgtac ctttgaaatc tgccacgtgc atcacaagat  19320
gcaatttagg tggtgcagtt tgtttaaaac atgctgaaga gtatcgtgag tacttagagt  19380
cttacaatac agctactaca gcaggtttta ctttttgggt ctataagaca tttgattttt  19440
ataatttgtg gaatacgttc accaagctac aaagcttgga gaatgttgta tataatttag  19500
tcaagactgg tcattataca ggacaggctg gtgaaatgcc ttgtgccatt ataaatgata  19560
aagttgtggc taagatcgat aaggaggatg ttgtcatttt tattaataat acaacatacc  19620
ctactaatgt ggccgttgaa ttatttgcca agcgcagtgt tcgacaccac ccagagctta  19680
agctctttag aaatttaaat atagacgtgt gttggaagca cgtcatttgg gattatgcta  19740
gagaaagtat attttgcagt aatacctatg gtgtctgcat gtatacagat ttaaagttca  19800
ttgataaatt gaatgtcctt tttgatggtc gtgataatgg tgctcttgaa gcttttaaac  19860
gttctaataa tggcgtttac atttccacga caaaagttaa gagtctttcg atgataagag  19920
gtccaccgcg tgctgaatta aatggcgtag tggtggacaa ggttggagac actgattgtg  19980
tgttttattt tgctgtgcgt aaagaaggtc aggatgtcat cttcagccaa ttcgacagcc  20040
tgggagtcag ctctaaccag agcccacaag gtaatctggg gagtaatggt aaacccggta  20100
atgtcggtgg taatgatgct ctgtcaatct ctactatctt tacacaaagc cgtgttatta  20160
gctcttttac atgtcgtact gatatggaaa aagattttat agctttagat caagatgtgt  20220
ttattcagaa gtatggtttg gaggactatg cctttgaaca cattgtttat ggtaacttca  20280
accagaagat tattggtggt ttgcatttgt taataggctt gtaccgaaga cagcaaactt  20340
ccaatctggt tgttcaggag tttgtttcat atgactccag catacactct tattttatca  20400
ctgacgagaa gagtggtggt agtaagagtg tttgcactgt tatagatatt ttgttggatg  20460
attttgtggc tcttgttaag tcacttaatc ttaattgtgt gagtaaggtt gttaatgtta  20520
atgttgattt taaagatttt cagtttatgc tttggtgtaa cgatgagaaa gttatgactt  20580
tctatcctcg tttgcaagct gcatctgact ggaagcctgg ttattctatg cctgtattat  20640
```

```
ataagtattt gaattctcca atggaaagag ttagtctctg gaattatggg aagccagtta  20700
ctttgcctac aggctgtatg atgaatgttg ctaagtatac tcagttatgt caatatctga  20760
atactacaac attagctgta cctgttaata tgcgagtttt gcatttaggt gcaggttcag  20820
aaaaaggagt agcaccgggt tctgcagttc ttaggcagtg gttgcctgct ggtactattc  20880
ttgtagataa cgatttatac ccatttgtta gtgacagtgt cgctacatat tttggggatt  20940
gtataacttt accctttgat tgtcaatggg atttgataat ttctgatatg tatgacccta  21000
ttactaagaa catagggggag tacaatgtga gtaaagatgg tttctttaca tacatttgtc  21060
atatgattcg agacaagtta gctctgggtg gcagtgttgc tataaaaata acagagtttt  21120
cttggaatgc agaattatat aagttaatgg ggtattttgc attttggact gtgttttgca  21180
caaatgcaaa tgcttcttct agtgaaggat ttttaattgg cataaattat ttgtgtaagc  21240
ccaaggttga gatagatgga aatgttatgc atgccaatta tttgttttgg agaaattcca  21300
cagtttggaa cgggggtgct tatagcctgt ttgatatggc taaattcccg cttaagttgg  21360
ctggtactgc cgtaataaat ttaagagcag accagattaa tgatatggtt tattcccttc  21420
ttgaaaaggg taaactactt attagagata caaataaaga agttttcgtt ggtgacagtt  21480
tggttaatgt aatctaaact ttaaaaatgg ctgtcgctta tgcagacaag cctaatcatt  21540
ttatcaattt tccacttacc cattttcagg gttttgtgtt aaattataaa ggtttacaat  21600
ttcaaattct cgatgaagga gtggattgta aaatacaaac agcgccacac attagtctta  21660
ctatgctgga catacagcct gaagactata aaagtgttga tgtcgctatt caagaagtta  21720
ttgatgatat gcattggggt gatggtttc agattaaatt tgagaatcct cacatcctag  21780
gaagatgcat agttttagat gttaaaggtg tagaagaatt gcatgacgat ttagttaatt  21840
acattcgtga taaaggttgt gttgctgacc aatccaggaa atggattggc cattgcacca  21900
tagctcaact cacggatgca gcactgtcca ttaaggaaaa tgttgatttt ataaacagca  21960
tgcaattcaa ttataaaatc accatcaacc cctcatcacc ggctagactt gaaatagtta  22020
agctcggtgc tgaaaagaaa gatggttttt atgaaaccat agttagtcac tggatgggaa  22080
ttcgttttga atacacatca cccactgata agctagctat gattatgggt tattgttgtt  22140
tagatgtggt acgtaaagag ctagaagaag gcgatcttcc cgagaatgat gatgatgctt  22200
ggtttaagct atcgtaccat tatgaaaaca attcttggtt cttccgacat gtctacagga  22260
aaagttttca tttccgtaag gcttgtcaaa atttagattg taattgtttg gggttttatg  22320
aatcttcagt tgaagaatat taaactcagt gaaaatgttt ttgcttccta gatttattct  22380
agttagctgc ataattggta gcttaggttt ttacaaccct cctaccaatg ttgtttcgca  22440
tgtaaatgga gattggtttt tatttggtga cagtcgttca gattgtaatc atattgttaa  22500
tatcaacccc cataattatt cttatatgga ccttaatcct gttctgtgtg attctggtaa  22560
aatatcatct aaagctggca actccatttt taggagtttt cactttaccg atttttataa  22620
ttacacaggc gaaggtcaac aaattatttt ttatgagggt gttaatttta cgccttatca  22680
tgcctttaaa tgcaaccgtt ctggtagtaa tgatatttgg atgcagaata aaggcttgtt  22740
ttatactcag gtttataaga atatggctgt gtatcgcagc cttacttttg ttaatgtacc  22800
atatgtttat aatggctccg cacaagctac agctctttgt aaatctggta gtttagtcct  22860
taataaccct gcatatatag ctcctcaagc taactctggg gattattatt ataaggttga  22920
agctgatttt tatttgtcag gttgtgacga gtatatcgta ccactttgta tttttaacgg  22980
```

```
caagtttttg tcgaatacaa agtattatga tgatagtcaa tattatttta ataaagacac  23040
tggtgttatt tatggtctca attctacaga aaccattacc actggttttg atcttaattg  23100
ttattattta gttttaccct ctggtaatta tttagccatt tcaaatgagc tattgttaac  23160
tgttcctacg aaagcaatct gtcttaataa gcgtaaggat tttacgcctg tacaggttgt  23220
tgattcgcgg tggaacaatg ccaggcagtc tgataacatg acggcggttg cttgtcaacc  23280
tccgtactgt tattttcgta attctactac caactatgtt ggtgtttatg atattaatca  23340
tggagatgct ggttttacta gcatacttag tggtttgtta tataattcac cttgtttttc  23400
gcagcaaggc gtttttaggt atgataatgt tagcagtgtc tggcctctct acccctatgg  23460
cagatgtccc actgctgctg atattaatat ccctgattta cccatttgtg tgtatgatcc  23520
gctaccagtt attttgcttg gcattctttt gggcgttgcg attgtaatta ttgtagtttt  23580
gttgttatat tttatggtgg ataatgttac taggctgcat gatgcttaga ccataatcta  23640
aacatgtttt tgatactttt aatttcctta ccaacggctt ttgctgttat aggagattta  23700
aagtgtactt cagatactag ttatattaat gataaagaca ccggtcctcc tcctataagt  23760
actgatactg ttgatgttac taatggtttg ggtacttatt atgttttaga tcgtgtgtat  23820
ttaaatacta cgttgtttct taatggttat taccctactt caggttccac atatcgtaat  23880
atggcactga agggaagtgt actattgagc agactatggt ttaaaccacc atttctttct  23940
gattttatta atggtatttt tgctaaggtc aaaaatacca aggttattaa agatcgtgta  24000
atgtatagtg agttccctgc tataactata ggtagtactt ttgtaaatac atcctatagt  24060
gtggtagtac aaccacgtac aatcaattca acacaggatg gttataataa attacaaggt  24120
cttttagagg tctctgtttg ccagtataat atgtgcgagt acccacaaac gatttgtcat  24180
cctaacctgg gtaatcatcg caaagaacta tggcatttgg atacaggtgt tgtttcctgt  24240
ttatataagc gtaatttcac atatgatgtg aatgctgatt atttgtattt tcatttttat  24300
caagaaggtg gtacttttta tgcatatttt acagacactg gtgttgttac taagtttttg  24360
tttaatgttt atttaggcat ggcgctttca cactattatg tcatgcctct gacttgtaat  24420
agtaaggtta agaatggttt tactttagaa tattgggtta cacctctcac ttctagacaa  24480
tatttactcg ctttcaatca agatggtatt atttttaatg ctgttgattg tatgagtgat  24540
tttatgagtg agattaagtg taaaacacaa tctatagcac cacctactgg tgtttatgaa  24600
ttaaacggtt acactgttca gccaatcgca gatgtttacc gacgtaaact taatcttccc  24660
aattgcaata tagaagcttg gcttaatgat aagtcggtgc cctctccatt aaattgggaa  24720
cgtaagacat tttcaaattg taattttaat atgagcagcc tgatgtcttt tattcaggca  24780
gactcattta cttgtaataa tattgatgct gctaagatat atggtatgtg tttttccagc  24840
ataactatag ataagtttgc tatacccaat ggcaggaagg ttgacctaca attgggtaat  24900
ttgggctatt tgcagtcatt taactataga attgatacta ctgcaacaag ttgtcagttg  24960
tattataatt tacctgctgc taatgtttct gttagcaggt ttaatccttc tacttggaat  25020
aagagatttg gttttataga agattctgtt tttaagcctc gacctgcagg tgttcttact  25080
aatcatgatg tagtttatgc acaacactgt ttcaaagctc ctaaaaattt ctgtccgtgt  25140
aaattgaatg gttcgtgtgt aggtagtggt cctggtaaaa ataatggtat aggcacttgt  25200
cctgcaggta ctaattattt aacttgtgat aatttgtgca ctcctgatcc tattacattt  25260
aaagctacag gtacttataa gtgcccccaa actaaatctt tagttggcat aggtgagcac  25320
tgttcgggtc ttgctgttaa aagtgattat tgtggaggca attcttgtac ttgccgacca  25380
```

-continued

```
caagcatttt tgggttggtc tgcagactct tgtttacaag gagacaagtg taatattttt  25440
gctaatttta ttttgcatga tgttaatagt ggtcttactt gttctactga tttacaaaaa  25500
gctaacacag acataattct tggtgtttgt gttaattatg acctctatgg tattttaggc  25560
caaggcattt ttgttgaggt taatgcgact tattataata gttggcagaa ccttttatat  25620
gattctaatg gtaatctcta cggttttaga gactacataa caaacagaac ttttatgatt  25680
cgtagttgct atagcggtcg tgtttctgcg gcctttcacg ctaactcttc cgaaccagca  25740
ttgctatttc ggaatattaa atgcaactac gtttttaata atagtcttac acgacagctg  25800
caacccatta actattttga tagttatctt ggttgtgttg tcaatgctta taatagtact  25860
gctatttctg ttcaaacatg tgatctcaca gtaggtagtg gttactgtgt ggattactct  25920
aaaaacagac gaagtcgtgg agcgattacc actggttatc ggtttactaa ttttgagcca  25980
tttactgtta attcagtaaa cgatagttta gaacctgtag gtggtttgta tgaaattcaa  26040
ataccttcag agtttactat aggtaatatg gaggagttta ttcaaacaag ctctcctaaa  26100
gttactattg attgtgctgc atttgtctgt ggtgattatg cagcatgtaa atcacagttg  26160
gttgaatatg gtagtttctg tgataacatt aatgccatac tcacagaagt aaatgaacta  26220
cttgacacta cacagttgca agtagctaat agtttaatga atggtgttac tcttagcact  26280
aagcttaaag atggcgttaa tttcaatgta gacgacatca atttttcccc tgtattaggt  26340
tgtctaggca gcgaatgtag taaagcttcc agtagatctg ctatagagga tttacttttt  26400
gataaagtaa agttatctga tgtcggtttt gttgaggctt ataataattg tacaggaggt  26460
gccgaaatta gggacctcat ttgtgtgcaa agttataaag gcatcaaagt gttgcctcca  26520
ctgctctcag aaaatcagat cagtggatac actttggctg ccacctctgc tagtctattt  26580
cctctttgga cagcagcagc aggtgtacca ttttatttaa atgttcagta tcgcattaat  26640
gggcttggtg tcaccatgga tgtgctaagt caaaatcaaa agcttattgc taatgcattt  26700
aacaatgccc tttatgctat tcaggaaggg ttcgatgcaa ctaattctgc tttagttaaa  26760
attcaagctg ttgttaatgc aaatgctgaa gctcttaata acttattgca acaactctct  26820
aatagatttg gtgctataag tgcttcttta caagaaattc tatctagact tgatgctctt  26880
gaagcggaag ctcagataga tagacttatt aatggtcgtc ttaccgctct taatgcttat  26940
gtttctcaac agcttagtga ttctacactg gtaaaattta gtgcagcaca agctatggag  27000
aaggttaatg aatgtgtcaa aagccaatca tctaggataa atttctgtgg taatggtaat  27060
catattatat cattagtgca gaatgctcca tatggtttgt attttatcca ctttagttat  27120
gtccctacta agtatgtcac agcgagggtt agtcctggtc tgtgcattgc tggtgataga  27180
ggtatagctc ctaagagtgg ttattttgtt aatgtaaata atacttggat gtacactggt  27240
agtggttact actaccctga acctataact gaaaataatg ttgttgttat gagtacctgc  27300
gctgttaatt atactaaagc gccgtatgta atgctgaaca cttcaatacc caaccttcct  27360
gattttaagg aagagttgga tcaatggttt aaaaatcaaa catcagtggc accagatttg  27420
tcacttgatt atataaatgt tacattcttg gacctacaag ttgaaatgaa taggttacag  27480
gaggcaataa aagtcttaaa tcagagctac atcaatctca aggacattgg tacatatgaa  27540
tattatgtaa aatggccttg gtatgtatgg cttttaatct gccttgctgg tgtagctatg  27600
cttgttttac tattcttcat atgctgttgt acaggatgtg ggactagttg ttttaagaaa  27660
tgtggtggtt gttgtgatga ttatactgga taccaggagt tagtaatcaa aacttcacat  27720
```

-continued

```
gacgactaag ttcgtctttg attcattgca ctgatctctt gttagatctt tttgcaatct  27780
agcatttgtt aaagttctta aggccacgcc ctattaatgg acatttggag acctgagaag  27840
aaatatctcc gttatattaa cggttttaat gtctcagaat tagaagatgc ttgttttaaa  27900
tttaactatc aatttcctaa agtaggatat tgtagagttc ctagtcatgc ttggtgccgt  27960
aatcaaggta gattttgtgc tacattcact ctttatggta aatccaaaca ttatgataaa  28020
tattttggag taataaatgg tttcacagca ttcgctaata ctgtagagga tgctgttaac  28080
aaactggttt tcttagctgt tgactttatt acctggcgca gacaggagtt aaatgtttat  28140
ggctgatgct tatcttgcag acactgtgtg gtatgtgggg caaataattt ttatagttgc  28200
catttgttta ttggttacaa tagttgtagt ggcatttttg gcaactttta aattgtgtat  28260
tcaactttgc ggtatgtgta ataccttagt actgtcccct tctatttatg tgtttaatag  28320
aggtaggcag ttttatgagt tttacaatga tgtaaaacca ccagtccttg atgtggatga  28380
cgtttaggta atccaaacat tatgagtagt aaaactacac cagcaccagt ttatatctgg  28440
actgctgatg aagctattaa attcctaaag gaatggaatt tttctttggg tattatacta  28500
ctttttatta caatcatatt gcaatttgga tatacaagtc gcagtatgtt tgtttatgtt  28560
attaagatga ttattttgtg gcttatgtgg ccccttacta taatcttaac tattttcaat  28620
tgcgtatacg cattgaataa tgtgtatctt ggcctttcta tagtttttac catagtggcc  28680
attattatgt ggattgtgta ttttgtgaat agtatcaggt tgtttattag aactggaagt  28740
ttttggagtt tcaacccaga aacaaacaac ttgatgtgta tagatatgaa aggaacaatg  28800
tatgttaggc cgataattga ggactatcat actctgacgg tcacaataat acgcggccat  28860
ctttacattc aaggtataaa actaggtact ggctattctt tggcagattt gccagcttat  28920
atgactgttg ctaaggttac acacctgtgc acatataagc gtggttttct tgacaggata  28980
agcgatacta gtggttttgc tgtttatgtt aagtccaaag tcggtaatta ccgactgcca  29040
tcaacccaaa agggttctgg catggacacc gcattgttga gaaataatat ctaaatttta  29100
aggatgtctt ttactcctgg taagcaatcc agtagtagag cgtcctctgg aaatcgttct  29160
ggtaatggca tcctcaagtg ggccgatcag tccgaccagt ttagaaatgt tcaaaccagg  29220
ggtagaagag ctcaacccaa gcaaactgct acctctcagc aaccatcagg agggaatgtt  29280
gtaccctact attcttggtt ctctggaatt actcagtttc aaaagggaaa ggagtttgag  29340
tttgtagaag gacaaggtgt gcctattgca ccaggagtcc cagctactga agctaagggg  29400
tactggtaca gacacaacag acgttctttt aaaacagccg atggcaacca gcgtcaactg  29460
ctgccacgat ggtattttta ctatctggga acaggaccgc atgctaaaga ccagtacggc  29520
accgatattg acggagtcta ctgggtcgct agcaaccagg ctgatgtcaa taccccggct  29580
gacattgtcg atcgggaccc aagtagcgat gaggctattc cgactaggtt tccgcctggc  29640
acggtactcc ctcagggtta ctatattgaa ggctcaggaa ggtctgctcc taattccaga  29700
tctacttcgc gcacatccag cagagcctct agtgcaggat cgcgtagtag agccaattct  29760
ggcaatagaa cccctacctc tggtgtaaca cctgacatgg ctgatcaaat tgctagtctt  29820
gttctggcaa aacttggcaa ggatgccact aaacctcagc aagtaactaa gcatactgcc  29880
aaagaagtca gacagaaaat tttgaataag ccccgccaga agaggagccc caataaacaa  29940
tgcactgttc agcagtgttt tggtaagaga ggccctaatc agaattttgg tggtggagaa  30000
atgttaaaac ttggaactag tgacccacag ttccccattc ttgcagaact cgcacccaca  30060
gctggtgcgt ttttctttgg atcaagatta gagttggcca aagtgcagaa tttatctggg  30120
```

-continued

```
aatcctgacg agccccagaa ggatgtttat gaattgcgct ataacggcgc aattaggttt  30180

gacagtacac tttcaggttt tgagaccata atgaaggtgc tgaatgagaa tttgaatgcc  30240

tatcaacaac aagatggtat gatgaatatg agtccaaaac cacagcgtca gcgtggtcat  30300

aagaatggac aaggagaaaa tgataatata agtgttgcag tgcccaaaag ccgcgtgcag  30360

caaaataaga gtagagagtt gactgcagag gacatcagcc ttcttaagaa gatggatgag  30420

ccctatactg aagacacctc agaaatataa gagaatgaac cttatgtcgg catctggtgg  30480

taacccctcg cagaaaagtc gagataaggc actctctatc agaatggatg tcttgctgct  30540

ataatagata gagaaggtta tagcagacta tagattaatt agttgaaagt tttgtgttgt  30600

aatgtatagt gttggagaaa gtgaaagact tgcggaagta attgccgaca agtgcccaag  30660

ggaagagcca gcatgttaag ttaccaccca gtaattagta aatgaatgaa gttaattatg  30720

gccaattgga agaatcac                                                30738
```

<210> SEQ ID NO 10
<211> LENGTH: 255
<212> TYPE: DNA
<213> ORGANISM: Human coronavirus OC43

<400> SEQUENCE: 10

```
atgtttatgg ctgatgctta tcttgcagac actgtgtggt atgtggggca aataattttt     60

atagttgcca tttgtttatt ggttacaata gttgtagtgg catttttggc aacttttaaa    120

ttgtgtattc aactttgcgg tatgtgtaat accttagtac tgtccccttc tatttatgtg    180

tttaatagag gtaggcagtt ttatgagttt tacaatgatg taaaaccacc agtccttgat    240

gtggatgacg tttag                                                     255
```

<210> SEQ ID NO 11
<211> LENGTH: 693
<212> TYPE: DNA
<213> ORGANISM: Human coronavirus OC43

<400> SEQUENCE: 11

```
atgagtagta aaactacacc agcaccagtt tatatctgga ctgctgatga agctattaaa     60

ttcctaaagg aatggaattt ttctttgggt attatactac tttttattac aatcatattg    120

caatttggat atacaagtcg cagtatgttt gtttatgtta ttaagatgat tattttgtgg    180

cttatgtggc cccttactat aatcttaact attttcaatt gcgtatacgc attgaataat    240

gtgtatcttg gcctttctat agtttttacc atagtggcca ttattatgtg gattgtgtat    300

tttgtgaata gtatcaggtt gtttattaga actggaagtt tttggagttt caacccagaa    360

acaaacaact tgatgtgtat agatatgaaa ggaacaatgt atgttaggcc gataattgag    420

gactatcata ctctgacggt cacaataata cgcggccatc tttacattca aggtataaaa    480

ctaggtactg gctattcttt ggcagatttg ccagcttata tgactgttgc taaggttaca    540

cacctgtgca catataagcg tggttttctt gacaggataa gcgatactag tggttttgct    600

gtttatgtta agtccaaagt cggtaattac cgactgccat caacccaaaa gggttctggc    660

atggacaccg cattgttgag aaataatatc taa                                 693
```

<210> SEQ ID NO 12
<211> LENGTH: 4086
<212> TYPE: DNA
<213> ORGANISM: Human coronavirus OC43

<400> SEQUENCE: 12

```
atgtttttga tacttttaat ttccttacca acggcttttg ctgttatagg agatttaaag     60
tgtacttcag atactagtta tattaatgat aaagacaccg gtcctcctcc tataagtact    120
gatactgttg atgttactaa tggtttgggt acttattatg ttttagatcg tgtgtattta    180
aatactacgt tgtttcttaa tggttattac cctacttcag gttccacata tcgtaatatg    240
gcactgaagg gaagtgtact attgagcaga ctatggttta aaccaccatt tctttctgat    300
tttattaatg gtatttttgc taaggtcaaa aataccaagg ttattaaaga tcgtgtaatg    360
tatagtgagt tccctgctat aactataggt agtacttttg taaatacatc ctatagtgtg    420
gtagtacaac cacgtacaat caattcaaca caggatggtt ataataaatt acaaggtctt    480
ttagaggtct ctgtttgcca gtataaatatg tgcgagtacc cacaaacgat ttgtcatcct    540
aacctgggta atcatcgcaa agaactatgg catttggata caggtgttgt ttcctgttta    600
tataagcgta atttcacata tgatgtgaat gctgattatt tgtattttca tttttatcaa    660
gaaggtggta ctttttatgc atattttaca gacactggtg ttgttactaa gtttttgttt    720
aatgtttatt taggcatggc gctttcacac tattatgtca tgcctctgac ttgtaatagt    780
aaggttaaga atggttttac tttagaatat tgggttacac ctctcacttc tagacaatat    840
ttactcgctt tcaatcaaga tggtattatt tttaatgctg ttgattgtat gagtgatttt    900
atgagtgaga ttaagtgtaa aacacaatct atagcaccac ctactggtgt ttatgaatta    960
aacggttaca ctgttcagcc aatcgcagat gtttaccgac gtaaacttaa tcttcccaat   1020
tgcaatatag aagcttggct taatgataag tcggtgccct ctccattaaa ttgggaacgt   1080
aagacatttt caaattgtaa ttttaatatg agcagcctga tgtcttttat tcaggcagac   1140
tcatttactt gtaataatat tgatgctgct aagatatatg gtatgtgttt ttccagcata   1200
actatagata agtttgctat acccaatggc aggaaggttg acctacaatt gggtaatttg   1260
ggctatttgc agtcatttaa ctatagaatt gatactactg caacaagttg tcagttgtat   1320
tataatttac ctgctgctaa tgtttctgtt agcaggttta atccttctac ttggaataag   1380
agatttggtt ttatagaaga ttctgttttt aagcctcgac ctgcaggtgt tcttactaat   1440
catgatgtag tttatgcaca acactgtttc aaagctccta aaaatttctg tccgtgtaaa   1500
ttgaatggtt cgtgtgtagg tagtggtcct ggtaaaaata atggtatagg cacttgtcct   1560
gcaggtacta attatttaac ttgtgataat ttgtgcactc ctgatcctat tacatttaaa   1620
gctacaggta cttataagtg cccccaaact aaatctttag ttggcatagg tgagcactgt   1680
tcgggtcttg ctgttaaaag tgattattgt ggaggcaatt cttgtacttg ccgaccacaa   1740
gcatttttgg gttggtctgc agactcttgt ttacaaggag acaagtgtaa tatttttgct   1800
aattttattt tgcatgatgt taatagtggt cttacttgtt ctactgattt acaaaaagct   1860
aacacagaca taattcttgg tgtttgtgtt aattatgacc tctatggtat tttaggccaa   1920
ggcatttttg ttgaggttaa tgcgacttat tataatagtt ggcagaacct tttatatgat   1980
tctaatggta atctctacgg ttttagagac tacataacaa acagaacttt tatgattcgt   2040
```

-continued

```
agttgctata gcggtcgtgt ttctgcggcc tttcacgcta actcttccga accagcattg   2100
ctatttcgga atattaaatg caactacgtt tttaataata gtcttacacg acagctgcaa   2160
cccattaact attttgatag ttatcttggt tgtgttgtca atgcttataa tagtactgct   2220
atttctgttc aaacatgtga tctcacagta ggtagtggtt actgtgtgga ttactctaaa   2280
aacagacgaa gtcgtggagc gattaccact ggttatcggt ttactaattt tgagccattt   2340
actgttaatt cagtaaacga tagtttagaa cctgtaggtg gtttgtatga aattcaaata   2400
ccttcagagt ttactatagg taatatggag gagtttattc aaacaagctc tcctaaagtt   2460
actattgatt gtgctgcatt tgtctgtggt gattatgcag catgtaaatc acagttggtt   2520
gaatatggta gtttctgtga taacattaat gccatactca cagaagtaaa tgaactactt   2580
gacactacac agttgcaagt agctaatagt ttaatgaatg gtgttactct tagcactaag   2640
cttaaagatg gcgttaattt caatgtagac gacatcaatt tttcccctgt attaggttgt   2700
ctaggcagcg aatgtagtaa agcttccagt agatctgcta tagaggattt actttttgat   2760
aaagtaaagt tatctgatgt cggttttgtt gaggcttata ataattgtac aggaggtgcc   2820
gaaattaggg acctcatttg tgtgcaaagt tataaaggca tcaaagtgtt gcctccactg   2880
ctctcagaaa atcagatcag tggatacact ttggctgcca cctctgctag tctatttcct   2940
ctttggacag cagcagcagg tgtaccattt tatttaaatg ttcagtatcg cattaatggg   3000
cttggtgtca ccatggatgt gctaagtcaa aatcaaaagc ttattgctaa tgcatttaac   3060
aatgcccttt atgctattca ggaagggttc gatgcaacta attctgcttt agttaaaatt   3120
caagctgttg ttaatgcaaa tgctgaagct cttaataact tattgcaaca actctctaat   3180
agatttggtg ctataagtgc ttctttacaa gaaattctat ctagacttga tgctcttgaa   3240
gcggaagctc agatagatag acttattaat ggtcgtctta ccgctcttaa tgcttatgtt   3300
tctcaacagc ttagtgattc tacactggta aaatttagtg cagcacaagc tatggagaag   3360
gttaatgaat gtgtcaaaag ccaatcatct aggataaatt tctgtggtaa tggtaatcat   3420
attatatcat tagtgcagaa tgctccatat ggtttgtatt ttatccactt tagttatgtc   3480
cctactaagt atgtcacagc gagggttagt cctggtctgt gcattgctgg tgatagaggt   3540
atagctccta agagtggtta ttttgttaat gtaaataata cttggatgta cactggtagt   3600
ggttactact accctgaacc tataactgaa aataatgttg ttgttatgag tacctgcgct   3660
gttaattata ctaaagcgcc gtatgtaatg ctgaacactt caatacccaa ccttcctgat   3720
tttaaggaag agttggatca atggtttaaa aatcaaacat cagtggcacc agatttgtca   3780
cttgattata taaatgttac attcttggac ctacaagttg aaatgaatag gttacaggag   3840
gcaataaaag tcttaaatca gagctacatc aatctcaagg acattggtac atatgaatat   3900
tatgtaaaat ggccttggta tgtatggctt ttaatctgcc ttgctggtgt agctatgctt   3960
gttttactat tcttcatatg ctgttgtaca ggatgtggga ctagttgttt taagaaatgt   4020
ggtggttgtt gtgatgatta tactggatac caggagttag taatcaaaac ttcacatgac   4080
gactaa                                                              4086
```